(12) United States Patent
Mutzke

(10) Patent No.: US 9,616,084 B2
(45) Date of Patent: Apr. 11, 2017

(54) MANNOSE-CONTAINING SOLUTION FOR LYOPHILIZATION, TRANSFECTION AND/OR INJECTION OF NUCLEIC ACIDS

(71) Applicant: CureVac GmbH, Tubingen (DE)

(72) Inventor: Thorsten Mutzke, Reutlingen (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 14/492,334

(22) Filed: Sep. 22, 2014

(65) Prior Publication Data

US 2015/0141498 A1 May 21, 2015

Related U.S. Application Data

(63) Continuation of application No. 13/509,564, filed as application No. PCT/EP2010/006788 on Nov. 8, 2010, now abandoned.

(30) Foreign Application Priority Data

Dec. 9, 2009 (WO) .................. PCT/EP2009/008804

(51) Int. Cl.
| | |
|---|---|
| A61K 31/7004 | (2006.01) |
| A61K 31/7105 | (2006.01) |
| A61K 47/26 | (2006.01) |
| A61K 31/7088 | (2006.01) |
| C12N 15/87 | (2006.01) |
| A61K 39/00 | (2006.01) |
| A61K 47/12 | (2006.01) |
| A61K 48/00 | (2006.01) |

(52) U.S. Cl.
CPC ...... *A61K 31/7088* (2013.01); *A61K 39/0011* (2013.01); *A61K 47/12* (2013.01); *A61K 47/26* (2013.01); *A61K 48/00* (2013.01); *C12N 15/87* (2013.01); *A61K 2039/53* (2013.01)

(58) Field of Classification Search
CPC ............ A61K 31/7004; A61K 31/7105; A61K 39/0011; A61K 47/26; A61K 48/0008; A61K 2039/53
USPC ...... 514/23, 44; 536/23.1, 23.5, 23.7, 23.72, 536/23.74
See application file for complete search history.

(56) References Cited

U.S. PATENT DOCUMENTS

| | | | | |
|---|---|---|---|---|
| 5,747,462 A | * | 5/1998 | Fuentes ............... | A61K 31/7004 424/767 |
| 5,849,473 A | * | 12/1998 | Cabrera ............... | A01N 1/0221 424/561 |
| 6,313,102 B1 | * | 11/2001 | Colaco ..................... | A61K 9/19 426/241 |
| 2005/0032730 A1 | | 2/2005 | Von Der Mulbe et al. | |
| 2005/0059624 A1 | | 3/2005 | Hoerr et al. | |
| 2005/0250723 A1 | | 11/2005 | Hoerr et al. | |
| 2006/0188490 A1 | | 8/2006 | Hoerr et al. | |
| 2008/0025944 A1 | | 1/2008 | Hoerr | |
| 2008/0267873 A1 | | 10/2008 | Hoerr | |
| 2010/0092572 A1 | * | 4/2010 | Kaeuper ............... | A61K 9/5161 424/499 |
| 2010/0203076 A1 | | 8/2010 | Fotin-Mleczek | |
| 2010/0291156 A1 | | 11/2010 | Barner et al. | |
| 2010/0305196 A1 | | 12/2010 | Probst et al. | |
| 2011/0053829 A1 | | 3/2011 | Baumhof | |
| 2011/0250225 A1 | | 10/2011 | Fotin-Mleczek | |
| 2012/0021043 A1 | | 1/2012 | Kramps et al. | |

FOREIGN PATENT DOCUMENTS

| | | | |
|---|---|---|---|
| EP | 2 431 405 | 3/2012 | |
| WO | WO 2008/014979 | 2/2008 | |
| WO | WO 2008/077592 | 7/2008 | |
| WO | WO 2008/083949 | 7/2008 | |
| WO | WO 2009/125986 | * 10/2009 | ............ C12N 15/63 |

OTHER PUBLICATIONS

Cheng et al, Eur. J. Immunol. 34:1892-1900, 2004.*
Carralot et al, Cell. Mol. Life Sci. 61:2418-2424, 2004.*
Groth et al, Surgery 64(1):31-38, 1968.*
Scheel et al, Eur. J. Immunol. 35:1557-1566, 2005.*
"Mannose," Wikipedia website located at http://en.wikipedia.org/wiki/Mannose; downloaded Jun. 17, 2013.
Allison et al., "Mechanisms of protection of cationic lipid-DNA complexes during lyophilization," *J Pharm Sci.*, 89(5):682-691, 2000.
Boczkowski et al., "Dendritic cells pulsed with RNA are potent antigen-presenting cells in vitro and in vivo," *J Exp Med.*, 184(2):465-472, 1996.
Brody, "A spectrophotometric study on the desoxypentose nucleic acid—cysteine reaction," *Acta Chem. Scand.*, 7(3):502-506, 1953.
Brus et al., "Stabilization of oligonucleotide-polyethylenimine complexes by freeze-drying: physicochemical and biological characterization," *J Control Release*, 95(1):119-131, 2004.
Groth et al., "Effect of ribonucleic acid perfusion on canine kidney and liver homograft survival," *Surgery*, 64(1):31-38, 1968.
Hattori et al., "Enhanced DNA vaccine potency by mannosylated lipoplex after intraperitoneal administration," *J Gene Med.*, 8(7):824-834, 2006.
Hess et al., "Vaccination with mRNAs encoding tumor-associated antigens and granulocyte-macrophage colony-stimulating factor efficiently primes CTL responses, but is insufficient to overcome tolerance to a model tumor/self antigen," *Cancer Immunol Immunother.*, 55(6):672-683, 2006.

(Continued)

*Primary Examiner* — Kevin Hill
(74) *Attorney, Agent, or Firm* — Parker Highlander PLLC

(57) ABSTRACT

The present invention is directed to (the use of) a solution containing at least one nucleic acid (sequence) and free mannose for lyophilization, transfection and/or injection, particularly of RNA and mRNA. The inventive solution exhibits a positive effect on stabilization of the nucleic acid (sequence) during lyophilization and storage but also leads to a considerable increase of the transfection efficiency of a nucleic acid. It thus also increases in vivo expression of a protein encoded by such a nucleic acid upon increased transfection rate. The present invention is furthermore directed to a method of lyophilization using the mannose-containing solution, to pharmaceutical compositions, vaccines, kits, first and second medical uses applying such a mannose-containing solution and/or a nucleic acid (sequence) lyophilized or resuspended with such a solution.

20 Claims, 6 Drawing Sheets

(56) References Cited

OTHER PUBLICATIONS

Hoerr et al., "In vivo application of RNA leads to induction of specific cytotoxic T lymphocyl es and antibodies," *Eur J lmmunol.*, 30(1):1-7, 2000.

Irache et al., "Mannose-targeted systems for the delivery of therapeutics," *Expert Opin Drug Deliv.*, 5(6):703-724, 2008.

Jones et al., "Long-term storage of DNA-free RNA for use in vaccine studies," *Biotechniques*, 43(5):675-681, 2007.

Kawakami et al., "Mannose receptor-mediated gene transfer into macrophages using novel mannosylated cationic liposomes," *Gene Ther.*, 7(4):292-299, 2000.

Keler et al., "Mannose receptor-targeted vaccines," *Expert Opin Biol Ther.*, 4(12):1953-1962, 2004.

Li et al., "Lyophilization of cationic lipid-protamine-DNA (LPD) complexes," *J Pharm Sci.*, 89(3):355-364, 2000.

Maitani et al., "Effect of sugars on storage stability of lyophilized liposome/DNA complexes with high transfection efficiency," *Int J Pharm.*, 356(1-2):69-75, 2008.

Nakamura et al., "Enhanced gene transfection in macrophages by histidine-conjugated mannosylated cationic liposomes," *Biol. Pharm. Bull.*, 32(9):1628-1631, 2009.

Office Action issued in U.S. Appl. No. 13/509,564, mailed Feb. 26, 2013.

Office Action issued in U.S. Appl. No. 13/509,564, mailed Jun. 27, 2013.

Office Action issued in U.S. Appl. No. 13/509,564, mailed Oct. 28, 2013.

Pascolo, "Vaccination with messenger RNA (mRNA)," *Handb Exp Pharmacol.*, (183):221-235, 2008.

PCT International Preliminary Report on Patentability issued in International Application No. PCT/EP2010/006788, mailed Jun. 12, 2012.

PCT International Search Report and Written Opinion issued in International Application No. PCT/EP2010/006788, mailed Jan. 28, 2011.

Poxon et al., "The effect of lyophilization on plasmid DNA activity," *Pharm Dev Technol.*, 5(1):115-122, 2000.

Qiu et al., "Gene gun delivery of mRNA in situ results in efficient transgene expression and genetic immunization," *Gene Ther.*, 3(3):262-268, 1996.

Quaak et al., "GMP production of pDERMATT for vaccination against melanoma in a phase I clinical trial," *Eur J Pharm Biopharm.*, 70(2):429-438, 2008.

Scheel et al., "Toll-like receptor-dependent activation of several human blood cell types by protamine-condensed mRNA," *Eur J Immunol*, 35(5):1557-1566, 2005.

Smith et al., "Optimal storage conditions for highly dilute DNA samples: a role for trehalose as a preserving agent," *J Forensic Sci.*, 50(5):1101-1108, 2005.

Sun et al., "Sweet delivery—sugar translocators as ports of entry for antisense oligodeoxynucleotides in plant cells," *Plant J.*, 52(6):1192-1198, 2007.

Yadava et al., "Effect of lyophilization and freeze-thawing on the stability of siRNA-liposome complexes," *AAPS PharmSciTech.*, 9(2):335-341, 2008.

\* cited by examiner

```
   1  GGGAGAAAGC  UUGAGGAUGG  AGGACGCCAA  GAACAUCAAG  AAGGGCCCGG
  51  CGCCCUUCUA  CCCGCUGGAG  GACGGGACCG  CCGGCGAGCA  GCUCCACAAG
 101  GCCAUGAAGC  GGUACGCCCU  GGUGCCGGGC  ACGAUCGCCU  UCACCGACGC
 151  CCACAUCGAG  GUCGACAUCA  CCUACGCGGA  GUACUUCGAG  AUGAGCGUGC
 201  GCCUGGCCGA  GGCCAUGAAG  CGGUACGGCC  UGAACACCAA  CCACCGGAUC
 251  GUGGUGUGCU  CGGAGAACAG  CCUGCAGUUC  UUCAUGCCGG  UGCUGGGCGC
 301  CCUCUUCAUC  GGCGUGGCCG  UCGCCCCGGC  GAACGACAUC  UACAACGAGC
 351  GGGAGCUGCU  GAACAGCAUG  GGGAUCAGCC  AGCCGACCGU  GGUGUUCGUG
 401  AGCAAGAAGG  GCCUGCAGAA  GAUCCUGAAC  GUGCAGAAGA  AGCUGCCCAU
 451  CAUCCAGAAG  AUCAUCAUCA  UGGACAGCAA  GACCGACUAC  CAGGGCUUCC
 501  AGUCGAUGUA  CACGUUCGUG  ACCAGCCACC  UCCCGCCGGG  CUUCAACGAG
 551  UACGACUUCG  UCCCGGAGAG  CUUCGACCGG  GACAAGACCA  UCGCCCUGAU
 601  CAUGAACAGC  AGCGGCAGCA  CCGGCCUGCC  GAAGGGGGUG  GCCCUGCCGC
 651  ACCGGACCGC  CUGCGUGCGC  UUCUCGCACG  CCCGGGACCC  CAUCUUCGGC
 701  AACCAGAUCA  UCCCGGACAC  CGCCAUCCUG  AGCGUGGUGC  CGUUCCACCA
 751  CGGCUUCGGC  AUGUUCACGA  CCCUGGGCUA  CCUCAUCUGC  GGCUUCCGGG
 801  UGGUCCUGAU  GUACCGGUUC  GAGGAGGAGC  UGUUCCUGCG  GAGCCUGCAG
 851  GACUACAAGA  UCCAGAGCGC  GCUGCUCGUG  CCGACCCUGU  UCAGCUUCUU
 901  CGCCAAGAGC  ACCCUGAUCG  ACAAGUACGA  CCUGUCGAAC  CUGCACGAGA
 951  UCGCCAGCGG  GGGCGCCCCG  CUGAGCAAGG  AGGUGGGCGA  GGCCGUGGCC
1001  AAGCGGUUCC  ACCUCCCGGG  CAUCCGCCAG  GGCUACGGCC  UGACCGAGAC
1051  CACGAGCGCG  AUCCUGAUCA  CCCCCGAGGG  GGACGACAAG  CCGGGCGCCG
1101  UGGGCAAGGU  GGUCCCGUUC  UUCGAGGCCA  AGGUGGUGGA  CCUGGACACC
1151  GGCAAGACCC  UGGGCGUGAA  CCAGCGGGGC  GAGCUGUGCG  UGCGGGGGCC
1201  GAUGAUCAUG  AGCGGCUACG  UGAACAACCC  GGAGGCCACC  AACGCCCUCA
1251  UCGACAAGGA  CGGCUGGCUG  CACAGCGGCG  ACAUCGCCUA  CUGGGACGAG
1301  GACGAGCACU  UCUUCAUCGU  CGACCGGCUG  AAGUCGCUGA  UCAAGUACAA
1351  GGGCUACCAG  GUGGCGCCGG  CCGAGCUGGA  GAGCAUCCUG  CUCCAGCACC
1401  CCAACAUCUU  CGACGCCGGC  GUGGCCGGGC  UGCCGGACGA  CGACGCCGGC
1451  GAGCUGCCGG  CCGCGGUGGU  GGUGCUGGAG  CACGGCAAGA  CCAUGACGGA
1501  GAAGGAGAUC  GUCGACUACG  UGGCCAGCCA  GGUGACCACC  GCCAAGAAGC
1551  UGCGGGGCGG  CGUGGUGUUC  GUGGACGAGG  UCCCGAAGGG  CCUGACCGGG
1601  AAGCUCGACG  CCCGGAAGAU  CCGCGAGAUC  CUGAUCAAGG  CCAAGAAGGG
1651  CGGCAAGAUC  GCCGUGUAAG  ACUAGUUAUA  AGACUGACUA  GCCCGAUGGG
1701  CCUCCCAACG  GGCCCUCCUC  CCUCCUUGC  ACCGAGAUUA  AUAAAAAAAA
1751  AAAAAAAAAA  AAAAAAAAAA  AAAAAAAAAA  AAAAAAAAAA  AAAAAAAAAA
1801  AAAAAUAUU   CCCCCCCCCC  CCCCCCCCCC  CCCCCCCCCC  UCUAGACAAU
1851  UGGAAUU
```

Figure 5

```
   1  GGGAGAAAGC UUACCAUGGG CAGCAUCGGG GCCGCGUCGA UGGAGUUCUG
  51  CUUCGACGUG UUCAAGGAGC UGAAGGUCCA CCACGCCAAC GAGAACAUCU
 101  UCUACUGCCC GAUCGCCAUC AUGAGCGCGC UCGCCAUGGU GUACCUGGGC
 151  GCCAAGGACA GCACCCGGAC GCAGAUCAAC AAGGUGGUCC GCUUCGACAA
 201  GCUGCCCGGC UUCGGGGACU CGAUCGAGGC GCAGUGCGGC ACCAGCGUGA
 251  ACGUGCACAG CUCGCUCCGG GACAUCCUGA ACCAGAUCAC CAAGCCGAAC
 301  GACGUCUACA GCUUCAGCCU GGCCUCGCGG CUCUACGCCG AGGAGCGCUA
 351  CCCGAUCCUG CCCGAGUACC UGCAGUGCGU GAAGGAGCUC UACCGGGGCG
 401  GGCUGGAGCC GAUCAACUUC CAGACGGCGG CCGACCAGGC CCGGGAGCUG
 451  AUCAACAGCU GGGUGGAGAG CCAGACCAAC GGCAUCAUCC GCAACGUCCU
 501  CCAGCCGUCG AGCGUGGACA GCCAGACCGC GAUGGUGCUG GUCAACGCCA
 551  UCGUGUUCAA GGGCCUGUGG GAGAAGACGU UCAAGGACGA GGACACCCAG
 601  GCCAUGCCCU UCCGGGUGAC CGAGCAGGAG UCGAAGCCGG UCCAGAUGAU
 651  GUACCAGAUC GGGCUCUUCC GGGUGGCGAG CAUGGCCAGC GAGAAGAUGA
 701  AGAUCCUGGA GCUGCCGUUC GCCUCGGGCA CGAUGAGCAU GCUCGUGCUG
 751  CUGCCCGACG AGGUCAGCGG CCUCGAGCAG CUGGAGUCGA UCAUCAACUU
 801  CGAGAAGCUG ACCGAGUGGA CCAGCAGCAA CGUGAUGGAG GAGCGCAAGA
 851  UCAAGGUGUA CCUCCCGCGG AUGAAGAUGG AGGAGAAGUA CAACCUGACG
 901  UCGGUCCUGA UGGCGAUGGG GAUCACCGAC GUGUUCAGCA GCUCGGCCAA
 951  CCUCAGCGGC AUCAGCUCGG CCGAGAGCCU GAAGAUCAGC CAGGCGGUGC
1001  ACGCCGCCCA CGCGGAGAUC AACGAGGCCG GCCGGGAGGU CGUGGGGUCG
1051  GCCGAGGCGG GCGUGGACGC CGCCAGCGUC AGCGAGGAGU CCGCGCGGA
1101  CCACCCGUUC CUGUUCUGCA UCAAGCACAU CGCCACCAAC GCCGUGCUCU
1151  UCUUCGGCCG GUGCGUGUCG CCCUGACCAC UAGUUAUAAG ACUGACUAGC
1201  CGAUGGGCC UCCCAACGGG CCCUCCUCCC CUCCUUGCAC CGAGAUUAAU
1251  AAAAAAAAAA AAAAAAAAAA AAAAAAAAAA AAAAAAAAAA AAAAAAAAAA
1301  AAAAAAAAAA AAAAUAUUCC CCCCCCCCCC CCCCCCCCCC CCCCCCCCUC
1351  UAGACAAUUG GAAUU
```

Figure 6

SEQUENCE LISTING

```
<160> NUMBER OF SEQ ID NOS: 3

<210> SEQ ID NO 1
<211> LENGTH: 1857
<212> TYPE: RNA
<213> ORGANISM: Artificial Sequence
<220> FEATURE:
<223> OTHER INFORMATION: Description of Artificial Sequence: mRNA coding
      for Photinus pyralis luciferase: pCV19-Pp luc(GC)-muag-A70-c30

<400> SEQUENCE: 1
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu gguguucgug agcaagaagg ccugcagaa      420 gauccugaac gugcagaaga gcugcccau cauccagaag aucaucauca uggacagcaa     480
gaccgacuac cagggcuucc agucgaugua cacguucgug accagccacc uccgccggg      540 cuucaacgag uacgacuucg ucccggagag cuucgaccgg gacaagacca ucgcccugau     600
```

```
caugaacagc agcggcagca ccggccugcc gaaggggggug gcccugccgc accggaccgc    660
cugcgugcgc uucucgcacg cccgggaccc caucuucggc aaccagauca ucccggacac    720
cgccauccug agcgugggugc cguuccacca cggcuucggc auguucacga cccugggcua    780
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccgugggcc aagcgguucc accucccggg   1020
cauccgccag ggcuacggcc ugaccgagac cacgagcgcg auccugauca ccccgagggg   1080
ggacgacaag ccgggcgccg ugggcaaggu ggucccguuc uucgaggcca aggugguga    1140 ccuggacacc ggcaagaccc uggggcgugaa ccagcggggc gagcugugcg ugcggggggcc   1200 gaugaucaug agcggcuacg ugaacaaccc ggaggccacc aacgcccuca ucgacaagga   1260
cggcuggcug cacagcggcg acaucgccua cuggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcgggggcgg   1560 cguggugguc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgaduggg ccucccaacg ggcccuccuc cccuccuugc accgagauua   1740
auaaaaaaaa aaaaaaaaaa aaaaaaaaaa aaaaaaaaaa aaaaaaaaaa aaaaaaaaaa   1800
aaaaaauauu ccccccccc cccccccccc cccccccccc ucuagacaau uggaauu    1857

<210> SEQ ID NO 2
<211> LENGTH: 1365
<212> TYPE: RNA
<213> ORGANISM: Artificial Sequence
<220> FEATURE:
<223> OTHER INFORMATION: Desription of Artificial Sequence: mRNA coding
      for Gallus gallus ovalbumin: CAP-GgOva(GC)-muag-A70-c30

<400> SEQUENCE: 2
gggagaaagc uuaccauggg cagcaucggg gccgcgucga uggaguucug cuucgacgug    60
uucaaggagc ugaaggucca ccacgccaac gagaacaucu ucuacugccc gaucgccauc   120
augagcgcgc ucgccaugguu guaccugggc gccaaggaca gcacccggac gcagaucaac   180
aagguggucc gcuucgacaa gcugcccggc uucggggacu cgaucgaggc gcagugcggc   240
accagcguga acgugcacag cucgcuccgg gacauccuga accagaucac caagccgaac   300
gacgucuaca gcuucagccu ggccucgcgg cucuacgccg aggagcgcua cccgauccug   360
cccgaguacc ugcagugcgu gaaggagcuc uaccggggcg gcuggagcc gaucaacuuc   420 cagacggcgg ccgaccaggc ccgggagcug aucaacagcu ggguggagag ccagaccaac   480
ggcaucaucc gcaacgucccu ccagccgucg agcguggaca ccagaccgc gauggugcug   540 gucaacgcca ucguguucaa gggccugugg gagaagacgu caaggacga ggacacccag   600 gccaugcccu uccgggugac cgagcaggag ucgaagccgg uccagaugau guaccagauc   660
ggcucuuucc gggugcgag cauggccagc gagaagauga agauccugga gcugccguuc   720
gccucgggca cgaugagcau gcucgugcug cugcccgacg aggucagcgg ccucgagcag   780
```

```
cuggagucga ucaucaacuu cgagaagcug accgagugga ccagcagcaa cgugauggag      840
gagcgcaaga ucaaggugua ccucccgcgg augaagaugg aggagaagua caaccugacg      900
ucgguccuga uggcgauggg gaucaccgac guguucagca gcucggccaa ccucagcggc      960
aucagcucgg ccgagagccu gaagaucagc caggcggugc acgccgccca cgcggagauc     1020
aacgaggccg gccgggaggu cguggggucg gccgaggcgg gcguggacgc cgccagcguc     1080
agcgaggagu uccgcgcgga ccacccguuc cuguucugca ucaagcacau cgccaccaac     1140
gccgugcucu ucuucggccg gugcgugucg cccugaccac uaguuauaag acugacuagc     1200
ccgaugggcc ucccaacggg cccuccuccc cuccuugcac cgagauuaau aaaaaaaaaa     1260
aaaaaaaaaa aaaaaaaaaa aaaaaaaaaa aaaaaaaaaa aaaaaaaaaa aaaauauucc     1320
cccccccccc cccccccccc ccccccccuc uagacaauug gaauu                    1365
```

<210> SEQ ID NO 3
<211> LENGTH: 13
<212> TYPE: RNA
<213> ORGANISM: Artificial Sequence
<220> FEATURE:
<223> OTHER INFORMATION: Description of sequence: Kozak sequence

<400> SEQUENCE: 3

```
gccgccacca ugg                                                          13
```

MANNOSE-CONTAINING SOLUTION FOR LYOPHILIZATION, TRANSFECTION AND/OR INJECTION OF NUCLEIC ACIDS

CROSS REFERENCE TO RELATED APPLICATIONS

This application is a continuation of U.S. application Ser. No. 13/509,564, filed May 11, 2012, which is the U.S. National Stage Application of International Application No. PCT/EP2010/006788, filed Nov. 8, 2010, which claims priority to International Application No. PCT/EP2009/008804, filed Dec. 9, 2009, all of which are incorporated herein by reference in their entirety for all purposes.

FIELD OF THE INVENTION

The present invention is directed to (the use of) a solution containing at least one nucleic acid (sequence) and free mannose for lyophilization, transfection and/or injection, particularly of RNA and mRNA. The inventive solution exhibits a positive effect on stabilization of the nucleic acid (sequence) during lyophilization and storage but also leads to a considerable increase of the transfection efficiency of a nucleic acid. It thus also increases in vivo expression of a protein encoded by such a nucleic acid upon increased transfection rate. The present invention is furthermore directed to a method of lyophilization using the mannose-containing solution, to pharmaceutical compositions, vaccines, kits, first and second medical uses applying such a mannose-containing solution and/or a nucleic acid (sequence) lyophilized or resuspended with such a solution.

BACKGROUND OF THE INVENTION

In gene therapy and many other therapeutically relevant biochemical and biotechnological applications the use of nucleic acids for therapeutic and diagnostic purposes is of major importance. As an example, rapid progress has occurred in recent years in the field of gene therapy and promising results have been achieved. Nucleic acids are therefore regarded as important tools for gene therapy and prophylactic and therapeutic vaccination against infectious and malignant diseases.

Nucleic acids, both DNA and RNA, have been used widely in gene therapy, either in naked or in complexed form. In this context, the application of nucleic acids and particularly of RNA for therapeutic vaccination is revised permanently. On the one hand, nucleic acids and particularly RNA or mRNA molecules can be optimized for a more efficient transcription rate. The 5' Cap structure, the untranslated and translated regions are typically modified to stabilize the molecule or to change its characteristics to enhance its translation properties (see e.g. Pascolo, S. (2008), Handb Exp Pharmacol (183): 221-35). Further, different formulations of nucleic acids and particularly of mRNA molecules or different delivery routes are investigated to achieve improved expression levels. To mention are the encapsulation into cationic liposomes or cationic polymers (see e.g. Hoerr, I., R. Obst, et al. (2000), Eur J Immunol 30(1): 1-7.; Hess, P. R., D. Boczkowski, et al. (2006), Cancer Immunol Immunother 55(6): 672-83; Scheel, B., R. Teufel, et al. (2005), Eur J Immunol 35(5): 1557-66), the needleless delivery of gold particles coated by mRNA using a gene gun (see e.g. Qiu, P., P. Ziegelhoffer, et al. (1996). "Gene gun delivery of mRNA in situ results in efficient transgene expression and genetic immunization." Gene Ther 3(3): 262-8), the transfection of in vitro generated autologous APCs that are re-administred to patients (see e.g. Boczkowski, D., S. K. Nair, et al. (1996). "Dendritic cells pulsed with RNA are potent antigen-presenting cells in vitro and in vivo." J Exp Med 184(2): 465-72; Boczkowski, et al, 1996, supra), and the direct injection of naked RNA (see Hoerrr et al, 2000, supra). Despite all progress achieved regarding gene delivery it is very important to improve further transfection efficiency to make nucleic acids especially RNA applicable for all imaginable therapeutic purposes.

Application of RNA thus represents a favored tool in modern molecular medicine. It also exhibits some superior properties over DNA cell transfection. As generally known, transfection of DNA molecules may lead to serious problems. E.g. application of DNA molecules bears the risk that the DNA integrates into the host genome. Integration of foreign DNA into the host genome can have an influence on expression of the host genes and possibly triggers expression of an oncogene or destruction of a tumor suppressor gene. Furthermore, a gene—and therefore the gene product—which is essential to the host may also be inactivated by integration of the foreign DNA into the coding region of this gene. There may be a particular danger if integration of the DNA takes place into a gene which is involved in regulation of cell growth. Nevertheless, DNA still represents an important tool, even though some risks are associated with the application of DNA. These risks do not occur if RNA, particularly mRNA, is used instead of DNA. An advantage of using RNA rather than DNA is that no virus-derived promoter element has to be administered in vivo and no integration into the genome may occur. Furthermore, the RNA has not to overcome the barrier to the nucleus. However, a main disadvantage resulting from the use of RNA is due to its huge instability. Even though it is understood that DNA, e.g., naked DNA, introduced into a patient' circulatory system is typically not stable and therefore may have little chance of affecting most disease processes (see e.g. Poxon et al., Pharmaceutical development and Technology, 5(1), 115-122 (2000)) the problem of stability is even more evident in the case of RNA. As generally known, the physico chemical stability of RNAs in solution is extremely low. RNA is very susceptible to hydrolysis by ubiquitous ribonucleases and is typically completely degraded already after a few hours or days in solution. This even occurs in the absence of RNases, e.g. when stored a few hours or days in solution at room temperature.

To avoid such degradation the RNA is typically stored at $-20°$ C. or even $-80°$ C. and RNAse free conditions to prevent a prior degradation of the RNA. This method, however, does not prevent a loss of function effectively and additionally is very cost-intensive for shipping when these temperatures have to be guaranteed. One further method for stabilization comprises lyophilization or freeze-drying of the RNA. Lyophilization is a worldwide known and recognized method in the art to enhance storage stability of temperature sensitive biomolecules, such as nucleic acids. During lyophilization, typically water is removed from a frozen sample containing nucleic acids via sublimation. The process of lyophilization is usually characterized by a primary and a secondary drying step. During the primary drying step, free, i.e. unbound, water surrounding the nucleic acid (sequence) and optionally further components, escapes from the solution. Subsequent thereto water being bound on a molecular basis by the nucleic acids may be removed in a secondary drying step by adding thermal energy. In both cases the hydration sphere around the nucleic acids is lost.

During lyophilization the sample containing nucleic acids is initially cooled below the freezing point of the solution and accordingly of the water contained therein. As a result, the water freezes. Dependent on temperature, rate of cooling down (freezing rate), and the time for freezing, the crystal structure of water is changed. This exhibits physical stress on the nucleic acid (sequence) and other components of the solution, which may lead to a damage of the nucleic acid, e.g. breakage of strands, loss of supercoiling, etc. Furthermore, due to the decrease of volume and loss of the hydration sphere, autocatalytic degradation processes are favored e.g. by traces of transition metals. Additionally, significant changes of pH are possible by concentration of traces of acids and bases.

Lyophilization involves two stresses, freezing and drying. Both are known to damage nucleic acids, such as non-viral vectors or plasmid DNA. In the literature, a number of cryoprotectants and lyoprotectants are discussed for lyophilization purposes to prevent these damages. In this context, cryoprotectants are understood as excipients, which allow influencing the structure of the ice and/or the eutectical temperature of the mixture. Lyoprotectants are typically excipients, which partially or totally replace the hydration sphere around a molecule and thus prevent catalytic and hydrolytic processes.

In the specific context of DNA, lyophilization causes the removal of the hydration sphere around the DNA, wherein it appears that there are approximately 20 water molecules per nucleotide pair bound most tightly to DNA. These water molecules do not form an ice-like structure upon low-temperature cooling. Upon DNA dehydration over hygroscopic salts at 0% relative humidity, only five or six water molecules remain (see e.g. Tao et al., Biopolymers, 28, 1019-1030 (1989)). Lyophilization may increase the stability of DNA under long-term storage, but may also cause some damage upon the initial lyophilization process, potentially through changes in the DNA secondary structure, breaks of the nucleic acid chain(s) or the concentration of reactive elements such as contaminating metals. Lyophilization can also cause damage upon the initial lyophilization process in other nucleic acid, e.g. RNA. Agents that can substitute for non-freezable water, such as some carbohydrates, can demonstrate cryoprotective properties for DNA and other molecules during lyophilization of intact bacteria (see e.g. Israeli et al, Cryobiology, 30, 519-523 (1993); or Rudolph et al, Arch. Biochem. Biophys., 245, 134-143 (1986)).

During lyophilization, specific carbohydrates, such as several sugars, appear to play a central role in stabilization of the nucleic acid. However, when using cryoprotectants and lyoprotectants, no general rule may be applied with respect to their impact on different groups of compounds. Therefore, in many cases an optimal formulation has to be found using empirical methods.

In this context, specific carbohydrates are utilized in the art as lyoprotective substances for enhancing stability of the nucleic acid (sequence) during lyophilization. They exhibit an effect on storage stability after lyophilisation of pure nucleic acids or nucleic acid (sequence) complexes (see e.g. Maitani, Y., Y. Aso, et al. (2008), Int J Pharm 356(1-2): 69-75; Quaak, S. G., J. H. van den Berg, et al. (2008), Eur J Pharm Biopharm 70(2): 429-38; Jones, K. L., D. Drane, et al. (2007), Biotechniques 43(5): 675-81; Molina, M. C., S. D. Allison, et al. (2001), J Pharm Sci 90(10): 1445-55; and Allison, S. D. and T. J. Anchordoquy (2000), J Pharm Sci 89(5): 682-91). Lyoprotective properties are particularly described for sucrose, glucose, and trehalose. They allow to restore at least in part the transfection efficiency which is otherwise lost in many cases after lyophilisation (see Maitani et al, 2008, supra; Yadava, P., M. Gibbs, et al. (2008). AAPS PharmSciTech 9(2): 335-41; Werth, S., B. Urban-Klein, et al. (2006), J Control Release 112(2): 257-70; Brus, C., E. Kleemann, et al. (2004), J Control Release 95(1): 119-31; Poxon, S. W. and J. A. Hughes (2000), Pharm Dev Technol 5(1): 115-22; Anchordoquy, T. J., J. F. Carpenter, et al. (1997), Arch Biochem Biophys 348(1): 199-206). Sugars are able to prevent loss in activity due to the lyophilization process mainly by preventing particle fusion/aggregation especially in the case of liposome complexed nucleic acids (see Yadava et al, 2008, supra; Katas, H., S. Chen, et al. (2008), J Microencapsul: 1-8; Molina et al, supra, 2001).

Particularly, Poxon et al. (2000, supra) investigated the effect of lyophilization on plasmid DNA activity. Poxon et al. (2000, supra) hypothesized, that a change in the DNA conformation from supercoiled to open circular and linear form would be indicative of damage of the plasmid DNA. However, the percentage of supercoiled DNA did not change after lyophilization and subsequent DMED treatment, suggesting that other effects drew responsible for the loss of transfection efficiency. Poxon et al. (2000, supra) found that a decrease in plasmid DNA activity as measured by an in vitro transfection assay can be ameliorated by the use of carbohydrates during lyophilization of the plasmid DNA but he did not found that any of the used carbohydrates increased the transfection efficiency of the plasmid DNA. As lyoprotectants, glucose (monosaccaride), sucrose and lactose (disaccharides) were used. Poxon et al. (2000, supra), however, only carried out investigations with plasmid DNA. They did also not investigate if the addition of saccharides to the lyophilization affects the stability of the lyophilized plasmid DNA.

Li et al. (see Li, B., S. Li, et al. (2000), J Pharm Sci 89(3): 355-64) furthermore showed that disaccharides are superior to monosaccharides using them as a cryoprotectant for lyophilization of lipid based gene delivery systems due to the prevention of aggregation. They noted that it is very important to prevent the particle size of the complexes during lyophilization. Unfortunately, in a specific example of lipid based gene delivery systems, lyophilization with mannose led to an increase in particle size, which was regarded as negative for transfection efficiency. Additionally Li et al. (2000, supra) showed that lipid delivery systems can be stored at room temperature without loss of transfection efficiency when lyophilized in 10% sucrose. Li et al. (2000, supra) did not examine the stabilization due to the presence of mannose as a lyoprotectant. More importantly, they did not observe an increase in the expression of the encoded protein due to the presence of sugar (sucrose and trehalose) in the injection buffer.

Even though many available prior art documents discuss the stabilization of nucleic acids during lyophilization in the context of plasmid DNA, only few publications focus on stabilization of other nucleic acids, such as RNAs, e.g. during lyophilization and long-term storage.

In this context, Jones et al (2007, supra) is one rare document, which examines the effect of sugars on long term stability of mRNA. It describes the possibility to prevent storage depending loss of transfection activity in vitro. Jones et al (2007, supra) uses trehalose as a lyoprotectant and shows a preventive effect on the loss of transfection activity at a storage temperature of 4° C. for a period of 6 months. Integrity of the mRNA was only measured by loss of weight after recovering. At elevated temperatures (room temperature and higher) degradation and a dramatic loss of transfection efficiency took place. Additionally; transfection efficiency could not be improved using trehalose as lyoprotectant.

In a further context, specific carbohydrates may also be utilized to improve biological activity and/or transfection efficiency, which is, at least at a first glance, independent from stability issues. Such an effect of specific carbohydrates, e.g. of mannose may be attributed to the interaction of these carbohydrates with specific receptors in the cell. As an example, the addition of mannose may involve the mannose receptor targeted transfer. The mannose receptor (MR) is primarily present on dendritic cells (DCs) and macrophages. The carbohydrate recognition domains of the MR recognizes carbohydrates (e.g. mannose, fucose, glucose, N-Acetylglucosamine, maltose) on the cell walls of infectious agents (mainly bacteria and yeast) which leads to rapid internalization and phagocytosis. This process can initiate effective immune defense. Several different strategies targeted to the MR have been used to enhance transfection levels or to develop upgraded vaccines (see Keler, T., V. Ramakrishna, et al. (2004). "Mannose receptor-targeted vaccines." Expert Opin Biol Ther 4(12): 1953-62). In this context, mannose modified non-viral DNA vectors, including cationic liposomes (Kawakami, S., A. Sato, et al. (2000), Gene Ther 7(4): 292-9; and Hattori, Y., S. Kawakami, et al. (2006), J Gene Med 8(7): 824-34), polyethyleneimine (Diebold, S. S., H. Lehrmann, et al. (1999), Hum Gene Ther 10(5): 775-86), poly L-lysine (Nishikawa, M., S. Takemura, et al. (2000), J Drug Target 8(1): 29-38), dendrimers (Arima, H., Y. Chihara, et al. (2006), J Control Release 116(1): 64-74) and chitosan (Kim, T. H., J. W. Nah, et al. (2006), J Nanosci Nanotechnol 6(9-10): 2796-803); (Hashimoto, M., M. Morimoto, et al. (2006), Biotechnol Lett 28(11): 815-21), have been reported (see also review: Irache, J. M., H. H. Salman, et al. (2008). "Mannose-targeted systems for the delivery of therapeutics." Expert Opin Drug Deliv 5(6): 703-24). However, in all cases mannose was covalently bound to the vector to ensure a combined uptake due to binding to the mannose receptor. However, the expression of the mannose receptor is restricted to a few cell types (especially dendritic cells) which are not excessively present in the dermis and therefore it appeared unlikely that free mannose improves the expression of the encoded protein due to an increased uptake in mannose receptor expressing cells.

The only case which is known in the prior art to use free sugar to enhance transfection efficiency is disclosed in Sun et al (see Sun, C., K. Ridderstrale, et al. (2007), *Plant J* 52(6): 1192-8). Sun et al. (2007) could show that sucrose can stimulate uptake of oligo deoxynucleotides (ODN) in human cells (in vitro). They investigated the effect of glucose and sucrose to the ODN delivery compared to the effect of oligofectamine, a commercially available lipid-based transfection reagent. Interestingly they observed that sucrose was 30% more potent than oligofectamine and even 60% more potent than glucose supporting ODN uptake. They hypothesized that sucrose is a common trigger for endocytosis in animal cells and therefore the ODN internalizes into endosomes together with the sucrose. Sun et al. (2007) only examined in vitro transfection assays which are very difficult to transfer to the in vivo situation due to the dilution effect. In tissues it thus appeared very unlikely that the nucleic acid and the sugar molecule enter the cell at the same time.

Summarizing the above, there is a long-lasting and urgent need in the art to provide means, which allow (a skilled person) to store RNA without a loss in activity, an effect, which is observed in many cases. Likewise, there is a long-lasting and urgent need to provide means, which allow (a skilled person) to enhance transfection efficiency of nucleic acids especially of RNA for in vitro and particularly for in vivo applications. In this context, a still most challenging problem of the prior art is the stability of the above defined nucleic acids, particularly during storage and delivery. Another challenging problem of the prior art, which in part due to the problem of stability, is the loss of activity subsequent to storage, or the loss of biological activity after lyophilization (e.g. increase in particle size, . . . ), which is observed for many nucleic acids. Finally, a further challenging problem of the prior art represents the small amount of expressed protein or small biological activity of the nucleic acid obtained upon transfection into the cell. Some further problems can be regarded in the provision of a suitable final dosage form for delivering these nucleic acids but also the production, transport and storage thereof. Especially transport of RNA is a remaining problem because it is very cost-intensive to ensure temperatures at −20° C. and below during shipment.

SUMMARY OF THE INVENTION

The present invention is summarized as (the use of) a solution and uses thereof containing at least one nucleic acid (sequence) and free mannose for lyophilization, transfection and/or injection, particularly of RNA and mRNA. The inventive solution exhibits a positive effect on stabilization of the nucleic acid (sequence) during lyophilization and storage but also leads to a considerable increase of the transfection efficiency of a nucleic acid. It thus also increases in vivo expression of a protein encoded by such a nucleic acid upon increased transfection rate. The present invention is furthermore directed to a method of lyophilization using the mannose-containing solution, to pharmaceutical compositions, vaccines, kits, first and second medical uses applying such a mannose-containing solution and/or a nucleic acid (sequence) lyophilized or resuspended with such a solution.

All of the challenging problems mentioned above in the background of the invention are solved by the present invention, particularly by the attached claims. According to a first aspect, the problem underlying the present invention is solved by (the use of) a solution containing at least one nucleic acid (sequence) and free mannose for lyophilization, transfection and/or injection. Preferably, the inventive solution containing at least one nucleic acid (sequence) and mannose stabilizes the at least one nucleic acid (sequence) contained in the inventive solution during lyophilization and/or improves biological activity of the nucleic acid (sequence). This is particularly preferable true, if a protein is encoded by the at least one nucleic acid (sequence), as expression of an encoded protein may be increased thereby. This solution is particularly surprising and was not suggested by any of the above mentioned prior art documents. In contrast, reviewing the prior art a skilled person would have rather suggested that—considering its teaching—addition of mannose as lyoprotectant diminishes transfection efficiency and even more problematic, may lead to a decrease of biological activity of the nucleic acid, or, if a protein is encoded, to a decrease of the expression of the encoded protein in vitro or in vivo. Regarding transfection the prior art only dealt with covalently bound mannose. Free mannose was never considered as suitable. As discussed above, in tissues it appears very unlikely that the nucleic acid and the sugar molecule enter the cell at the same time.

Therefore, it was highly surprising for the present inventors to see that free mannose can in fact improve transfection efficiency in vivo as outlined herein.

In summary it was particularly surprising to the inventors, that use of such a mannose containing solution was associated with the significant increase of storage capabilities, particularly the storage at room temperature or higher could be shown using mannose as lyoprotectant. Additionally, it was particularly surprising, that an increase in transfection efficiency due to the use of such a mannose containing solution was associated with the significant increase in biological activity. In contrast to the covalent binding shown in the art the present inventors used free mannose which was only added to the solution and which was not covalently bound to the nucleic acid. As a combined uptake in mannose receptor expressing cells is unlikely due to the dilution effect in the tissue a skilled person would never have suggested that mannose could improve transfection efficiency of nucleic acids, especially RNA. Particularly Sun et al. only examined in vitro transfection assays with free sugar containing solutions which are very difficult to transfer to the in vivo situation due to the dilution effect. Likewise, a skilled person would never have suggested that free mannose, could improve transfection efficiency of nucleic acids, especially RNA.

BRIEF DESCRIPTION OF THE DRAWINGS

The following Figures are intended to illustrate the invention further. They are not intended to limit the subject matter of the invention thereto.

FIG. 5: illustrates the mRNA sequence termed pCV19-Ppluc(GC)-muag-A70-C30 (SEQ ID NO: 1), coding for *Photinus pyralis* luciferase, which exhibits a length of 1857 nucleotides. The mRNA sequence contains following sequence elements:

Figure 1:
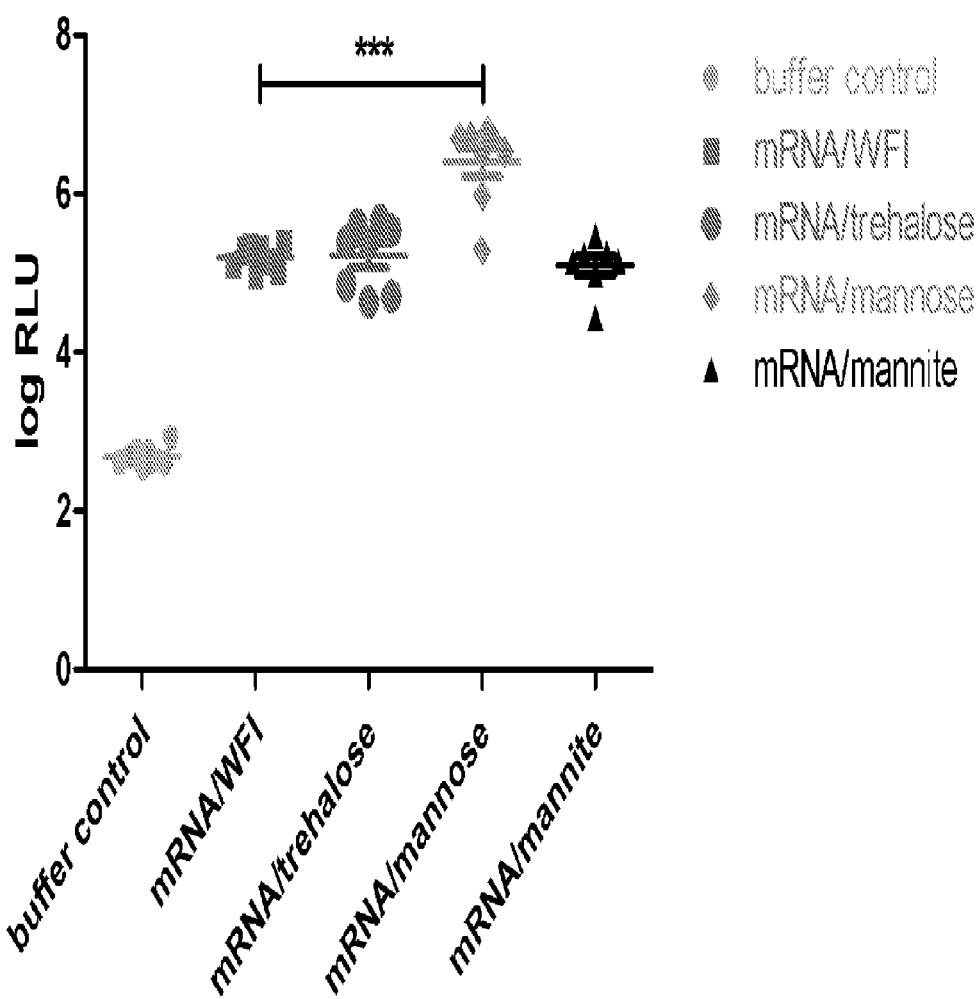
FIG. 1: shows the in vivo luciferase expression in balb/c mice 1) buffer control: Ringer-lactate 2) mRNA/WFI: mRNA coding for luciferase lyophilized in WFI (water for injection) and dissolved in salt containing solution 3) mRNA/trehalose: mRNA coding for luciferase lyophilized in WFI containing 5% trehalose and dissolved in salt containing solution 4) mRNA/mannose: mRNA coding for luciferase lyophilized in WFI containing 2.5% mannose and dissolved in salt containing solution 5) mRNA/mannite: mRNA coding for luciferase lyophilized in WFI containing 5% mannite and dissolved in salt containing solution.

the coding sequence encoding *Photinus pyralis* luciferase;
stabilizing sequences derived from alpha-globin-3'-UTR (muag (mutated alpha-globin-3'-UTR));
70×adenosine at the 3'-terminal end (poly-A-tail);
30×cytosine at the 3'-terminal end (poly-C-tail).

The ORF is indicated in italic letters, muag (mutated alpha-globin-3'-UTR is indicated with a dotted line, the poly-A-tail is underlined with a single line and the poly-C-tail is underlined with a double line.

FIG. 6: shows the mRNA sequence termed CAP-GgOva(GC)-muag-A70-C30 (SEQ ID NO: 2), coding for *Gallus gallus* ovalbumin, which exhibits a length of 1365 nucleotides. The mRNA sequence contains following sequence elements:

the coding sequence encoding *Gallus gallus* ovalbumin;
stabilizing sequences derived from alpha-globin-3'-UTR (muag (mutated alpha-globin-3'-UTR));
70×adenosine at the 3'-terminal end (poly-A-tail);
30×cytosine at the 3'-terminal end (poly-C-tail).

The ORF is indicated in italic letters, muag (mutated alpha-globin-3'-UTR is indicated with a dotted line, the poly-A-tail is underlined with a single line and the poly-C-tail is underlined with a double line.

DETAILED DESCRIPTION OF THE INVENTION

The present invention relates to (the use of) a solution containing at least one nucleic acid (sequence) and free mannose for lyophilization, transfection and/or injection, particularly of RNA and mRNA. The inventive solution exhibits a positive effect on stabilization of the nucleic acid (sequence) during lyophilization and storage but also leads to a considerable increase of the transfection efficiency of a nucleic acid. It thus also increases in vivo expression of a protein encoded by such a nucleic acid upon increased transfection rate. The present invention is furthermore directed to a method of lyophilization using the mannose-containing solution, to pharmaceutical compositions, vaccines, kits, first and second medical uses applying such a mannose-containing solution and/or a nucleic acid (sequence) lyophilized or resuspended with such a solution.

According to the first aspect, the present invention thus provides (the use of) a solution containing at least one nucleic acid (sequence) and (free) mannose for lyophilization, transfection and/or injection. In this context "free" mannose is preferably understood as a mannose, which is not covalently bound and/or conjugated, preferably not covalently bound and/or conjugated to the nucleic acid (sequence) to be lyophilized, transfected and/or injected. "Free" mannose may therefore comprise a free, non-covalently bound and/or unconjugated mannose, preferably with respect to the nucleic acid (sequence) to be lyophilized, transfected and/or injected.

In the context of the present invention, mannose is preferably a sugar monomer of the aldohexose series of carbohydrates. Mannose as defined herein typically has the molecular formula $C_6H_{12}C_6$, is also known under its IUPAC nomenclature as (2S,3S,4R,5R)-Pentahydroxyhexanal, (2R, 3R,4S,5S)-Pentahydroxyhexanal. It is preferably identified under CAS number 31103-86-3 and typically exhibits the following general structure:

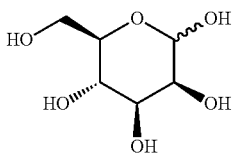 [SMILES: OC[C@H]1OC(O)[C@@H](O)[C@@H](O)[C@@H]1O]

Mannose is typically formed by the oxidation of mannitol. It can also be formed from D-glucose in the Lobry-de Bruyn-van Ekenstein transformation. Mannose as defined herein typically occurs in two diastereomeric isoforms, D-Mannose and L-Mannose (CAS numbers 3458-28-4 for D-mannose and 10030-80-5 for L-mannose). D-mannose is sold as a naturopathic remedy for urinary tract infections, and it is claimed to work through the disruption of adherence of bacteria in the urinary tract. D-Mannose and L-Mannose can be illustrated as the D and L straight-chain forms of mannose using Fischer projections according to the following structures:

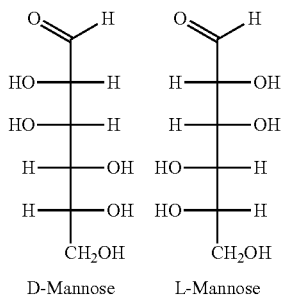

According to a particularly preferred aspect, mannose as used herein is a D-Mannose. D-Mannose may be depicted according to at least one of the D-Mannose isomers α-D-Mannofuranose, β-D-Mannofuranose, α-D-Mannopyranose and β-D-Mannopyranose as represented by following Haworth-structures:

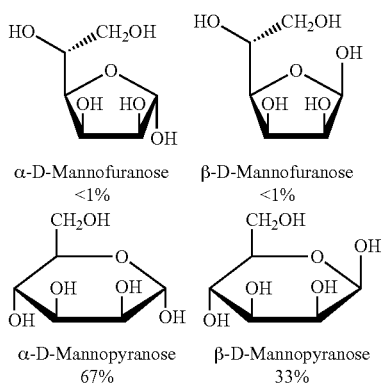

Typically, the occurrence of the different mannose isomers in nature significantly differs. D-Mannose forms anomers, wherein α-D-Mannofuranose occurs in a concentration/frequency of less than 1%, β-D-Mannofuranose in a concentration/frequency of less than 1%, α-D-Mannopyranose in a concentration/frequency of about 67% and β-D-Mannopyranose in a concentration/frequency of about 33%. Thus, D-Mannose may be selected more preferably from at least one, two, three or four of the anomers α-D-Mannofuranose, β-D-Mannofuranose, α-D-Mannopyranose and/or β-D-Mannopyranose. Most preferably, upon solubilization in an aqueous solution mannose typically forms the above anomers in an equilibrity reaction, typically in the above concentrations.

According to a particularly preferred aspect, mannose as used herein is selected from an anomeric mixture of D-Mannose, preferably an anomeric mixture comprising α-D-Mannofuranose, β-D-Mannofuranose, α-D-Mannopyranose and β-D-Mannopyranose, more preferably in the above concentrations/frequencies. Alternatively, but less preferred, mannose as used herein may be selected from L-mannose or a racemic mixture of D-Mannose and/or L-Mannose, wherein D-mannose preferably as described above. Such mixtures may be obtained e.g. by a non-selective synthesis of mannose, e.g. by non-selective oxidation of mannitol. An anomeric mixture may furthermore be obtained by solubilization of mannose in an aqueous solution, e.g. in water, WFI, or any buffer or solution as defined herein.

According to a more preferred aspect, mannose as used herein is typically present in the inventive solution for lyophilization, transfection and/or injection in a concentration of about 0.01 to about 10% (w/w), preferably in a concentration of about 0.01 to about 10% (w/w), more preferably in a concentration of about 0.1 to about 7.5% (w/w), even more preferably in a concentration of about 0.5 to about 5% (w/w), and most preferably in a concentration of about 1 to about 4% (w/w), e.g. a concentration of about 2 to about 4% (w/w), such as about 2.5% (w/w). Herein, a concentration of about 1% (w/w) mannose corresponds to a concentration of about 55,506 mM mannose. Any of the above and herein mentioned values and concentrations for mannose in % (w/w) may thus be calculated in mM on the above basis.

According to the above first embodiment, the present invention provides (use of) a solution containing at least one nucleic acid sequence and free mannose for lyophilization, transfection and/or injection of the at least one nucleic acid (sequence). Lyophilization, transfection and/or injection may be carried out in vivo, in vitro or ex vivo. In the context of the present invention, such a lyophilized nucleic acid (sequence) may be any suitable nucleic acid, selected e.g. from any (double-stranded or single-stranded) DNA, preferably, without being limited thereto, e.g. genomic DNA, single-stranded DNA molecules, double-stranded DNA molecules, coding DNA, DNA primers, DNA probes, immunostimulatory DNA, a (short) DNA oligonucleotide ((short) oligodesoxyribonucleotides), or may be selected e.g. from any PNA (peptide nucleic acid) or may be selected e.g. from any (double-stranded or single-stranded) RNA, preferably, without being limited thereto, a (short) RNA oligonucleotide ((short) oligoribonucleotide), a coding RNA, a messenger RNA (mRNA), an immunostimulatory RNA, a siRNA, an antisense RNA, a micro RNA or riboswitches, ribozymes or aptamers; etc. The nucleic acid (sequence) of the inventive solution for lyophilization, transfection and/or injection may also be a ribosomal RNA (rRNA), a transfer RNA (tRNA), a messenger RNA (mRNA), or a viral RNA (vRNA). Preferably, the nucleic acid (sequence) of the inventive solution for lyophilization, transfection and/or injection is an RNA. More preferably, the nucleic acid (sequence) of the inventive solution for lyophilization, transfection and/or injection may be a (linear) single-stranded RNA, even more preferably an mRNA. In the context of the present invention, an mRNA is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. an RNA which carries the coding sequences of one, two or more proteins or peptides. Such coding sequences in di-, or even multicistronic mRNA may be separated by at least one IRES sequence, e.g. as defined herein.

Furthermore, the nucleic acid (sequence) of the inventive solution for lyophilization, transfection and/or injection may be a single- or a double-stranded nucleic acid (molecule) (which may also be regarded as a nucleic acid (molecule) due to non-covalent association of two single-stranded nucleic acid(s) (molecules)) or a partially double-stranded or partially single stranded nucleic acid, which are at least partially self complementary (both of these partially double-stranded or partially single stranded nucleic acid molecules are typically formed by a longer and a shorter single-stranded nucleic acid molecule or by two single stranded nucleic acid molecules, which are about equal in length, wherein one single-stranded nucleic acid molecule is in part complementary to the other single-stranded nucleic acid molecules molecule and both thus form a double-stranded nucleic acid molecules molecule in this region, i.e. a partially double-stranded or partially single stranded nucleic acid molecules). Preferably, the nucleic acid (sequence) of the inventive solution for lyophilization, transfection and/or injection may be a single-stranded nucleic acid molecule. Furthermore, the nucleic acid (sequence) of the inventive solution for lyophilization, transfection and/or injection may be a circular or linear nucleic acid molecule, preferably a linear nucleic acid molecule.

According to one alternative, the nucleic acid (sequence) of the inventive solution for lyophilization, transfection and/or injection may be a coding nucleic acid, e.g. a DNA or RNA. Such a coding DNA or RNA may be any DNA or RNA as defined above. Preferably, such a coding DNA or RNA may be a single- or a double-stranded DNA or RNA, more preferably a single-stranded DNA or RNA, and/or a circular or linear DNA or RNA, more preferably a linear DNA or RNA. Even more preferably, the coding DNA or RNA may be a (linear) single-stranded DNA or RNA. Most preferably, the nucleic acid (sequence) of the inventive solution for lyophilization, transfection and/or injection may be a ((linear) single-stranded) messenger RNA (mRNA). Such an mRNA may occur as a mono-, di-, or even multicistronic RNA, i.e. an RNA which carries the coding sequences of one, two or more proteins or peptides. Such coding sequences in di-, or even multicistronic mRNA may be separated by at least one IRES sequence, e.g. as defined herein.

The nucleic acid (sequence) of the inventive solution for lyophilization, transfection and/or injection may encode a protein or a peptide, which may be selected, without being restricted thereto, e.g. from therapeutically active proteins or peptides, from antigens, e.g. tumor antigens, pathogenic antigens (e.g. selected from pathogenic proteins as defined herein or from animal antigens, viral antigens, protozoal antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application, wherein the coding DNA or RNA may be transported into a cell, a tissue or an organism and the protein may be expressed subsequently in this cell, tissue or organism.

a) Therapeutically Active Proteins

In this context, therapeutically active proteins may be encoded by the nucleic acid (sequence) of the inventive solution for lyophilization, transfection and/or injection. These may be selected from any naturally occurring recombinant or isolated protein known to a skilled person from the prior art. Without being restricted thereto therapeutically active proteins may comprise proteins, capable of stimulating or inhibiting the signal transduction in the cell, e.g. cytokines, antibodies, etc. Therapeutically active proteins may thus comprise cytokines of class I of the family of cytokines, having 4 positionally conserved cysteine residues (CCCC) and comprising a conserved sequence motif Trp-Ser-X-Trp-Ser (WSXWS), wherein X is a non-conserved amino acid. Cytokines of class I of the family of cytokines comprise the GM-CSF subfamily, e.g. IL-3, IL-5, GM-CSF, the IL-6-subfamily, e.g. IL-6, IL-11, IL-12, or the IL-2-subfamily, e.g. IL-2, IL-4, IL-7, IL-9, IL-15, etc., or the cytokines IL-1alpha, IL-1beta, IL-10 etc. Therapeutically active proteins may also comprise cytokines of class II of the family of cytokines, which also comprise 4 positionally conserved cystein residues (CCCC), but no conserved sequence motif Trp-Ser-X-Trp-Ser (WSXWS). Cytokines of class II of the family of cytokines comprise e.g. IFN-alpha, IFN-beta, IFN-gamma, etc. Therapeutically active proteins may additionally comprise cytokines of the family of tumor necrose factors, e.g. TNF-alpha, TNF-beta, etc., or cytokines of the family of chemokines, which comprise 7 transmembrane helices and interact with G-protein, e.g. IL-8, MIP-1, RANTES, CCR5, CXR4, etc., or cytokine specific receptors, such as TNF-RI, TNF-RII, CD40, OX40 (CD134), Fas, etc.

Therapeutically active proteins, which may be encoded by the nucleic acid (sequence) of the inventive solution for lyophilization, transfection and/or injection may also be selected from any of the proteins given in the following: 0ATL3, 0FC3, 0PA3, 0PD2, 4-1BBL, 5T4, 6Ckine, 707-AP, 9D7, A2M, AA, AAAS, AACT, AASS, ABAT, ABCA1, ABCA4, ABCB1, ABCB11, ABCB2, ABCB4, ABCB7, ABCC2, ABCC6, ABCC8, ABCD1, ABCD3, ABCG5, ABCG8, ABL1, ABO, ABR ACAA1, ACACA, ACADL, ACADM, ACADS, ACADVL, ACAT1, ACCPN, ACE, ACHE, ACHM3, ACHM1, ACLS, ACP1, ACTA1, ACTC, ACTN4, ACVRL1, AD2, ADA, ADAMTS13, ADAMTS2, ADFN, ADH1B, ADH1C, ADLDH3A2, ADRB2, ADRB3, ADSL, AEZ, AFA, AFD1, AFP, AGA, AGL, AGMX2, AGPS, AGS1, AGT, AGTR1, AGXT, AH02, AHCY, AHDS, AHHR, AHSG, AIC, AIED, AIH2, AIH3, AIM-2, AIPL1, AIRE, AK1, ALAD, ALAS2, ALB, HPG1, ALDH2, ALDH3A2, ALDH4A1, ALDH5A1, ALDH1A1, ALDOA, ALDOB, ALMS1, ALPL, ALPP, ALS2, ALX4, AMACR, AMBP, AMCD, AMCD1, AMCN, AMELX, AMELY, AMGL, AMH, AMHR2, AMPD3, AMPD1, AMT, ANC, ANCR, ANK1, ANOP1, AOM, APOA4, APOC2, APOC3, AP3B1, APC, aPKC, APOA2, APOA1, APOB, APOC3, APOC2, APOE, APOH, APP, APRT, APS1, AQP2, AR, ARAF1, ARG1, ARHGEF12, ARMET, ARSA, ARSB, ARSC2, ARSE, ART-4, ARTC1/m, ARTS, ARVD1, ARX, AS, ASAH, ASAT, ASD1, ASL, ASMD, ASMT, ASNS, ASPA, ASS, ASSP2, ASSP5, ASSP6, AT3, ATD, ATHS, ATM, ATP2A1, ATP2A2, ATP2C1, ATP6B1, ATP7A, ATP7B, ATP8B1, ATPSK2, ATRX, ATXN1, ATXN2, ATXN3, AUTS1, AVMD, AVP, AVPR2, AVSD1, AXIN1, AXIN2, AZF2, B2M, B4GALT7, B7H4, BAGE, BAGE-1, BAX, BBS2, BBS3, BBS4, BCA225, BCAA, BCH, BCHE, BCKDHA, BCKDHB, BCL10, BCL2, BCL3, BCL5, BCL6, BCPM, BCR, BCR/ABL, BDC, BDE, BDMF, BDMR, BEST1, beta-Catenin/m, BF, BFHD, BFIC, BFLS, BFSP2, BGLAP, BGN, BHD, BHR1, BING-4, BIRC5, BJS, BLM, BLMH, BLNK, BMPR2, BPGM, BRAF, BRCA1, BRCA1/m, BRCA2, BRCA2/m, BRCD2, BRCD1, BRDT, BSCL, BSCL2, BTAA, BTD, BTK, BUB1, BWS, BZX, C0LZA 1, C0L6A1, C1NH, C1QA, C1QB, C1QG, C1S, C2, C3, C4A, C4B, C5, C6, C7, C7orf2, C8A, C8B, C9, CA125, CA15-3/CA 27-29, CA195, CA19-9, CA72-4, CA2, CA242, CA50, CABYR, CACD, CACNA2D1, CACNA1A, CACNA1F, CACNA1S, CACNB2, CACNB4, CAGE, CA1, CALB3, CALCA, CALCR, CALM, CALR, CAM43, CAMEL, CAP-1, CAPN3, CARD15, CASP-5/m, CASP-8, CASP-8/m, CASR, CAT, CATM, CAV3, CB1, CBBM, CBS, CCA1, CCAL2, CCAL1, CCAT, CCL-1, CCL-11, CCL-12, CCL-13, CCL-14, CCL-15, CCL-16, CCL-17, CCL-18, CCL-19, CCL-2, CCL-20, CCL-21, CCL-22, CCL-23, CCL-24, CCL-25, CCL-27, CCL-3, CCL-4, CCL-5, CCL-7, CCL-8, CCM1, CCNB1, CCND1, CCO, CCR2, CCR5, CCT, CCV, CCZS, CD1, CD19, CD20, CD22, CD25, CD27, CD27L, cD3, CD30, CD30, CD30L, CD33, CD36, CD3E, CD3G, CD3Z, CD4, CD40, CD40L, CD44, CD44v, CD44v6, CD52, CD55, CD56, CD59, CD80, CD86, CDAN1, CDAN2, CDAN3, CDC27, CDC27/m, CDC2L1, CDH1, CDK4, CDK4/m, CDKN1C, CDKN2A, CDKN2A/m, CDKN1A, CDKN1C, CDL1, CDPD1, CDR1, CEA, CEACAM1, CEACAM5, CECR, CECR9, CEPA, CETP, CFNS, CFTR, CGF1, CHAC, CHED2, CHED1, CHEK2, CHM, CHML, CHR39c, CHRNA4, CHRNA1, CHRNB1, CHRNE, CHS, CHS1, CHST6, CHX10, CIAS1, CIDX, CKN1, CLA2, CLA3, CLA1, CLCA2, CLCN1, CLCN5, CLCNKB, CLDN16, CLP, CLN2, CLN3, CLN4, CLN5, CLN6, CLN8, C1QA, C1QB, C1QG, C1R, CLS, CMCWTD, CMDJ, CMD1A, CMD1B, CMH2, MH3, CMH6, CMKBR2, CMKBR5, CML28, CML66, CMM, CMT2B, CMT2D, CMT4A, CMT1A, CMTX2, CMTX3, C-MYC, CNA1, CND, CNGA3, CNGA1, CNGB3, CNSN, CNTF, COA-1/m, COCH, COD2, COD1, COH1, COL10A, COL2A2, COL11A2, COL17A1, COL1A1, COL1A2, COL2A1, COL3A1, COL4A3, COL4A4, COL4A5, COL4A6, COL5A1, COL5A2, COL6A1, COL6A2, COL6A3, COL7A1, COL8A2, COL9A2, COL9A3, COL11A1, COL1A2, COL23A1, COL1A1, COLQ, COMP, COMT, CORD5, CORD1, COX10, COX-2, CP, CPB2, CPO, CPP, CPS1, CPT2, CPT1A, CPX, CRAT, CRB1, CRBM, CREBBP, CRH, CRHBP, CRS, CRV, CRX, CRYAB, CRYBA1, CRYBB2, CRYGA, CRYGC, CRYGD, CSA, CSE, CSF1R, CSF2RA, CSF2RB, CSF3R, CSF1R, CST3, CSTB, CT, CT7, CT-9/BRD6, CTAA1, CTACK, CTEN, CTH, CTHM, CTLA4, CTM, CTNNB1, CTNS, CTPA, CTSB, CTSC, CTSK, CTSL, CTS1, CUBN, CVD1, CX3CL1, CXCL1, CXCL10, CXCL11, CXCL12, CXCL13, CXCL16, CXCL2, CXCL3, CXCL4, CXCL5, CXCL6, CXCL7, CXCL8, CXCL9, CYB5, CYBA, CYBB, CYBB5, CYFRA 21-1, CYLD, CYLD1, CYMD, CYP11B1, CYP11B2, CYP17, CYP17A1, CYP19, CYP19A1, CYP1A2, CYP1B1, CYP21A2, CYP27A1, CYP27B1, CYP2A6, CYP2C, CYP2C19, CYP2C9, CYP2D, CYP2D6, CYP2D7P1, CYP3A4, CYP7B1, CYPB1, CYP11B1, CYP1A1, CYP1B1, CYRAA, D40, DAD1, DAM, DAM-10/MAGE-B1, DAM-6/MAGE-B2, DAX1, DAZ, DBA, DBH, DBI, DBT, DCC, DC-CK1, DCK, DCR, DCX, DDB 1, DDB2, DDIT3, DDU, DECR1, DEK-CAN, DEM, DES, DF, DFN2, DFN4, DFN6, DFNA4, DFNA5, DFNB5, DGCR, DHCR7, DHFR, DHOF, DHS, DIA1, DIAPH2, DIAPH1, DIH1, DIO1, DISC1, DKC1, DLAT, DLD, DLL3, DLX3, DMBT1, DMD, DM1, DMPK, DMWD, DNAI1, DNASE1, DNMT3B, DPEP1, DPYD, DPYS, DRD2, DRD4, DRPLA, DSCR1, DSG1, DSP, DSPP, DSS, DTDP2, DTR, DURS1, DWS, DYS, DYSF, DYT2, DYT3, DYT4, DYT2, DYT1, DYX1, EBAF, EBM, EBNA, EBP, EBR3, EBS1, ECA1, ECB2, ECE1, ECGF1, ECT, ED2, ED4, EDA, EDAR, ECA1, EDN3, EDNRB, EEC1, EEF1A1L14, EEGV1, EFEMP1, EFTUD2/m, EGFR, EGFR/Her1, EG1, EGR2, EIF2AK3, eIF4G, EKV, E1 IS, ELA2, ELF2, ELF2M, ELK1, ELN, ELONG, EMD, EML1, EMMPRIN, EMX2, ENA-78, ENAM, END3, ENG, ENO1, ENPP1, ENUR2, ENUR1, EOS, EP300, EPB41, EPB42, EPCAM, EPD, EphA1, EphA2, EphA3, EphrinA2, EphrinA3, EPHX1, EPM2A, EPO, EPOR, EPX, ERBB2, ERCC2 ERCC3, ERCC4, ERCC5, ERCC6, ERVR, ESR1, ETFA, ETFB, ETFDH, ETM1, ETV6-AML1, ETV1, EVC, EVR2, EVR1, EWSR1, EXT2, EXT3, EXT1, EYA1, EYCL2, EYCL3, EYCL1, EZH2, F10, F11, F12, F13A1, F13B, F2, F5, F5F8D, F7, F8, F8C, F9, FABP2, FACL6, FAH, FANCA, FANCB, FANCC, FANCD2, FANCF, FasL, FBN2, FBN1, FBP1, FCG3RA, FCGR2A, FCGR2B, FCGR3A, FCHL, FCMD, FCP1, FDPSL5, FECH, FEO, FEOM1, FES, FGA, FGB, FGD1, FGF2, FGF23, FGF5, FGFR2, FGFR3, FGFR1, FGG, FGS1, FH, FIC1, FIH, F2, FKBP6, FLNA, FLT4, FMO3, FMO4, FMR2, FMR1, FN, FN1/m, FOXC1, FOXE1, FOXL2, FOXO1A, FPDMM, FPF, Fra-1, FRAXF, FRDA, FSHB, FSHMD1A, FSHR, FTH1, FTHL17, FTL, FTZF1, FUCA1, FUT2, FUT6, FUT1, FY, G250, G250/CAIX, G6PC, G6PD, G6PT1, G6PT2, GAA, GABRA3, GAGE-1, GAGE-2, GAGE-3, GAGE-4, GAGE-5, GAGE-6, GAGE-7b, GAGE-8, GALC, GALE, GALK1, GALNS, GALT, GAMT, GAN, GAST, GASTRIN17, GATA3, GATA, GBA, GBE, GC, GCDH, GCGR, GCH1, GCK, GCP-2, GCS1, G-CSF, GCSH, GCSL, GCY, GDEP, GDF5, GDI1, GDNF, GDXY, GFAP, GFND, GGCX, GGT1, GH2, GH1, GHR, GHRHR, GHS, GIF, GINGF, GIP, GJA3, GJA8, GJB2, GJB3, GJB6, GJB1, GK, GLA, GLB, GLB1, GLC3B, GLC1B, GLC1C, GLDC, GLI3, GLP1, GLRA1, GLUD1, GM1 (fuc-GM1), GM2A, GM-CSF, GMPR, GNAI2, GNAS, GNAT1, GNB3, GNE, GNPAT, GNRH, GNRH1, GNRHR, GNS, GnT-V, gp100, GP1BA, GP1BB, GP9, GPC3, GPD2, GPDS1, GP1, GP1BA, GPN1LW, GPNMB/m, GPSC, GPX1, GRHPR, GRK1, GROα, GROβ, GROγ, GRPR, GSE, GSM1, GSN, GSR, GSS, GTD, GTS, GUCA1A, GUCY2D, GULOP, GUSB, GUSM, GUST, GYPA, GYPC, GYS1, GYS2, HOKPP2, HOMG2, HADHA, HADHB, HAGE, HAGH, HAL, HAST-2, HB 1, HBA2, HBA1, HBB, HBBP1, HBD, HBE1, HBG2, HBG1, HBHR, HBP1, HBQ1, HBZ, HBZP, HCA, HCC-1, HCC-4, HCF2, HCG, HCL2, HCL1, HCR, HCVS, HD, HPN, HER2, HER2/NEU, HER3, HERV-K-MEL, HESX1, HEXA, HEXB, HF1, HFE, HF1, HGD, HHC2, HHC3, HHG, HK1 HLA-A, HLA-A*0201-R170I, HLA-A11/m, HLA-A2/m, HLA-DPB1 HLA-DRA, HLCS, HLXB9, HMBS, HMGA2, HMGCL, HMI, HMN2, HMOX1, HMS1 HMW-MAA, HND, HNE, HNF4A, HOAC, HOMEOBOX NKX 3.1, HOM-TES-14/SCP-1, HOM-TES-85, HOXA1 HOXD13, HP, HPC1, HPD, HPE2, HPE1, HPFH, HPFH2, HPRT1, HPS1, HPT, HPV-E6, HPV-E7, HR, HRAS, HRD, HRG, HRPT2, HRPT1, HRX, HSD11B2, HSD17B3, HSD17B4, HSD3B2, HSD3B3, HSN1, HSP70-2M, HSPG2, HST-2, HTC2, HTC1, hTERT, HTN3, HTR2c, HVBS6, HVBS1, HVEC, HV1S, HYAL1, HYR, I-309, IAB, IBGC1, IBM2, ICAM1, ICAM3, iCE, ICHQ, ICR5, ICR1, ICS 1, IDDM2, IDDM1, IDS, IDUA, IF, ☐IFNa/b, ☐IFNGR1, IGAD1, IGER, IGF-1R, IGF2R, IGF1, IGH, IGHC, IGHG2, IGHG1, IGHM, IGHR, IGKC, IHG1, IHH, IKBKG, IL, IL-1 RA, IL10, IL-11, IL12, IL12RB1, IL13, IL-13Rα2, IL-15, IL-16, IL-17, IL18, IL-1a, IL-1α, IL-1b, IL-1β, IL1RAPL1, IL2, IL24, IL-2R, IL2RA, IL2RG, IL3, IL3RA, IL4, IL4R, IL4R, IL-5, IL6, IL-7, IL7R, IL-8, IL-9, Immature laminin receptor, IMMP2L, INDX, INFGR1, INFGR2, INFα, IFN☐, INFγ, INS, INSR, INVS, IP-10, IP2, IPF1, IP1, IRF6, IRS1, ISCW, ITGA2, ITGA2B, ITGA6, ITGA7, ITGB2, ITGB3, ITGB4, ITIH1, ITM2B, IV, IVD, JAG1, JAK3, JBS, JBTS1, JMS, JPD, KAL1, KAL2, KAL1, KLK2, KLK4, KCNA1, KCNE2, KCNE1, KCNH2, KCNJ1, KCNJ2, KCNJ1, KCNQ2, KCNQ3, KCNQ4, KCNQ1, KCS, KERA, KFM, KFS, KFSD, KHK, ki-67, KIAA0020, KIAA0205, KIAA0205/m, KIF1B, KIT, KK-LC-1, KLK3, KLKB1, KM-HN-1, KMS, KNG, KNO, K-RAS/m, KRAS2, KREV1, KRT1, KRT10, KRT12, KRT13, KRT14, KRT14L1, KRT14L2, KRT14L3, KRT16, KRT16L1, KRT16L2, KRT17, KRT18, KRT2A, KRT3, KRT4, KRT5, KRT6A, KRT6B, KRT9, KRTHB1, KRTHB6, KRT1, KSA, KSS, KWE, KYNU, L0H19CR1, L1CAM, LAGE, LAGE-1, LALL, LAMA2, LAMA3, LAMB3, LAMB1, LAMC2, LAMP2, LAP, LCA5, LCAT, LCCS, LCCS1, LCFS2, LCS1, LCT, LDHA, LDHB, LDHC, LDLR, LDLR/FUT, LEP, LEWISY, LGCR, LGGF-PBP, LGI1, LGMD2H, LGMD1A, LGMD1B, LHB, LHCGR, LHON, LHRH, LHX3, LIF, LIG1, LIMM, LIMP2, LIPA, LIPA, LIPB, LIPC, LIVIN, LICAM, LMAN1, LMNA, LMX1B, LOLR, LOR, LOX, LPA, LPL, LPP, LQT4, LRP5, LRS 1, LSFC, LT-β, LTBP2, LTC4S, LYL1, XCL1, LYZ, M344, MA50, MAA, MADH4, MAFD2, MAFD1, MAGE, MAGE-A1, MAGE-A10, MAGE-A12, MAGE-A2, MAGE-A3, MAGE-A4, MAGE-A6, MAGE-A9, MAGEB1, MAGE-B10, MAGE-B16, MAGE-B17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2, MGB1, MGB2, MAN2A1, MAN2B1, MANBA, MANBB, MAOA, MAOB, MAPK81P1, MAPT, MART-1, MART-2, MART2/m, MAT1A, MBL2, MBP, MBS1, MC1R, MC2R, MC4R, MCC, MCCC2, MCCC1, MCDR1, MCF2, MCKD, MCL1, MC1R, MCOLN1, MCOP, MCOR, MCP-1, MCP-2, MCP-3, MCP-4, MCPH2, MCPH1, MCS, M-CSF, MDB, MDCR, MDM2, MDRV, MDS 1, ME1, ME1/m, ME2, ME20, ME3, MEAX, MEB, MEC CCL-28, MECP2, MEFV, MELANA, MELAS, MEN1 MSLN, MET, MF4, MG50, MG50/PXDN, MGAT2, MGAT5, MGC1 MGCR, MGCT, MGI, MGP, MHC2TA, MHS2, MHS4, MIC2, MIC5, MIDI, MIF, MIP, MIP-5/HCC-2, MITF, MJD, MKI67, MKKS, MKS1, MLH1, MLL, MLLT2, MLLT3, MLLT7, MLLT1, MLS, MLYCD, MMA1a, MMP 11, MMVP1, MN/CA IX-Antigen, MNG1, MN1, MOC31, MOCS2, MOCS1, MOG, MORC, MOS, MOV18, MPD1, MPE, MPFD, MP1, MPIF-1, MPL, MPO, MPS3C, MPZ, MRE11A, MROS, MRP1, MRP2, MRP3, MRSD, MRX14, MRX2, MRX20, MRX3, MRX40, MRXA, MRX1, MS, MS4A2, MSD, MSH2, MSH3, MSH6, MSS, MSSE, MSX2, MSX1, MTATP6, MTC03, MTCO1, MTCYB, MTHFR, MTM1, MTMR2, MTND2, MTND4, MTND5, MTND6, MTND1, MTP, MTR, MTRNR2, MTRNR1, MTRR, MTTE, MTTG, MTTI, MTTK, MTTL2, MTTL1, MTTN, MTTP, MTTS1, MUC1, MUC2, MUC4, MUC5AC, MUM-1, MUM-1/m, MUM-2, MUM-2/m, MUM-3, MUM-3/m, MUT, mutant p21 ras, MUTYH, MVK, MX2, MX11, MY05A, MYB, MYBPC3, MYC, MYCL2, MYH6, MYH7, MYL2, MYL3, MYMY, MYO15A, MYO1G, MYO5A, MYO7A, MYOC, Myosin/m, MYP2, MYP1, NA88-A, N-acetylglucosaminyltransferase-V, NAGA, NAGLU, NAMSD, NAPB, NAT2, NAT, NBIA1, NBS1, NCAM, NCF2, NCF1, NDN, NDP, NDUFS4, NDUFS7, NDUFS8, NDUFV1, NDUFV2, NEB, NEFH, NEM1, Neo-PAP, neo-PAP/m, NEU1, NEUROD1, NF2, NF1, NFYC/m, NGEP, NHS, NKS1, NKX2E, NM, NME1, NMP22, NMTC, NODAL, NOG, NOS3, NOTCH3, NOTCH1, NP, NPC2, NPC1, NPHL2, NPHP1, NPHS2, NPHS1, NPM/ALK, NPPA, NQO1, NR2E3, NR3C1, NR3C2, NRAS, NRAS/m, NRL, NROB1, NRTN, NSE, NSX, NTRK1, NUMA1, NXF2, NY-CO1, NY-ESO1, NY-ESO-B, NY-LU-12, ALDOA, NYS2, NYS4, NY-SAR-35, NYS1, NYX, OA3, OA1, OAP, OASD, OAT, OCA1, OCA2, OCD1, OCRL, OCRL1, OCT, ODDD, ODT1, OFC1, OFD1, OGDH, OGT, OGT/m, OPA2, OPA1, OPD1, OPEM, OPG, OPN, OPN1LW, OPN1MW, OPN1SW, OPPG, OPTB1, TTD, ORM1, ORP1, OS-9, OS-9/m, OSM LIF, OTC, OTOF, OTSC1, OXCT1, OYTES1, P15, P190 MINOR BCR-ABL, P2RY12, P3, P16, P40, P4HB, P-501, P53, P53/m, P97, PABPN1, PAFAHIB1, PAFAHIP1, PAGE-4, PAGE-5, PAH, PAI-1, PAI-2, PAK3, PAP, PAPPA, PARK2, PART-1, PATE, PAX2, PAX3, PAX6, PAX7, PAX8, PAX9, PBCA, PBCRA1, PBT, PBX1, PBXP1, PC, PCBD, PCCA, PCCB, PCK2, PCK1, PCLD, PCOS1, PCSK1, PDB1, PDCN, PDE6A, PDE6B, PDEF, PDGFB, PDGFR, PDGFRL, PDHA1, PDR, PDX1, PECAM1, PEE1, PEO1, PEPD, PEX10, PEX12, PEX13, PEX3, PEX5, PEX6, PEX7, PEX1, PF4, PFB1, PFC, PFKFB1, PFKM, PGAM2, PGD, PGK1, PGKIP1, PGL2, PGR, PGS, PHA2A, PHB, PHEX, PHGDH, PHKA2, PHKA1, PHKB, PHKG2, PHP, PHYH, PI, PI3, PIGA, PIM1-KINASE, PIN1, PIP5K1B, PITX2, PITX3, PKD2, PKD3, PKD1, PKDTS, PKHD1, PKLR, PKP1, PKU1, PLA2G2A, PLA2G7, PLAT, PLEC1, PLG, PL1, PLOD, PLP1, PMEL17, PML, PML/RARα, PMM2, PMP22, PMS2, PMS1, PNKD, PNLIP, POF1, POLA, POLH, POMC, PON2, PON1, PORC, POTE, POU1F1, POU3F4, POU4F3, POUIF1, PPAC, PPARG, PPCD, PPGB, PPH1, PPKB, PPMX, PPDX, PPPIR3A, PPP2R2B, PPT1, PRAME, PRB, PRB3, PRCA1, PRCC, PRD, PRDX5/m, PRF1, PRG4, PRKAR1A, PRKCA, PRKDC, PRKWNK4, PRNP, PROC, PRODH, PROM1, PROP1, PROS1, PRST, PRP8, PRPF31, PRPF8, PRPH2, PRPS2, PRPS1, PRS, PRSS7, PRSS1, PRTN3, PRX, PSA, PSAP, PSCA, PSEN2, PSEN1, PSG1, PSGR, PSM, PSMA, PSORS1, PTC, PTCH, PTCH1, PTCH2, PTEN, PTGS1, PTH, PTHR1, PTLAH, PTOS1, PTPN12, PTPN11, PTPRK, PTPRK/m, PTS, PUJO, PVR, PVRL1, PWCR, PXE, PXMP3, PXR1, PYGL, PYGM, QDPR, RAB27A, RAD54B, RAD54L, RAG2, RAGE, RAGE-1, RAG1, RAP1, RARA, RASA1, RBAF600/m, RB1, RBP4, RBP4, RBS, RCA1, RCAS1, RCCP2, RCD1, RCV1, RDH5, RDPA, RDS, RECQL2, RECQL3, RECQL4, REG1A, REHOBE, REN, RENBP, RENS1, RET, RFX5, RFXANK, RFXAP, RGR, RHAG, RHAMM/CD168, RHD, RHO, Rip-1, RLBP1, RLN2, RLN1, RLS, RMD1, RMRP, ROM1, ROR2, RP, RP1, RP14, RP17, RP2, RP6, RP9, RPD1, RPE65, RPGR, RPGR1P1, RP1, RP10, RPS19, RPS2, RPS4X, RPS4Y, RPS6KA3, RRAS2, RS1, RSN, RSS, RU1, RU2, RUNX2, RUNX1, RS, RYR1, S-100, SAA1, SACS, SAG, SAGE, SALL1, SARDH, SART1, SART2, SART3, SAS, SAX1, SCA2, SCA4, SCA5, SCAT, SCA8, SCA1, SCC, SCCD, SCF, SCLC1, SCN1A, SCN1B, SCN4A, SCN5A, SCNN1A, SCNN1B, SCNN1G, SCO2, SCP1, SCZD2, SCZD3, SCZD4, SCZD5, SCZD6, SCZD1, SDF-1α/β, SDHA, SDHD, SDYS, SEDL, SERPENA7, SERPINA3, SERPINA6, SERPINA1, SERPINC1, SERPIND1, SERPINE1, SERPINF2, SERPING1, SERPINC1, SFTPA1, SFTPB, SFTPC, SFTPD, SGCA, SGCB, SGCD, SGCE, SGM1, SGSH, SGY-1, SH2D1A, SHBG, SHFM2, SHFM3, SHFM1, SHH, SHOX, S1, SIAL, SIALYL LEWISX, SIASD, S11, SIM1, SIRT2/m, SIX3, SJS1, SKP2, SLCIOA2, SLC12A1, SLC12A3, SLC17A5, SLC19A2, SLC22A1L, SLC22A5, SLC25A13, SLC25A15, SLC25A20, SLC25A4, SLC25A5, SLC25A6, SLC26A2, SLC26A3, SLC26A4, SLC2A1, SLC2A2, SLC2A4, SLC3A1, SLC4A1, SLC4A4, SLC5A1, SLC5A5, SLC6A2, SLC6A3, SLC6A4, SLC7A7, SLC7A9, SLC11A1, SLOS, SMA, SMAD1, SMAL, SMARCB1, SMAX2, SMCR, SMCY, SM1, SMN2, SMN1, SMPD1, SNCA, SNRPN, SOD2, SOD3, SOD1, SOS1, SOST, SOX9, SOX10, Sp17, SPANXC, SPG23, SPG3A, SPG4, SPG5A, SPG5B, SPG6, SPG7, SPINK1, SPINK5, SPPK, SPPM, SPSMA, SPTA1, SPTB, SPTLC1, SRC, SRD5A2, SRPX, SRS, SRY, βhCG, SSTR2, SSX1, SSX2 (HOM-MEL-40/SSX2), SSX4, ST8, STAMP-1, STAR, STARP1, STATH, STEAP, STK2, STK11, STn/KLH, STO, STOM, STS, SUOX, SURF1, SURVIVIN-2B, SYCP1, SYM1, SYN1, SYNS1, SYP, SYT/SSX, SYT-SSX-1, SYT-SSX-2, TA-90, TAAL6, TACSTD1, TACSTD2, TAG72, TAF7L, TAF1, TAGE, TAG-72, TAL1, TAM, TAP2, TAP1, TAPVR1, TARC, TARP, TAT, TAZ, TBP, TBX22, TBX3, TBX5, TBXA2R, TBXAS1, TCAP, TCF2, TCF1, TCIRG1, TCL2, TCL4, TCL1A, TCN2, TCOF1, TCR, TCRA, TDD, TDFA, TDRD1, TECK, TECTA, TEK, TEL/AML1, TELAB1, TEX15, TF, TFAP2B, TFE3, TFR2, TG, TGFA, TGF-β, TGFB1, TGFB1, TGFBR2, TGFBRE, TGFβ, TGFβRII, TG1F, TGM-4, TGM1, TH, THAS, THBD, THC, THC2, THM, THPO, THRA, THRB, TIMM8A, TIMP2, TIMP3, TIMP1, TITF1, TKCR, TKT, TLP, TLR1, TLR10, TLR2, TLR3, TLR4, TLR4, TLR5, TLR6, TLR7, TLR8, TLR9, TLX1, TM4SF1, TM4SF2, TMC1, TMD, TMIP, TNDM, TNF, TNFRSF11A, TNFRSF1A, TNFRSF6, TNFSF5, TNFSF6, TNFαt, TNFβ, TNNI3, TNNT2, TOC, TOP2A, TOP1, TP53, TP63, TPA, TPBG, TP1, TP1/m, TPI1, TPM3, TPM1, TPMT, TPO, TPS, TPTA, TRA, TRAG3, TRAPPC2, TRC8, TREH, TRG, TRH, TRIM32, TRIM37, TRP1, TRP2, TRP-2/6b, TRP-2/INT2, Trp-p8, TRPS1, TS, TSC2, TSC3, TSC1, TSG101, TSHB, TSHR, TSP-180, TST, TTGA2B, TTN, TTPA, TTR, TU M2-PK, TULP1, TWIST, TYH, TYR, TYROBP, TYROBP, TYRP1, TYS, UBE2A, UBE3A, UBE1, UCHL1, UFS, UGT1A, ULR, UMPK, UMPS, UOX, UPA, UQCRC1, URO5, UROD, UPK1B, UROS, USH2A, USH3A, USH1A, USH1C, USP9Y, UV24, VBCH, VCF, VDI, VDR, VEGF, VEGFR-2, VEGFR-1, VEGFR-2/FLK-1, VHL, VIM, VMD2, VMD1, VMGLOM, VNEZ, VNF, VP, VRN1, VWF, VWS, WAS, WBS2, WFS2, WFS1, WHCR, WHN, WISP3, WMS, WRN, WS2A, WS2B, WSN, WSS, WT2, WT3, WT1, WTS, WWS, XAGE, XDH, XIC, XIST, XK, XM, XPA, XPC, XRCC9, XS, ZAP70, ZFHX1B, ZFX, ZFY, ZIC2, ZIC3, ZNF145, ZNF261, ZNF35, ZNF41, ZNF6, ZNF198, ZWS1.

Therapeutically active proteins, which may be encoded by the nucleic acid (sequence) of the inventive solution for lyophilization, transfection and/or injection may further be selected from apoptotic factors or apoptosis related proteins including AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, transglutaminase, etc.

A therapeutically active protein, which may be encoded by the nucleic acid (sequence) of the inventive solution for lyophilization, transfection and/or injection can also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. Preferably, an innate immune response is elicited in a mammal as defined above. More preferably, the adjuvant protein is selected from human adjuvant proteins or from pathogenic adjuvant proteins, in particular from bacterial adjuvant proteins. In addition, mRNA encoding human proteins involved in adjuvant effects may be used as well.

Human adjuvant proteins, which may be encoded by the nucleic acid (sequence) of the inventive solution for lyophilization, transfection and/or injection typically comprise any human protein, which is capable of eliciting an innate immune response (in a mammal), e.g. as a reaction of the binding of an exogenous TLR ligand to a TLR. More preferably, human adjuvant proteins encoded by the nucleic acid (sequence) of the inventive solution for lyophilization, transfection and/or injection may be selected from the group consisting of, without being limited thereto, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59; from proteins which are components of the signalling networks of the pattern recognition receptors including TLR and IL-1R1, whereas the components are ligands of the pattern recognition receptors including IL-1alpha, IL-1 beta, Beta-defensin, heat shock proteins, such as HSP10, HSP60, HSP65, HSP70, HSP75 and HSP90, gp96, Fibrinogen, Typ111 repeat extra domain A of fibronectin; the receptors, including IL-1R1, TLR1, TLR2, TLR3, TLR4, TLR5, TLR6, TLR7, TLR8, TLR9, TLR10, TLR11; the signal transducers including components of the Small-GTPases signalling (RhoA, Ras, Rac1, Cdc42 etc.), components of the PIP signalling (PI3K, Src-Kinases, etc.), components of the MyD88-dependent signalling (MyD88, IRAK1, IRAK2, etc.), components of the MyD88-independent signalling (TICAM1, TICAM2 etc.); activated transcription factors including e.g. NF-κB, c-Fos, c-Jun, c-Myc; and induced target genes including e.g. IL-1alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

Pathogenic adjuvant proteins, which may be encoded by the nucleic acid (sequence) of the inventive solution for lyophilization, transfection and/or injection typically comprise any pathogenic (adjuvant) protein, which is capable of eliciting an innate immune response (in a mammal), more preferably selected from pathogenic (adjuvant) proteins derived from bacteria, protozoa, viruses, or fungi, animals, etc., and even more preferably from pathogenic adjuvant proteins selected from the group consisting of, without being limited thereto, bacterial proteins, protozoan proteins (e.g. profilin-like protein of *Toxoplasma gondii*), viral proteins, or fungal proteins, animal proteins, etc.

In this context, bacterial (adjuvant) proteins, which may be encoded by the nucleic acid (sequence) of the inventive solution for lyophilization, transfection and/or injection may comprise any bacterial protein, which is capable of eliciting an innate immune response (preferably in a mammal) or shows an adjuvant character. More preferably, such bacterial (adjuvant) proteins are selected from the group consisting of bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A; etc., or any species homolog of any of the above bacterial (adjuvant) proteins.

Bacterial (adjuvant) proteins, which may be encoded by the nucleic acid (sequence) of the inventive solution for lyophilization, transfection and/or injection may also be selected from bacterial adjuvant proteins, even more preferably selected from the group consisting of, without being limited thereto, bacterial flagellins, including flagellins from organisms including *Agrobacterium, Aquifex, Azospirillum, Bacillus, Bartonella, Bordetella, Borrelia, Burkholderia, Campylobacter, Caulobacte, Clostridium, Escherichia, Helicobacter, Lachnospiraceae, Legionella, Listeria, Proteus, Pseudomonas, Rhizobium, Rhodobacter, Roseburia, Salmonella, Serpulina, Serratia, Shigella, Treponema, Vibrio, Wolinella, Yersinia*, more preferably flagellins from the species, without being limited thereto, *Agrobacterium tumefaciens, Aquifex pyrophilus, Azospirillum brasilense, Bacillus subtilis, Bacillus thuringiensis, Bartonella bacilliformis, Bordetella bronchiseptica, Borrelia burgdorferi, Burkholderia cepacia, Campylobacter jejuni, Caulobacter crescentus, Clostridium botulinum* strain Bennett clone 1, *Escherichia coli, Helicobacter pylori, Lachnospiraceae bacterium, Legionella pneumophila, Listeria monocytogenes, Proteus mirabilis, Pseudomonas aeroguinosa, Pseudomonas syringae, Rhizobium meliloti, Rhodobacter sphaeroides, Roseburia cecicola, Roseburis hominis, Salmonella typhimurium, Salmonella bongori, Salmonella typhi, Salmonella enteritidis, Serpulina hyodysenteriae, Serratia marcescens, Shigella boydii, Treponema phagedenis, Vibrio alginolyticus, Vibrio cholerae, Vibrio parahaemolyticus, Wolinella succinogenes* and *Yersinia enterocolitica*.

Bacterial flagellins, which may be encoded by the nucleic acid (sequence) of the inventive solution for lyophilization, transfection and/or injection even more preferably comprise a sequence selected from the group comprising any of the following sequences as referred to their accession numbers:

| organism | species | gene name | accession No | GI No |
|---|---|---|---|---|
| *Agrobacterium* | *Agrobacterium tumefaciens* | FlaD (flaD)<br>FlhB (flhB)<br>FliG (fliG)<br>FliN (fliN)<br>FliM (fliM)<br>MotA (motA)<br>FlgF (flgF)<br>FliI (fliI)<br>FlgB (flgB)<br>FlgC (flgC)<br>FliE (fliE)<br>FlgG (flgG)<br>FlgA (flgA)<br>FlgI (flgI)<br>FlgH (flgH)<br>FliL (fliL)<br>FliP (fliP)<br>FlaA (flaA)<br>FlaB (flaB)<br>FlaC (flaC) | U95165 | GI:14278870 |
| *Aquifex* | *Aquifex pyrophilus* | | U17575 | GI:596244 |
| *Azospirillum* | *Azospirillum brasilense* | Laf1 | U26679 | GI:1173509 |
| *Bacillus* | *Bacillus subtilis* | hag | AB033501 | GI:14278870 |
| *Bacillus* | *Bacillus thuringiensis* | flab | X67138 | GI:46019718 |
| *Bartonella* | *Bartonella bacilliformis* | | L20677 | GI:304184 |

| organism | species | gene name | accession No | GI No |
|---|---|---|---|---|
| Bordetella | Bordetella bronchiseptica | flaA | L13034 | GI:289453 |
| Borrelia | Borrelia burgdorferi | | X16833 | GI:39356 |
| Burkholderia | Burkholderia cepacia | fliC | AF011370 | GI:2935154 |
| Campylobacter | Campylobacter jejuni | flaA flaB | J05635 | GI:144197 |
| Caulobacter | Caulobacter crescentus | | J01556 | GI:144239 |
| Clostridium | Clostridium botulinum strain Bennett clone 1 | FlaA | DQ845000 | GI:114054886 |
| Escherichia | Escherichia coli | hag | M14358 AJ 884569 (EMBL-SVA) | GI:146311 |
| Helicobacter | Helicobacter pylori | flaA | X60746 | GI:43631 |
| Lachnospiraceae | Lachnospiraceae bacterium | | DQ789131 | GI:113911615 |
| Legionella | Legionella pneumophila | flaA | X83232 | GI:602877 |
| Listeria | Listeria monocytogenes | flaA | X65624 | GI:44097 |
| Proteus | Proteus mirabilis | FlaD (flaD) FlaA (flaA) FlaB (flaB) FliA (fliA) FliZ (fliZ) | AF221596 | GI:6959881 |
| Pseudomonas | Pseudomonas aeroguinosa | flaA | M57501 | GI:151225 |
| Pseudomonas | Pseudomonas syringae | fliC | EF544882 | GI:146335619 |
| Rhizobium | Rhizobium meliloti | flaA flaB | M24526 | GI:152220 |
| Rhodobacter | Rhodobacter sphaeroides | fliC | AF274346 | GI:10716972 |
| Roseburia | Roseburia cecicola | | M20983 | GI:152535 |
| Roseburia | Roseburis hominis | Fla2 | DQ789141 | GI:113911632 |
| Salmonella | Salmonella typhimurium | | D13689 (NCBI ID) | GI:217062 |
| Salmonella | Salmonella bongori | fliC | AY603412 | GI:51342390 |
| Salmonella | Salmonella typhi | flag | L21912 | GI:397810 |
| Salmonella | Salmonella enteritidis | fliC | M84980 | GI:154015 |
| Serpulina | Serpulina hyodysenteriae | flaB2 | X63513 | GI:450669 |
| Serratia | Serratia marcescens | hag | M27219 | GI:152826 |
| Shigella | Shigella boydii | fliC-SB | D26165 | GI:442485 |
| Treponema | Treponema phagedenis | flaB2 | M94015 | GI:155060 |
| Vibrio | Vibrio alginolyticus | flaA | EF125175 | GI:119434395 |
| Vibrio s | Vibrio parahaemolyticus | | AF069392 | GI:7327274 |
| Wolinella | Wolinella succinogenes | flag | M82917 | GI:155337 |
| Yersinia | Yersinia enterocolitica | | L33467 | GI:496295 |

Protozoan proteins, which may also be encoded by the nucleic acid (sequence) of the inventive solution for lyophilization, transfection and/or injection may be selected from any protozoan protein showing adjuvant character, more preferably, from the group consisting of, without being limited thereto, Tc52 from *Trypanosoma cruzi*, PFTG from *Trypanosoma gondii*, Protozoan heat shock proteins, LeIF from *Leishmania* spp., profilin-like protein from *Toxoplasma gondii*, etc.

Viral proteins, which may be encoded by the nucleic acid (sequence) of the inventive solution for lyophilization, transfection and/or injection may be selected from any viral protein showing adjuvant character, more preferably, from the group consisting of, without being limited thereto, Respiratory Syncytial Virus fusion glycoprotein (F-protein), envelope protein from MMT virus, mouse leukemia virus protein, Hemagglutinin protein of wild type measles virus, etc.

Fungal proteins, which may be encoded by the nucleic acid (sequence) of the inventive solution for lyophilization, transfection and/or injection may be selected from any fungal protein showing adjuvant character, more preferably, from the group consisting of, without being limited thereto, fungal immunomodulatory protein (FIP; LZ-8), etc.

Finally, pathogenic adjuvant proteins, which may be encoded by the nucleic acid (sequence) of the inventive solution for lyophilization, transfection and/or injection may finally be selected from any further pathogenic protein showing adjuvant character, more preferably, from the group consisting of, without being limited thereto, Keyhole limpet hemocyanin (KLH), OspA, etc.

b) Antigens

The nucleic acid (sequence) of the inventive solution for lyophilization, transfection and/or injection may alternatively encode an antigen. According to the present invention, the term "antigen" refers to a substance which is recognized by the immune system and is capable of triggering an antigen-specific immune response, e.g. by formation of antibodies as part of an adaptive immune response. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecule—MHC class I and MHC class II—which differ in their structure and expression pattern on tissues of the body. $CD4^+$ T cells bind to the MHC class II molecule and $CD8^+$ T cells to the MHC class I molecule. MHC class I and MHC class II have distinct distributions among cells that reflect the different effector functions of the T cells that recognize them. MHC class I molecules present peptides from pathogens, commonly viruses to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogen. The $CD8^+$ T cells that recognize MHC class I:peptide complexes are specialized to kill any cells displaying foreign peptides and so rid the body of cells infected with viruses and other cytosolic pathogens. The main function of $CD4^+$ T cells ($CD4^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties, of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

In the context of the present invention, antigens as encoded by the nucleic acid (sequence) of the inventive solution for lyophilization, transfection and/or injection typically comprise any antigen, falling under the above definition, more preferably protein and peptide antigens, e.g. tumor antigens, allergy antigens, auto-immune self-antigens, pathogens, etc. In accordance with the invention, antigens as encoded by the nucleic acid (sequence) of the inventive solution for lyophilization, transfection and/or injection may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens (preferably selected from animals or organisms as disclosed herein), allergy antigens, etc. Allergy antigens are typically antigens, which cause an allergy in a human and may be derived from either a human or other sources. Antigens as encoded by the nucleic acid (sequence) of the inventive solution for lyophilization, transfection and/or injection may be furthermore antigens generated inside the cell, the tissue or the body, e.g. by secretion of proteins, their degradation, metabolism, etc. Such antigens include antigens derived from the host organism (e.g. a human) itself, e.g. tumor antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc.

One class of antigens as encoded by the nucleic acid (sequence) of the inventive solution for lyophilization, transfection and/or injection comprises tumor antigens. "Tumor antigens" are preferably located on the surface of the (tumor) cell. Tumor antigens may also be selected from proteins, which are overexpressed in tumor cells compared to a normal cell. Furthermore, tumor antigens also includes antigens expressed in cells which are (were) not themselves (or originally not themselves) degenerated but are associated with the supposed tumor. Antigens which are connected with tumor-supplying vessels or (re)formation thereof, in particular those antigens which are associated with neovascularization, e.g. growth factors, such as VEGF, bFGF etc., are also included herein. Antigens connected with a tumor furthermore include antigens from cells or tissues, typically embedding the tumor. Further, some substances (usually proteins or peptides) are expressed in patients suffering (knowingly or not-knowingly) from a cancer disease and they occur in increased concentrations in the body fluids of said patients. These substances are also referred to as "tumor antigens", however they are not antigens in the stringent meaning of an immune response inducing substance. The class of tumor antigens can be divided further into tumor-specific antigens (TSAs) and tumor-associated-antigens (TAAs). TSAs can only be presented by tumor cells and never by normal "healthy" cells. They typically result from a tumor specific mutation. TAAs, which are more common, are usually presented by both tumor and healthy cells. These antigens are recognized and the antigen-presenting cell can be destroyed by cytotoxic T cells. Additionally, tumor antigens can also occur on the surface of the tumor in the form of, e.g., a mutated receptor. In this case, they can be recognized by antibodies.

Examples of tumor antigens as encoded by the nucleic acid (sequence) of the inventive solution for lyophilization, transfection and/or injection are shown in Tables 1 and 2 below. These tables illustrate specific (protein) antigens (i.e. "tumor antigens") with respect to the cancer disease, they are associated with. According to the invention, the terms "cancer diseases" and "tumor diseases" are used synonymously herein.

TABLE 1

Antigens expressed in cancer diseases

| Tumor antigen | Name of tumor antigen | Cancers or cancer diseases related thereto |
|---|---|---|
| 5T4 | | colorectal cancer, gastric cancer, ovarian cancer |
| 707-AP | 707 alanine proline | Melanoma |
| 9D7 | | renal cell carcinoma |
| AFP | alpha-fetoprotein | hepatocellular carcinoma, gallbladder cancer, testicular cancer ovarian cancer, bladder cancer |
| AlbZIP HPG1 | | prostate cancer |
| alpha5beta1-Integrin | | |
| alpha5beta6-Integrin | | colon cancer |
| alpha-methylacyl-coenzyme A racemase | | prostate cancer |
| ART-4 | adenocarcinoma antigen recognized by T cells 4 | lung cancer, head and neck cancer, leukemia, esophageal cancer, gastric cancer, cervical cancer, ovarian cancer, breast cancer, squamous cell carcinoma |
| B7H4 | | ovarian cancer |
| BAGE-1 | B antigen | bladder cancer, head and neck cancer, lung cancer, melanoma, squamous cell carcinoma |
| BCL-2 | | leukemia |
| BING-4 | | melanoma |
| CA 15-3/CA 27-29 | | breast cancer, ovary cancer, lung cancer, prostate cancer |
| CA 19-9 | | gastric cancer, pancreatic cancer, liver cancer, breast cancer, gallbladder cancer, colon cancer, ovary cancer, lung cancer |
| CA 72-4 | | ovarian cancer |
| CA125 | | ovarian cancer, colorectal cancer, gastric cancer, liver cancer, pancreatic cancer, uterus cancer, cervix carcinoma, colon cancer, breast cancer, lung cancer |
| calreticulin | | bladder cancer |
| CAMEL | CTL-recognized antigen on melanoma | melanoma |
| CASP-8 | caspase-8 | head and neck cancer |
| cathepsin B | | breast cancer |
| cathepsin L | | breast cancer |
| CD19 | | B-cell malignancies |
| CD20 | | |
| CD22 | | |
| CD25 | | |
| CD30 | | |

TABLE 1-continued

Antigens expressed in cancer diseases

| Tumor antigen | Name of tumor antigen | Cancers or cancer diseases related thereto |
|---|---|---|
| CD33 | | |
| CD4 | | |
| CD52 | | |
| CD55 | | |
| CD56 | | |
| CD80 | | |
| CEA | carcinoembryonic antigen | gut carcinoma, colorectal cancer, colon cancer, hepatocellular cancer, lung cancer, breast cancer, thyroid cancer, pancreatic cancer, liver cancer cervix cancer, bladder cancer, melanoma |
| CLCA2 | calcium-activated chloride channel-2 | lung cancer |
| CML28 | | leukemia |
| Coactosin-like protein | | pancreatic cancer |
| Collagen XXIII | | prostate cancer |
| COX-2 | | ovarian cancer, breast cancer, colorectal cancer |
| CT-9/BRD6 | bromodomain testis-specific protein | |
| Cten | C-terminal tensin-like protein | prostate cancer |
| cyclin B1 | | |
| cyclin D1 | | ovarian cancer |
| cyp-B | cyclophilin B | bladder cancer, lung cancer, T-cell leukemia, squamous cell carcinoma, |
| CYPB1 | cytochrom P450 1B1 | leukemia |
| DAM-10/MAGE-B1 | differentiation antigen melanoma 10 | melanoma, skin tumors, ovarian cancer, lung cancer |
| DAM-6/MAGE-B2 | differentiation antigen melanoma 6 | melanoma, skin tumors, ovarian cancer, lung cancer |
| EGFR/Her1 | | lung cancer, ovarian cancer, head and neck cancer, colon cancer, pancreatic cancer, breast cancer |
| EMMPRIN | tumor cell-associated extracellular matrix metalloproteinase inducer/ | lung cancer, breast cancer, bladder cancer, ovarian cancer, brain cancer, lymphoma |
| EpCam | epithelial cell adhesion molecule | ovarian cancer, breast cancer, colon cancer, lung cancer |
| EphA2 | ephrin type-A receptor 2 | glioma |
| EphA3 | ephrin type-A receptor 2 | melanoma, sarcoma, lung cancer |
| ErbB3 | | breast cancer |
| EZH2 | (enhancer of Zeste homolog 2) | endometrium cancer, melanoma, prostate cancer, breast cancer |
| FGF-5 | fibroblast growth factor-5 | renal cell carcinoma, breast cancer, prostate cancer |
| FN | fibronectin | melanoma |
| Fra-1 | Fos-related antigen-1 | breast cancer, esophageal cancer, renal cell carcinoma, thyroid cancer |
| G250/CAIX | glycoprotein 250 | leukemia, renal cell carcinoma, head and neck cancer, colon cancer, ovarian cancer, cervical cancer |
| GAGE-1 | G antigen 1 | bladder cancer, lung cancer, sarcoma, melanoma, head and neck cancer |
| GAGE-2 | G antigen 2 | bladder cancer, lung cancer, sarcoma, melanoma, head and neck cancer |
| GAGE-3 | G antigen 3 | bladder cancer, lung cancer, sarcoma, melanoma, head and neck cancer |
| GAGE-4 | G antigen 4 | bladder cancer, lung cancer, sarcoma, melanoma, head and neck cancer |
| GAGE-5 | G antigen 5 | bladder cancer, lung cancer, sarcoma, melanoma, head and neck cancer |
| GAGE-6 | G antigen 6 | bladder cancer, lung cancer, sarcoma, melanoma, head and neck cancer |
| GAGE-7b | G antigen 7b | bladder cancer, lung cancer, sarcoma, melanoma, head and neck cancer |

TABLE 1-continued

Antigens expressed in cancer diseases

| Tumor antigen | Name of tumor antigen | Cancers or cancer diseases related thereto |
|---|---|---|
| GAGE-8 | G antigen 8 | bladder cancer, lung cancer, sarcoma, melanoma, head and neck cancer |
| GDEP | gene differentially expressed in prostate | prostate cancer |
| GnT-V | N-acetylglucosaminyltransferase V | glioma, melanoma |
| gp100 | glycoprotein 100 kDa | melanoma |
| GPC3 | glypican 3 | hepatocellular carcinoma, melanoma |
| HAGE | helicase antigen | bladder cancer |
| HAST-2 | human signet ring tumor-2 | |
| hepsin | | prostate |
| Her2/neu/ErbB2 | human epidermal receptor-2/neurological | breast cancer, bladder cancer, melanoma, ovarian cancer, pancreas cancer, gastric cancer |
| HERV-K-MEL | | melanoma |
| HNE | human neutrophil elastase | leukemia |
| homeobox NKX 3.1 | | prostate cancer |
| HOM-TES-14/SCP-1 | | ovarian cancer |
| HOM-TES-85 | | |
| HPV-E6 | | cervical cancer |
| HPV-E7 | | cervical cancer |
| HST-2 | | gastric cancer |
| hTERT | human telomerase reverse transcriptase | breast cancer, melanoma, lung cancer, ovarian cancer, sarcoma, Non-Hodgkin-lymphoma, acute leukemia |
| iCE | intestinal carboxyl esterase | renal cell carcinoma |
| IGF-1R | | colorectal cancer |
| IL-13Ra2 | interleukin 13 receptor alpha 2 chain | glioblastoma |
| IL-2R | | colorectal cancer |
| IL-5 | | |
| immature laminin receptor | | renal cell carcinoma |
| kallikrein 2 | | prostate cancer |
| kallikrein 4 | | prostate cancer |
| Ki67 | | prostate cancer, breast cancer, Non-Hodgkin-lymphoma, melanoma |
| KIAA0205 | | bladder cancer |
| KK-LC-1 | Kita-kyushu lung cancer antigen 1 | lung cancer |
| KM-HN-1 | | tongue cancer, hepatocellular carcinomas, melanoma, gastric cancer, esophageal, colon cancer, pancreatic cancer |
| LAGE-1 | L antigen | bladder cancer, head and neck cancer, melanoma |
| livin | | bladder cancer, melanoma |
| MAGE-A1 | melanoma antigen-A1 | bladder cancer, head and neck cancer, melanoma, colon cancer, lung cancer, sarcoma, leukemia |
| MAGE-A10 | melanoma antigen-A10 | bladder cancer, head and neck cancer, melanoma, colon cancer, lung cancer, sarcoma, leukemia |
| MAGE-A12 | melanoma antigen-A12 | bladder cancer, head and neck cancer, melanoma, colon cancer, lung cancer, sarcoma, leukemia, prostate cancer, myeloma, brain tumors |
| MAGE-A2 | melanoma antigen-A2 | bladder cancer, head and neck cancer, melanoma, colon cancer, lung cancer, sarcoma, leukemia |
| MAGE-A3 | melanoma antigen-A3 | bladder cancer, head and neck cancer, melanoma, colon cancer, lung cancer, sarcoma, leukemia |
| MAGE-A4 | melanoma antigen-A4 | bladder cancer, head and neck cancer, melanoma, colon cancer, lung cancer, sarcoma, leukemia |
| MAGE-A6 | melanoma antigen-A6 | bladder cancer, head and neck cancer, melanoma, colon cancer, lung cancer, sarcoma, leukemia |

TABLE 1-continued

Antigens expressed in cancer diseases

| Tumor antigen | Name of tumor antigen | Cancers or cancer diseases related thereto |
|---|---|---|
| MAGE-A9 | melanoma-antigen-A9 | bladder cancer, head and neck cancer, melanoma, colon cancer, lung cancer, sarcoma, leukemia |
| MAGE-B1 | melanoma-antigen-B1 | melanoma |
| MAGE-B10 | melanoma-antigen-B10 | melanoma |
| MAGE-B16 | melanoma-antigen-B16 | melanoma |
| MAGE-B17 | melanoma-antigen-B17 | melanoma |
| MAGE-B2 | melanoma-antigen-B2 | melanoma |
| MAGE-B3 | melanoma-antigen-B3 | melanoma |
| MAGE-B4 | melanoma-antigen-B4 | melanoma |
| MAGE-B5 | melanoma-antigen-B5 | melanoma |
| MAGE-B6 | melanoma-antigen-B6 | melanoma |
| MAGE-C1 | melanoma-antigen-C1 | bladder cancer, melanoma |
| MAGE-C2 | melanoma-antigen-C2 | melanoma |
| MAGE-C3 | melanoma-antigen-C3 | melanoma |
| MAGE-D1 | melanoma-antigen-D1 | melanoma |
| MAGE-D2 | melanoma-antigen-D2 | melanoma |
| MAGE-D4 | melanoma-antigen-D4 | melanoma |
| MAGE-E1 | melanoma-antigen-E1 | bladder cancer, melanoma |
| MAGE-E2 | melanoma-antigen-E2 | melanoma |
| MAGE-F1 | melanoma-antigen-F1 | melanoma |
| MAGE-H1 | melanoma-antigen-H1 | melanoma |
| MAGEL2 | MAGE-like 2 | melanoma |
| mammaglobin A | | breast cancer |
| MART-1/Melan-A | melanoma antigen recognized by T cells-1/melanoma antigen A | melanoma |
| MART-2 | melanoma antigen recognized by T cells-2 | melanoma |
| matrix protein 22 | | bladder cancer |
| MC1R | melanocortin 1 receptor | melanoma |
| M-CSF | macrophage colony-stimulating factor gene | ovarian cancer |
| mesothelin | | ovarian cancer |
| MG50/PXDN | | breast cancer, glioblastoma, melanoma |
| MMP 11 | M-phase phosphoprotein 11 | leukemia |
| MN/CA IX-antigen | | renal cell carcinoma |
| MRP-3 | multidrug resistance-associated protein 3 | lung cancer |
| MUC1 | mucin 1 | breast cancer |
| MUC2 | mucin 2 | breast cancer, ovarian cancer, pancreatic cancer |
| NA88-A | NA cDNA clone of patient M88 | melanoma |
| N-acetylglucos-aminyltransferase-V | | |
| Neo-PAP | Neo-poly(A) polymerase | |
| NGEP | | prostate cancer |
| NMP22 | | bladder cancer |
| NPM/ALK | nucleophosmin/anaplastic lymphoma kinase fusion protein | |
| NSE | neuron-specific enolase | small cell cancer of lung, neuroblastoma, Wilm' tumor, melanoma, thyroid cancer, kidney cancer, testicle cancer, pancreas cancer |
| NY-ESO-1 | New York esophageous 1 | bladder cancer, head and neck cancer, melanoma, sarcoma, B-lymphoma, hepatoma, pancreatic cancer, ovarian cancer, breast cancer |
| NY-ESO-B | | |
| OA1 | ocular albinism type 1 protein | melanoma |
| OFA-iLRP | oncofetal antigen-immature laminin receptor | leukemia |
| OGT | O-linked N-acetylglucosamine transferase gene | |
| OS-9 | | |
| osteocalcin | | prostate cancer |
| osteopontin | | prostate cancer, breast cancer, ovarian cancer |

TABLE 1-continued

Antigens expressed in cancer diseases

| Tumor antigen | Name of tumor antigen | Cancers or cancer diseases related thereto |
|---|---|---|
| p15 | protein 15 | |
| p15 | | melanoma |
| p190 minor bcr-abl | | |
| p53 | | |
| PAGE-4 | prostate GAGE-like protein-4 | prostate cancer |
| PAI-1 | plasminogen acitvator inhibitor 1 | breast cancer |
| PAI-2 | plasminogen acitvator inhibitor 2 | breast cancer |
| PAP | prostate acic phosphatase | prostate cancer |
| PART-1 | | prostate cancer |
| PATE | | prostate cancer |
| PDEF | | prostate cancer |
| Pim-1-Kinase | | |
| Pin1 | Propyl isomerase | prostate cancer |
| POTE | | prostate cancer |
| PRAME | preferentially expressed antigen of melanoma | melanoma, lung cancer, leukemia, head and neck cancer, renal cell carcinoma, sarcoma |
| prostein | | prostate cancer |
| proteinase-3 | | |
| PSA | prostate-specific antigen | prostate cancer |
| PSCA | | prostate cancer |
| PSGR | | prostate cancer |
| PSM | | |
| PSMA | prostate-specific membrane antigen | prostate cancer |
| RAGE-1 | renal antigen | bladder cancer, renal cancer, sarcoma, colon cancer |
| RHAMM/CD168 | receptor for hyaluronic acid mediated motility | leukemia |
| RU1 | renal ubiquitous 1 | bladder cancer, melanoma, renal cancer |
| RU2 | renal ubiquitous 1 | bladder cancer, melanoma, sarcoma brain tumor, esophagel cancer, renal cancer, colon cancer, breast cancer |
| S-100 | | melanoma |
| SAGE | sarcoma antigen | |
| SART-1 | squamous antigen rejecting tumor 1 | esophageal cancer, head and neck cancer, lung cancer, uterine cancer |
| SART-2 | squamous antigen rejecting tumor 1 | head and neck cancer, lung cancer, renal cell carcinoma, melanoma, brain tumor |
| SART-3 | squamous antigen rejecting tumor 1 | head and neck cancer, lung cancer, leukemia, melanoma, esophageal cancer |
| SCC | squamous cell carcinoma antigen | lung cancer |
| Sp17 | sperm protein 17 | multiple myeloma |
| SSX-1 | synovial sarcoma X breakpoint 1 | hepatocellular cell carcinom, breast cancer |
| SSX-2/HOM-MEL-40 | synovial sarcoma X breakpoint 2 | breast cancer |
| SSX-4 | synovial sarcoma X breakpoint 4 | bladder cancer, hepatocellular cell carcinoma, breast cancer |
| STAMP-1 | | prostate cancer |
| STEAP | six transmembrane epithelial antigen prostate | prostate cancer |
| survivin | | bladder cancer |
| survivin-2B | intron 2-retaining survivin | bladder cancer |
| TA-90 | | melanoma |
| TAG-72 | | prostate carcinoma |
| TARP | | prostate cancer |
| TGFb | TGFbeta | |
| TGFbRII | TGFbeta receptor II | |
| TGM-4 | prostate-specific transglutaminase | prostate cancer |
| TRAG-3 | taxol resistant associated protein 3 | breast cancer, leukemia, and melanoma |
| TRG | testin-related gene | |
| TRP-1 | tyrosine related protein 1 | melanoma |
| TRP-2/6b | TRP-2/novel exon 6b | melanoma, glioblastoma |
| TRP-2/INT2 | TRP-2/intron 2 | melanoma, glioblastoma |
| Trp-p8 | | prostate cancer |
| Tyrosinase | | melanoma |
| UPA | urokinase-type plasminogen activator | breast cancer |

TABLE 1-continued

Antigens expressed in cancer diseases

| Tumor antigen | Name of tumor antigen | Cancers or cancer diseases related thereto |
|---|---|---|
| VEGF | vascular endothelial growth factor | |
| VEGFR-2/FLK-1 | vascular endothelial growth factor receptor-2 | |
| WT1 | Wilm' tumor gene | gastric cancer, colon cancer, lung cancer, breast cancer, ovarian cancer, leukemia |

TABLE 2

Mutant antigens expressed in cancer diseases

| Mutant antigen | Name of mutant antigen | Cancers or cancer diseases related thereto |
|---|---|---|
| alpha-actinin-4/m | | lung carcinoma |
| ARTC1/m | | melanoma |
| bcr/abl | breakpoint cluster region-Abelson fusion protein | CML |
| beta-Catenin/m | beta-Catenin | melanoma |
| BRCA1/m | | breast cancer |
| BRCA2/m | | breast cancer |
| CASP-5/m | | colorectal cancer, gastric cancer, endometrial carcinoma |
| CASP-8/m | | head and neck cancer, squamous cell carcinoma |
| CDC27/m | cell-division-cycle 27 | |
| CDK4/m | cyclin-dependent kinase 4 | melanoma |
| CDKN2A/m | | melanoma |
| CML66 | | CML |
| COA-1/m | | colorectal cancer |
| DEK-CAN | fusion protein | AML |
| EFTUD2/m | | melanoma |
| ELF2/m | Elongation factor 2 | lung squamous cell carcinoma |
| ETV6-AML1 | Ets variant gene6/acute myeloid leukemia 1 gene fusion protein | ALL |
| FN1/m | fibronectin 1 | melanoma |
| GPNMB/m | | melanoma |
| HLA-A*0201-R170I | arginine to isoleucine exchange at residue 170 of the alpha-helix of the alpha2-domain in the HLA-A2 gene | renal cell carcinoma |
| HLA-A11/m | | melanoma |
| HLA-A2/m | | renal cell carcinoma |
| HSP70-2M | heat shock protein 70-2 mutated | renal cell carcinoma, melanoma, neuroblastoma |
| KIAA0205/m | | bladder tumor |
| K-Ras/m | | pancreatic carcinoma, colorectal carcinoma |
| LDLR-FUT | LDR-Fucosyltransferase fusion protein | melanoma |
| MART2/m | | melanoma |
| ME1/m | | non-small cell lung carcinoma |
| MUM-1/m | melanoma ubiquitous mutated 1 | melanoma |
| MUM-2/m | melanoma ubiquitous mutated 2 | melanoma |
| MUM-3/m | melanoma ubiquitous mutated 3 | melanoma |
| Myosin class I/m | | melanoma |
| neo-PAP/m | | melanoma |
| NFYC/m | | lung squamous cell carcinoma |
| N-Ras/m | | melanoma |
| OGT/m | | colorectal carcinoma |
| OS-9/m | | melanoma |
| p53/m | | |
| Pml/RARa | promyelocytic leukemia/retinoic acid receptor alpha | APL, PML |
| PRDX5/m | | melanoma |
| PTPRK/m | receptor-type protein-tyrosine phosphatase kappa | melanoma |
| RBAF600/m | | melanoma |
| SIRT2/m | | melanoma |
| SYT-SSX-1 | synaptotagmin I/synovial sarcoma X fusion protein | sarcoma |
| SYT-SSX-2 | synaptotagmin I/synovial sarcoma X fusion protein | sarcoma |

TABLE 2-continued

Mutant antigens expressed in cancer diseases

| Mutant antigen | Name of mutant antigen | Cancers or cancer diseases related thereto |
| --- | --- | --- |
| TEL-AML1 | translocation Ets-family leukemia/acute myeloid leukemia 1 fusion protein | AML |
| TGFbRII | TGFbeta receptor II | colorectal carcinoma |
| TPI/m | triosephosphate isomerase | Melanoma |

In a preferred aspect of the present invention, the tumor antigens as encoded by the nucleic acid (sequence) of the inventive solution for lyophilization, transfection and/or injection are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20 CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-IR, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MCIR, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaR11, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

In a particularly preferred aspect, the tumor antigens as encoded by the nucleic acid (sequence) of the inventive solution for lyophilization, transfection and/or injection are selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), survivin (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFR1 (epidermal growth factor receptor 1) (e.g. EGFR1 (epidermal growth factor receptor 1) according to accession number AF288738), MUC1, mucin-1 (e.g. mucin-1 according to accession number NM_002456), SEC6G (e.g. SEC61G according to accession number NM_014302), hTERT (e.g. hTERT accession number NMI_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

According to a further particularly preferred aspect, the tumor antigens as encoded by the nucleic acid (sequence) of the inventive solution for lyophilization, transfection and/or injection may form a cocktail of antigens, e.g. in an active (immunostimulatory) composition or a kit of parts (wherein preferably each antigen is contained in one part of the kit), preferably for eliciting an (adaptive) immune response for the treatment of prostate cancer (PCa), preferably of neo-adjuvant and/or hormone-refractory prostate cancers, and diseases or disorders related thereto. For this purpose, the nucleic acid (sequence) of the inventive solution for lyophilization, transfection and/or injection is preferably at least one RNA, more preferably at least one mRNA, which may encode at least one, preferably two, three or even four (preferably different) antigens of the following group of antigens:

PSA (Prostate-Specific Antigen)=KLK3 (Kallikrein-3),
PSMA (Prostate-Specific Membrane Antigen),
PSCA (Prostate Stem Cell Antigen),
STEAP (Six Transmembrane Epithelial Antigen of the Prostate).

More preferably, in the latter aspect, the nucleic acid (sequence) of the inventive solution for lyophilization, transfection and/or injection may also be at least one RNA, more preferably at least one mRNA, which may encode at least two, three or four (preferably different) antigens of the following combinations of antigens:

PSA and PSMA, or
PSA and PSCA, or

PSA and STEAP, or
PSMA and PSCA, or
PSMA and STEAP, or
PSCA and STEAP,
or
PSA, PSMA and PSCA, or
PSA, PSMA and STEAP, or
PSMA, PSCA and STEAP, or
PSA, PSCA and STEAP, or
or
PSA, PSMA, PSCA and STEAP Even more preferably, in the latter aspect, the nucleic acid (sequence) of the inventive solution for lyophilization, transfection and/or injection may also be at least one RNA, more preferably at least one mRNA, which may encode at least two, three or four (preferably different) antigens:
wherein at least one antigen is selected from:
STEAP (Six Transmembrane Epithelial Antigen of the Prostate); and
b) wherein the further antigen(s) is (are) selected from at least one antigen of any of the following specific antigens or combinations thereof:
PSA (Prostate-Specific Antigen), or
PSMA (Prostate-Specific Membrane Antigen), or
PSCA (Prostate Stem Cell Antigen);
or
PSA and PSMA, or
PSA and PSCA, or
PSMA and PSCA;
or
PSA, PSMA and PSCA.

Most preferably, in the latter aspect, the nucleic acid (sequence) of the inventive solution for lyophilization, transfection and/or injection may also be at least one RNA, more preferably at least one mRNA, encoding four (preferably different) antigens selected from PSA, PSMA, PSCA and STEAP.

According to another particularly preferred aspect, the tumor antigens as encoded by the nucleic acid (sequence) of the inventive solution for lyophilization, transfection and/or injection may form a cocktail of antigens, e.g. in an active (immunostimulatory) composition or a kit of parts (wherein preferably each antigen is contained in one part of the kit), preferably for eliciting an (adaptive) immune response for the treatment of non-small cell lung cancers (NSCLC), preferably selected from the three main sub-types squamous cell lung carcinoma, adenocarcinoma and large cell lung carcinoma, or of disorders related thereto. For this purpose, the nucleic acid (sequence) of the inventive solution for lyophilization, transfection and/or injection is preferably at least one RNA, more preferably at least one mRNA, which may encode at least one, preferably two, three, four, five, six, seven, eight, nine, ten eleven or twelve (preferably different) antigens of the following group of antigens:
hTERT,
WT1,
MAGE-A2,
5T4,
MAGE-A3,
MUC1,
Her-2/neu,
NY-ESO-1,
CEA,
Survivin,
MAGE-C1, and/or
MAGE-C2,
wherein any combination of these antigens is possible.

More preferably, in the latter aspect, the nucleic acid (sequence) of the inventive solution for lyophilization, transfection and/or injection may also be at least one RNA, more preferably at least one mRNA, which may encode at least two, three, five or six (preferably different) antigens of the following combinations of antigens:
hTERT,
WT1,
5T4,
NY-ESO-1,
Survivin, and/or
MAGE-C2,
wherein any combination of these antigens is possible.

Even more preferably, in the latter aspect, the nucleic acid (sequence) of the inventive solution for lyophilization, transfection and/or injection may also be at least one RNA, more preferably at least one mRNA, which may encode at least one, preferably two, three, four, five, six, seven, eight, nine, ten eleven or twelve (preferably different) antigens of the following combinations of antigens:
hTERT and WT1, or
hTERT and 5T4, or
hTERT and NY-ESO-1, or
hTERT and Survivin, or
hTERT and MAGE-C2, or
WT1 and 5T4, or
WT1 and NY-ESO-1, or
WT1 and Survivin, or
WT1 and MAGE-C2, or
5T4 and NY-ESO-1, or
5T4 and Survivin, or
5T4 and MAGE-C2, or
NY-ESO-1 and Survivin, or
NY-ESO-1 and MAGE-C2, or
Survivin and MAGE-C2,
or
hTERT, WT1 and 5T4, or
hTERT, WT1 and NY-ESO-1, or
hTERT, WT1 and Survivin, or
hTERT, WT1 and MAGE-C2, or
hTERT, 5T4, and NY-ESO-1, or
hTERT, 5T4, and Survivin, or
hTERT, 5T4, and MAGE-C2, or
hTERT, NY-ESO-1 and Survivin, or
hTERT, NY-ESO-1 and MAGE-C2, or
hTERT, Survivin and MAGE-C2, or
WT1, 5T4 and NY-ESO-1, or
WT1, 5T4 and Survivin, or
WT1, 5T4 and MAGE-C2, or
WT1, NY-ESO-1 and Survivin, or
WT1, NY-ESO-1 and MAGE-C2, or
WT1, Survivin and MAGE-C2, or
5T4, NY-ESO-1 and Survivin, or
5T4, NY-ESO-1 and MAGE-C2, or
5T4, Survivin and MAGE-C2, or
NY-ESO-1, Survivin, and MAGE-C2,
or
hTERT, WT1, 5T4 and NY-ESO-1, or
hTERT, WT1, 5T4 and Survivin, or
hTERT, WT1, 5T4 and MAGE-C2, or
hTERT, 5T4, NY-ESO-1 and Survivin, or
hTERT, 5T4, NY-ESO-1 and MAGE-C2, or
hTERT, NY-ESO-1, Survivin and MAGE-C2, or WT1, 5T4, NY-ESO-1, and Survivin, or
WT1, 5T4, NY-ESO-1, and MAGE-C2, or
WT1, 5T4, Survivin, and MAGE-C2, or
5T4, NY-ESO-1, Survivin, and MAGE-C2,
or
hTERT, WT1, 5T4, NY-ESO-1 and Survivin, or
hTERT, WT1, 5T4, NY-ESO-1 and MAGE-C2, or
WT1, 5T4, NY-ESO-1, Survivin and MAGE-C2,
or
hTERT, WT1, 5T4, NY-ESO-1, Survivin, and MAGE-C2.

Preferably, in the latter aspect, the nucleic acid (sequence) of the inventive solution for lyophilization, transfection and/or injection may also be at least one RNA, more preferably at least one mRNA, which may encode at least two (preferably different) antigens exclusively selected from any of the antigens of the above mentioned group(s) or subgroup(s) comprising (at least) any one of the following combinations of antigens:

hTERT and WT1, or
hTERT and 5T4, or
hTERT and NY-ESO-1, or
hTERT and Survivin, or
hTERT and MAGE-C2, or
WT1 and 5T4, or
WT1 and NY-ESO-1, or
WT1 and Survivin, or
WT1 and MAGE-C2, or
5T4 and NY-ESO-1, or
5T4 and Survivin, or
5T4 and MAGE-C2, or
NY-ESO-1 and Survivin, or
NY-ESO-1 and MAGE-C2, or
Survivin and MAGE-C2,
or
hTERT, WT1 and 5T4, or
hTERT, WT1 and NY-ESO-1, or
hTERT, WT1 and Survivin, or
hTERT, WT1 and MAGE-C2, or
hTERT, 5T4, and NY-ESO-1, or
hTERT, 5T4, and Survivin, or
hTERT, 5T4, and MAGE-C2, or
hTERT, NY-ESO-1 and Survivin, or
hTERT, NY-ESO-1 and MAGE-C2, or
hTERT, Survivin and MAGE-C2, or
WT1, 5T4 and NY-ESO-1, or
WT1, 5T4 and Survivin, or
WT1, 5T4 and MAGE-C2, or
WT1, NY-ESO-1 and Survivin, or
WT1, NY-ESO-1 and MAGE-C2, or
WT1, Survivin and MAGE-C2, or
5T4, NY-ESO-1 and Survivin, or
5T4, NY-ESO-1 and MAGE-C2, or
5T4, Survivin and MAGE-C2, or
NY-ESO-1, Survivin, and MAGE-C2,
or
hTERT, WT1, 5T4 and NY-ESO-1, or
hTERT, WT1, 5T4 and Survivin, or
hTERT, WT1, 5T4 and MAGE-C2, or
hTERT, 5T4, NY-ESO-1 and Survivin, or
hTERT, 5T4, NY-ESO-1 and MAGE-C2, or
hTERT, NY-ESO-1, Survivin and MAGE-C2, or
WT1, 5T4, NY-ESO-1, and Survivin, or
WT1, 5T4, NY-ESO-1, and MAGE-C2, or
WT1, 5T4, Survivin, and MAGE-C2, or
5T4, NY-ESO-1, Survivin, and MAGE-C2,
or
hTERT, WT1, 5T4, NY-ESO-1 and Survivin, or
hTERT, WT1, 5T4, NY-ESO-1 and MAGE-C2, or
WT1, 5T4, NY-ESO-1, Survivin and MAGE-C2,
or
hTERT, WT1, 5T4, NY-ESO-1, Survivin, and MAGE-C2.

According to a further particularly preferred aspect, the tumor antigens as encoded by the nucleic acid (sequence) of the inventive solution for lyophilization, transfection and/or injection may form a cocktail of antigens, e.g. in an active (immunostimulatory) composition or a kit of parts (wherein preferably each antigen is contained in one part of the kit), preferably for eliciting an (adaptive) immune response for the treatment of non-small cell lung cancers (NSCLC), preferably selected from the three main sub-types squamous cell lung carcinoma, adenocarcinoma and large cell lung carcinoma, or of disorders related thereto. For this purpose, the nucleic acid (sequence) of the inventive solution for lyophilization, transfection and/or injection is preferably at least one RNA, more preferably at least one mRNA, which may encode at least two (preferably different) antigens, a) wherein at least one, preferably at least two, three, four, five or even six, of these at least two antigens is (are) selected from:
5T4
NY-ESO-1,
MAGE-A2,
MAGE-A3,
MAGE-C1, and/or
MAGE-C2, and b) wherein the further antigen(s) is (are) selected from at least one antigen as defined herein, preferably in any of the herein mentioned combinations, groups or subgroups of antigens, e.g. the further antigen(s) is (are) selected from, e.g.:
hTERT,
WT1,
MAGE-A2,
5T4,
MAGE-A3,
MUC1,
Her-2/neu,
NY-ESO-1,
CEA,
Survivin,
MAGE-C1, and/or
MAGE-C2.

Preferably, in the latter aspect, the at least one antigen(s) according to a) is (are) selected from:
NY-ESO-1,
MAGE-C1, and/or
MAGE-C2.

More preferably, in the latter aspect, the at least one antigen(s) according to a) is (are) selected from:
MAGE-C1, and/or
MAGE-C2.

Preferably, in the latter aspect, the at least one antigen(s) according to b) is (are) selected from an antigen (antigens) as defined in one of the following combinations:
hTERT and WT1; or
hTERT and MAGE-A2; or
hTERT and 5T4; or
hTERT and MAGE-A3; or
hTERT and MUC1; or
hTERT and Her-2/neu; or hTERT and NY-ESO-1; or
hTERT and CEA; or
hTERT and Survivin; or
hTERT and MAGE-C1; or
hTERT and MAGE-C2; or
WT1 and MAGE-A2; or
WT1 and 5T4; or
WT1 and MAGE-A3; or
WT1 and MUC1; or
WT1 and Her-2/neu; or
WT1 and NY-ESO-1; or
WT1 and CEA; or
WT1 and Survivin; or
WT1 and MAGE-C1; or
WT1 and MAGE-C2; or
MAGE-A2 and 5T4; or
MAGE-A2 and MAGE-A3; or
MAGE-A2 and MUC1; or
MAGE-A2 and Her-2/neu; or
MAGE-A2 and NY-ESO-1; or
MAGE-A2 and CEA; or
MAGE-A2 and Survivin; or
MAGE-A2 and MAGE-C1; or
MAGE-A2 and MAGE-C2; or
5T4 and MAGE-A3; or
5T4 and MUC1; or
5T4 and Her-2/neu; or
5T4 and NY-ESO-1; or
5T4 and CEA; or
5T4 and Survivin; or
5T4 and MAGE-C1; or
5T4 and MAGE-C2; or
MAGE-A3 and MUC1; or
MAGE-A3 and Her-2/neu; or
MAGE-A3 and NY-ESO-1; or
MAGE-A3 and CEA; or
MAGE-A3 and Survivin; or
MAGE-A3 and MAGE-C1
MAGE-A3 and MAGE-C2
MUC1 and Her-2/neu; or
MUC1 and NY-ESO-1; or
MUC1 and CEA; or
MUC1 and Survivin; or
MUC1 and MAGE-C1; or
MUC1 and MAGE-C2; or
HER-2/NEU and NY-ESO-1; or
HER-2/NEU and CEA; or
HER-2/NEU and Survivin; or
HER-2/NEU and MAGE-C1; or
HER-2/NEU and MAGE-C2; or
NY-ESO-1 and CEA; or
NY-ESO-1 and Survivin; or
NY-ESO-1 and MAGE-C1; or
NY-ESO-1 and MAGE-C2; or
CEA and Survivin; or
CEA and MAGE-C1; or
CEA and MAGE-C2; or
Survivin and MAGE-C1; or
Survivin and MAGE-C2; or
MAGE-C1 and MAGE-C2;
or
hTERT, WT1 and MAGE-A2; or
hTERT, WT1 and 5T4; or
hTERT, WT1 and MAGE-A3; or
hTERT, WT1 and MUC1; or
hTERT, WT1 and Her-2/neu; or
hTERT, WT1 and NY-ESO-1; or
hTERT, WT1 and CEA; or
hTERT, WT1 and Survivin; or
hTERT, WT1 and MAGE-C1; or
hTERT, WT1 and MAGE-C2; or
WT1, MAGE-A2 and 5T4; or
WT1, MAGE-A2 and MAGE-A3; or
WT1, MAGE-A2 and MUC1; or
WT1, MAGE-A2 and Her-2/neu; or
WT1, MAGE-A2 and NY-ESO-1; or
WT1, MAGE-A2 and CEA; or
WT1, MAGE-A2 and Survivin; or
WT1, MAGE-A2 and MAGE-C1; or
WT1, MAGE-A2 and MAGE-C2; or
MAGE-A2, 5T4 and MAGE-A3; or
MAGE-A2, 5T4 and MUC1; or
MAGE-A2, 5T4 and Her-2/neu; or
MAGE-A2, 5T4 and NY-ESO-1; or
MAGE-A2, 5T4 and CEA; or
MAGE-A2, 5T4 and Survivin; or
MAGE-A2, 5T4 and MAGE-C1; or
MAGE-A2, 5T4 and MAGE-C2; or
5T4, MAGE-A3 and MUC1; or
5T4, MAGE-A3 and Her-2/neu; or
5T4, MAGE-A3 and NY-ESO-1; or
5T4, MAGE-A3 and CEA; or
5T4, MAGE-A3 and Survivin; or
5T4, MAGE-A3 and MAGE-C1; or
5T4, MAGE-A3 and MAGE-C2; or
MAGE-A3, MUC1 and Her-2/neu; or
MAGE-A3, MUC1 and NY-ESO-1; or
MAGE-A3, MUC1 and CEA; or
MAGE-A3, MUC1 and Survivin; or
MAGE-A3, MUC1 and MAGE-C1; or
MAGE-A3, MUC1 and MAGE-C2; or
MUC1, Her-2/neu and NY-ESO-1; or
MUC1, Her-2/neu and CEA; or
MUC1, Her-2/neu and Survivin; or
MUC1, Her-2/neu and MAGE-C1; or
MUC1, Her-2/neu and MAGE-C2; or
HER-2/NEU, NY-ESO-1 and CEA; or
HER-2/NEU, NY-ESO-1 and Survivin; or
HER-2/NEU, NY-ESO-1 and MAGE-C1; or
HER-2/NEU, NY-ESO-1 and MAGE-C2; or
NY-ESO-1, CEA and Survivin; or
NY-ESO-1, CEA and MAGE-C1; or
NY-ESO-1, CEA and MAGE-C2; or
CEA, Survivin and MAGE-C1; or
CEA, Survivin and MAGE-C2; or
Survivin, MAGE-C1 and MAGE-C2;
or
hTERT, WT1, MAGE-A2 and 5T4; or
hTERT, WT1, MAGE-A2 and MAGE-A3; or
hTERT, WT1, MAGE-A2 and MUC1; or
hTERT, WT1, MAGE-A2 and Her-2/neu; or
hTERT, WT1, MAGE-A2 and NY-ESO-1; or
hTERT, WT1, MAGE-A2 and CEA; or
hTERT, WT1, MAGE-A2 and Survivin; or
hTERT, WT1, MAGE-A2 and MAGE-C1; or
hTERT, WT1, MAGE-A2 and MAGE-C2; or
WT1, MAGE-A2, 5T4 and MAGE-A3; or
WT1, MAGE-A2, 5T4 and MUC1; or
WT1, MAGE-A2, 5T4 and Her-2/neu; or
WT1, MAGE-A2, 5T4 and NY-ESO-1; or
WT1, MAGE-A2, 5T4 and CEA; or
WT1, MAGE-A2, 5T4 and Survivin; or
WT1, MAGE-A2, 5T4 and MAGE-C1; or
WT1, MAGE-A2, 5T4 and MAGE-C2; or MAGE-A2, 5T4, MAGE-A3 and MUC1; or
MAGE-A2, 5T4, MAGE-A3 and Her-2/neu; or
MAGE-A2, 5T4, MAGE-A3 and NY-ESO-1; or
MAGE-A2, 5T4, MAGE-A3 and CEA; or
MAGE-A2, 5T4, MAGE-A3 and Survivin; or
MAGE-A2, 5T4, MAGE-A3 and MAGE-C1; or
MAGE-A2, 5T4, MAGE-A3 and MAGE-C2; or
5T4, MAGE-A3, MUC1, and Her-2/neu; or
5T4, MAGE-A3, MUC1 and NY-ESO-1; or
5T4, MAGE-A3, MUC1 and CEA; or
5T4, MAGE-A3, MUC1 and Survivin; or
5T4, MAGE-A3, MUC1 and MAGE-C1; or
5T4, MAGE-A3, MUC1 and MAGE-C2; or
MAGE-A3, MUC1, Her-2/neu and NY-ESO-1; or
MAGE-A3, MUC1, Her-2/neu and CEA; or
MAGE-A3, MUC1, Her-2/neu and Survivin; or
MAGE-A3, MUC1, Her-2/neu and MAGE-C1; or
MAGE-A3, MUC1, Her-2/neu and MAGE-C2; or
MUC1, Her-2/neu, NY-ESO-1 and CEA; or
MUC1, Her-2/neu, NY-ESO-1 and Survivin; or
MUC1, Her-2/neu, NY-ESO-1 and MAGE-C1; or
MUC1, Her-2/neu, NY-ESO-1 and MAGE-C2; or
HER-2/NEU, NY-ESO-1, CEA and Survivin; or
HER-2/NEU, NY-ESO-1, CEA and MAGE-C1; or
HER-2/NEU, NY-ESO-1, CEA and MAGE-C2; or
NY-ESO-1, CEA, Survivin and MAGE-C1; or
NY-ESO-1, CEA, Survivin and MAGE-C2; or
CEA, Survivin, MAGE-C1 and MAGE-C2;
or
hTERT, WT1, MAGE-A2, 5T4 and MAGE-A3; or
hTERT, WT1, MAGE-A2, 5T4 and MUC1; or
hTERT, WT1, MAGE-A2, 5T4 and Her-2/neu; or
hTERT, WT1, MAGE-A2, 5T4 and NY-ESO-1; or
hTERT, WT1, MAGE-A2, 5T4 and CEA; or
hTERT, WT1, MAGE-A2, 5T4 and Survivin; or
hTERT, WT1, MAGE-A2, 5T4 and MAGE-C1; or
hTERT, WT1, MAGE-A2, 5T4 and MAGE-C2; or
WT1, MAGE-A2, 5T4, MAGE-A3 and MUC1; or
WT1, MAGE-A2, 5T4, MAGE-A3 and Her-2/neu; or
WT1, MAGE-A2, 5T4, MAGE-A3 and NY-ESO-1; or
WT1, MAGE-A2, 5T4, MAGE-A3 and CEA; or
WT1, MAGE-A2, 5T4, MAGE-A3 and Survivin; or
WT1, MAGE-A2, 5T4, MAGE-A3 and MAGE-C1; or
WT1, MAGE-A2, 5T4, MAGE-A3 and MAGE-C2; or
MAGE-A2, 5T4, MAGE-A3, MUC1 and Her-2/neu; or
MAGE-A2, 5T4, MAGE-A3, MUC1 and NY-ESO-1; or
MAGE-A2, 5T4, MAGE-A3, MUC1 and CEA; or
MAGE-A2, 5T4, MAGE-A3, MUC1 and Survivin; or
MAGE-A2, 5T4, MAGE-A3, MUC1 and MAGE-C1; or
MAGE-A2, 5T4, MAGE-A3, MUC1 and MAGE-C2; or
5T4, MAGE-A3, MUC1, Her-2/neu and NY-ESO-1; or
5T4, MAGE-A3, MUC1, Her-2/neu and CEA; or
5T4, MAGE-A3, MUC1, Her-2/neu and Survivin; or
5T4, MAGE-A3, MUC1, Her-2/neu and MAGE-C1; or
5T4, MAGE-A3, MUC1, Her-2/neu and MAGE-C2; or
MAGE-A3, MUC1, Her-2/neu, NY-ESO-1 and CEA; or
MAGE-A3, MUC1, Her-2/neu, NY-ESO-1 and Survivin; or
MAGE-A3, MUC1, Her-2/neu, NY-ESO-1 and MAGE-C1; or
MAGE-A3, MUC1, Her-2/neu, NY-ESO-1 and MAGE-C2; or
MUC1, Her-2/neu, NY-ESO-1, CEA and Survivin; or
MUC1, Her-2/neu, NY-ESO-1, CEA and MAGE-C1; or
MUC1, Her-2/neu, NY-ESO-1, CEA and MAGE-C2; or
HER-2/NEU, NY-ESO-1, CEA, Survivin and MAGE-C1; or
HER-2/NEU, NY-ESO-1, CEA, Survivin and MAGE-C2; or
NY-ESO-1, CEA, Survivin, MAGE-C1 and MAGE-C2; or
hTERT, WT1, MAGE-A2, 5T4, MAGE-A3 and MUC1; or
hTERT, WT1, MAGE-A2, 5T4, MAGE-A3 and Her-2/neu; or
hTERT, WT1, MAGE-A2, 5T4, MAGE-A3 and NY-ESO-1; or
hTERT, WT1, MAGE-A2, 5T4, MAGE-A3 and CEA; or
hTERT, WT1, MAGE-A2, 5T4, MAGE-A3 and Survivin; or
hTERT, WT1, MAGE-A2, 5T4, MAGE-A3 and MAGE-C1; or
hTERT, WT1, MAGE-A2, 5T4, MAGE-A3 and MAGE-C2; or
WT1, MAGE-A2, 5T4, MAGE-A3, MUC1 and Her-2/neu; or
WT1, MAGE-A2, 5T4, MAGE-A3, MUC1 and NY-ESO-1; or
WT1, MAGE-A2, 5T4, MAGE-A3, MUC1 and CEA; or
WT1, MAGE-A2, 5T4, MAGE-A3, MUC1 and Survivin; or
WT1, MAGE-A2, 5T4, MAGE-A3, MUC1 and MAGE-C1; or
WT1, MAGE-A2, 5T4, MAGE-A3, MUC1 and MAGE-C2; or
MAGE-A2, 5T4, MAGE-A3, MUC1, Her-2/neu and NY-ESO-1; or
MAGE-A2, 5T4, MAGE-A3, MUC1, Her-2/neu and CEA; or
MAGE-A2, 5T4, MAGE-A3, MUC1, Her-2/neu and Survivin; or
MAGE-A2, 5T4, MAGE-A3, MUC1, Her-2/neu and MAGE-C1; or
MAGE-A2, 5T4, MAGE-A3, MUC1, Her-2/neu and MAGE-C2; or
5T4, MAGE-A3, MUC1, Her-2/neu, NY-ESO-1 and CEA; or
5T4, MAGE-A3, MUC1, Her-2/neu, NY-ESO-1 and Survivin; or
5T4, MAGE-A3, MUC1, Her-2/neu, NY-ESO-1 and MAGE-C1; or
5T4, MAGE-A3, MUC1, Her-2/neu, NY-ESO-1 and MAGE-C2; or
MAGE-A3, MUC1, Her-2/neu, NY-ESO-1, CEA and Survivin; or
MAGE-A3, MUC1, Her-2/neu, NY-ESO-1, CEA and MAGE-C1;
or
MAGE-A3, MUC1, Her-2/neu, NY-ESO-1, CEA and MAGE-C2;
or
MUC1, Her-2/neu, NY-ESO-1, CEA, Survivin and MAGE-C1; or
MUC1, Her-2/neu, NY-ESO-1, CEA, Survivin and MAGE-C2; or
HER-2/NEU, NY-ESO-1, CEA, Survivin, MAGE-C1 and MAGE-C2;
or
hTERT, WT1, MAGE-A2, 5T4, MAGE-A3, MUC1 and Her-2/neu; or
hTERT, WT1, MAGE-A2, 5T4, MAGE-A3, MUC1 and NY-ESO-1; or
hTERT, WT1, MAGE-A2, 5T4, MAGE-A3, MUC1 and CEA; or hTERT, WT1, MAGE-A2, 5T4, MAGE-A3, MUC1 and Survivin; or
hTERT, WT1, MAGE-A2, 5T4, MAGE-A3, MUC1 and MAGE-C1; or
hTERT, WT1, MAGE-A2, 5T4, MAGE-A3, MUC1 and MAGE-C2; or
WT1, MAGE-A2, 5T4, MAGE-A3, MUC1, Her-2/neu and NY-ESO-1; or
WT1, MAGE-A2, 5T4, MAGE-A3, MUC1, Her-2/neu and CEA; or
WT1, MAGE-A2, 5T4, MAGE-A3, MUC1, Her-2/neu and Survivin; or
WT1, MAGE-A2, 5T4, MAGE-A3, MUC1, Her-2/neu and MAGE-C1; or
WT1, MAGE-A2, 5T4, MAGE-A3, MUC1, Her-2/neu and MAGE-C2; or
MAGE-A2, 5T4, MAGE-A3, MUC1, Her-2/neu, NY-ESO-1 and CEA; or
MAGE-A2, 5T4, MAGE-A3, MUC1, Her-2/neu, NY-ESO-1 and Survivin; or
MAGE-A2, 5T4, MAGE-A3, MUC1, Her-2/neu, NY-ESO-1 and MAGE-C1, or
MAGE-A2, 5T4, MAGE-A3, MUC1, Her-2/neu, NY-ESO-1 and MAGE-C2; or
5T4, MAGE-A3, MUC1, Her-2/neu, NY-ESO-1, CEA and Survivin; or
5T4, MAGE-A3, MUC1, Her-2/neu, NY-ESO-1, CEA and MAGE-C1; or
5T4, MAGE-A3, MUC1, Her-2/neu, NY-ESO-1, CEA and MAGE-C2; or
MAGE-A3, MUC1, Her-2/neu, NY-ESO-1, CEA, Survivin and MAGE-C1; or
MAGE-A3, MUC1, Her-2/neu, NY-ESO-1, CEA, Survivin and MAGE-C2; or
MUC1, Her-2/neu, NY-ESO-1, CEA, Survivin, MAGE-C1 and MAGE-C2; or
hTERT, WT1, MAGE-A2, 5T4, MAGE-A3, MUC1, Her-2/neu and NY-ESO-1; or
hTERT, WT1, MAGE-A2, 5T4, MAGE-A3, MUC1, Her-2/neu and CEA; or
hTERT, WT1, MAGE-A2, 5T4, MAGE-A3, MUC1, Her-2/neu and Survivin; or
hTERT, WT1, MAGE-A2, 5T4, MAGE-A3, MUC1, Her-2/neu and MAGE-C1; or
hTERT, WT1, MAGE-A2, 5T4, MAGE-A3, MUC1, Her-2/neu and MAGE-C2; or
WT1, MAGE-A2, 5T4, MAGE-A3, MUC1, Her-2/neu, NY-ESO-1 and CEA; or
WT1, MAGE-A2, 5T4, MAGE-A3, MUC1, Her-2/neu, NY-ESO-1 and Survivin; or
WT1, MAGE-A2, 5T4, MAGE-A3, MUC1, Her-2/neu, NY-ESO-1 and MAGE-C1; or
WT1, MAGE-A2, 5T4, MAGE-A3, MUC1, Her-2/neu, NY-ESO-1 and MAGE-C2; or
MAGE-A2, 5T4, MAGE-A3, MUC1, Her-2/neu, NY-ESO-1, CEA and Survivin; or
MAGE-A2, 5T4, MAGE-A3, MUC1, Her-2/neu, NY-ESO-1, CEA and MAGE-C1; or
MAGE-A2, 5T4, MAGE-A3, MUC1, Her-2/neu, NY-ESO-1, CEA and MAGE-C2; or
5T4, MAGE-A3, MUC1, Her-2/neu, NY-ESO-1, CEA, Survivin and MAGE-C1; or
5T4, MAGE-A3, MUC1, Her-2/neu, NY-ESO-1, CEA, Survivin and MAGE-C2; or
MAGE-A3, MUC1, Her-2/neu, NY-ESO-1, CEA, Survivin, MAGE-C1 and MAGE-C2;
or
hTERT, WT1, MAGE-A2, 5T4, MAGE-A3, MUC1, Her-2/neu, NY-ESO-1 and CEA; or
hTERT, WT1, MAGE-A2, 5T4, MAGE-A3, MUC1, Her-2/neu, NY-ESO-1 and Survivin; or
hTERT, WT1, MAGE-A2, 5T4, MAGE-A3, MUC1, Her-2/neu, NY-ESO-1 and MAGE-C1; or
hTERT, WT1, MAGE-A2, 5T4, MAGE-A3, MUC1, Her-2/neu, NY-ESO-1 and MAGE-C2; or
WT1, MAGE-A2, 5T4, MAGE-A3, MUC1, Her-2/neu, NY-ESO-1, CEA and Survivin; or
WT1, MAGE-A2, 5T4, MAGE-A3, MUC1, Her-2/neu, NY-ESO-1, CEA and MAGE-C1; or
WT1, MAGE-A2, 5T4, MAGE-A3, MUC1, Her-2/neu, NY-ESO-1, CEA and MAGE-C2; or
MAGE-A2, 5T4, MAGE-A3, MUC1, Her-2/neu, NY-ESO-1, CEA, Survivin and MAGE-C1; or
MAGE-A2, 5T4, MAGE-A3, MUC1, Her-2/neu, NY-ESO-1, CEA, Survivin and MAGE-C2; or
5T4, MAGE-A3, MUC1, Her-2/neu, NY-ESO-1, CEA, Survivin, MAGE-C1 and MAGE-C2;
or
hTERT, WT1, MAGE-A2, 5T4, MAGE-A3, MUC1, Her-2/neu, NY-ESO-1, CEA and Survivin; or
hTERT, WT1, MAGE-A2, 5T4, MAGE-A3, MUC1, Her-2/neu, NY-ESO-1, CEA and MAGE-C1; or
hTERT, WT1, MAGE-A2, 5T4, MAGE-A3, MUC1, Her-2/neu, NY-ESO-1, CEA and MAGE-C2; or
WT1, MAGE-A2, 5T4, MAGE-A3, MUC1, Her-2/neu, NY-ESO-1, CEA, Survivin and MAGE-C1; or
WT1, MAGE-A2, 5T4, MAGE-A3, MUC1, Her-2/neu, NY-ESO-1, CEA, Survivin and MAGE-C2; or
MAGE-A2, 5T4, MAGE-A3, MUC1, Her-2/neu, NY-ESO-1, CEA, Survivin, MAGE-C1 and MAGE-C2;
or
hTERT, WT1, MAGE-A2, 5T4, MAGE-A3, MUC1, Her-2/neu, NY-ESO-1, CEA, Survivin and MAGE-C1; or
hTERT, WT1, MAGE-A2, 5T4, MAGE-A3, MUC1, Her-2/neu, NY-ESO-1, CEA, Survivin and MAGE-C2; or
WT1, MAGE-A2, 5T4, MAGE-A3, MUC1, Her-2/neu, NY-ESO-1, CEA, Survivin, MAGE-C1 and MAGE-C2;
or
hTERT, WT1, MAGE-A2, 5T4, MAGE-A3, MUC1, Her-2/neu, NY-ESO-1, CEA, Survivin, MAGE-C1 and MAGE-C2.

More preferably, in the latter aspect, the at least one antigen(s) according to b) is (are) selected from the following combination:

Survivin and 5T4

In the above embodiments, each of the at least two (preferably different) antigens as defined herein may be encoded by one (monocistronic) RNA, preferably one (monocistronic) mRNA. In other words, the nucleic acid (sequence) of the inventive solution for lyophilization, transfection and/or injection may comprise at least two (monocistronic) RNAs, preferably mRNAs, wherein each of these at least two (monocistronic) RNAs, preferably mRNAs, may encode just one (preferably different) antigen, preferably selected from one of the above mentioned combinations.

According to another particularly preferred aspect, the nucleic acid (sequence) of the inventive solution for lyophilization, transfection and/or injection may comprise (at least) one bi- or even multicistronic RNA, preferably mRNA, i.e. (at least) one RNA which carries two or even more of the coding sequences of at the least two (preferably different) antigens, preferably selected from one of the above mentioned combinations. Such coding sequences of the at least two (preferably different) antigens of the (at least) one bi- or even multicistronic RNA may be separated by at least one IRES (internal ribosomal entry site) sequence, as defined below. Thus, the term "encoding at least two (preferably different) antigens" may mean, without being limited thereto, that the (at least) one (bi- or even multicistronic) RNA, preferably a mRNA, may encode e.g. at least two, three, four, five, six, seven, eight, nine, ten, eleven or twelve (preferably different) antigens of the above mentioned group(s) of antigens or their fragments or variants. More preferably, without being limited thereto, the (at least) one (bi- or even multicistronic) RNA, preferably mRNA, may encode e.g. at least two, three, four, five or six (preferably different) antigens of the above mentioned subgroup(s) of antigens or their fragments or variants within the above definitions. In this context, a so-called IRES (internal ribosomal entry site) sequence as defined above can function as a sole ribosome binding site, but it can also serve to provide a bi- or even multicistronic RNA as defined above which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further particularly preferred aspect, the nucleic acid (sequence) of the inventive solution for lyophilization, transfection and/or injection may comprise a mixture of at least one monocistronic RNA, preferably mRNA, as defined above, and at least one bi- or even multicistronic RNA, preferably mRNA, as defined above. The at least one monocistronic RNA and/or the at least one bi- or even multicistronic RNA preferably encode different antigens or their fragments or variants, the antigens preferably being selected from one of the above mentioned groups or subgroups of antigens, more preferably in one of the above mentioned combinations. However, the at least one monocistronic RNA and the at least one bi- or even multicistronic RNA may preferably also encode (in part) identical antigens selected from one of the above mentioned groups or subgroups of antigens, preferably in one of the above mentioned combinations, provided that the nucleic acid (sequence) of the inventive solution for lyophilization, transfection and/or injection as a whole provides at least two (preferably different) antigens as defined above. Such an aspect may be advantageous e.g. for a staggered, e.g. time dependent, administration of the inventive solution for lyophilization, transfection and/or injection, e.g. as a pharmaceutical composition, as a vaccine, a lyophilized nucleic acid, etc., to a patient in need thereof. The components of a pharmaceutical composition, as a vaccine, a lyophilized nucleic acid, etc., particularly the different RNAs encoding the at least two (preferably different) antigens, may be e.g. contained in (different parts of) a kit of parts composition or may be e.g. administered separately as components of different pharmaceutical compositions, vaccines, lyophilized nucleic acids, etc.

According to another aspect, one further class of antigens as encoded by the nucleic acid (sequence) of the inventive solution for lyophilization, transfection and/or injection comprises allergy antigens. Such allergy antigens may be selected from antigens derived from different sources, e.g. from animals, plants, fungi, bacteria, etc. Allergens in this context include e.g. grasses, pollens, molds, drugs, or numerous environmental triggers, etc. Allergy antigens typically belong to different classes of compounds, such as nucleic acids and their fragments, proteins or peptides and their fragments, carbohydrates, polysaccharides, sugars, lipids, phospholipids, etc. Of particular interest in the context of the present invention are antigens, which may be encoded by the nucleic acid (sequence) of the inventive solution for lyophilization, transfection and/or injection, i.e. protein or peptide antigens and their fragments or epitopes, or nucleic acids and their fragments, particularly nucleic acids and their fragments, encoding such protein or peptide antigens and their fragments or epitopes.

Particularly preferred, antigens derived from animals, which may be encoded by the nucleic acid (sequence) of the inventive solution for lyophilization, transfection and/or injection may include antigens derived from, without being limited thereto, insects, such as mite (e.g. house dust mites), mosquito, bee (e.g. honey bee, bumble bee), cockroach, tick, moth (e.g. silk moth), midge, bug, flea, wasp, caterpillar, fruit fly, migratory locust, grasshopper, ant aphide, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form molluscs, such as scallop, octopus, abalone, snail, whelk, squid, clam, mussel, from spiders, from mammals, such as cow, rabbit, sheep, lion, jaguar, leopard, rat, pig, buffalo, dog, loris, hamster, guinea pig, fallow deer, horse, cat, mouse, ocelot, serval, from arthropod, such as spider, or silverfish, from worms, such as nematodes, from *trichinella* species, or roundworm, from amphibians, such as frogs, or from sea squirt, etc.

Antigens derived from plants, which may be encoded by the nucleic acid (sequence) of the inventive solution for lyophilization, transfection and/or injection may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumpkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc.

Antigens derived from fungi, which may be encoded by the nucleic acid (sequence) of the inventive solution for lyophilization, transfection and/or injection may include antigens derived from, without being limited thereto, e.g. *Alternia* sp., *Aspergillus* sp., *Beauveria* sp., *Candida* sp.,

*Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria, which may be encoded by the nucleic acid (sequence) of the inventive solution for lyophilization, transfection and/or injection may include antigens derived from, without being limited thereto, e.g. *Bacillus tetani, Staphylococcus aureus, Streptomyces griseus*, etc.

c) Antibodies

According to a further alternative, the nucleic acid (sequence) of the inventive solution for lyophilization, transfection and/or injection may encode an antibody. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general; an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$. Single chain antibodies may be encoded by the lyophilized nucleic acid according to the present invention as well.

According to a first alternative, the nucleic acid (sequence) of the inventive solution for lyophilization, transfection and/or injection may encode a polyclonal antibody. In this context, the term, "polyclonal antibody" typically means mixtures of antibodies directed to specific antigens or immunogens or epitopes of a protein which were generated by immunization of a host organism, such as a mammal, e.g. including goat, cattle, swine, dog, cat, donkey, monkey, ape, a rodent such as a mouse, hamster and rabbit. Polyclonal antibodies are generally not identical, and thus usually recognize different epitopes or regions from the same antigen. Thus, in such a case, typically a mixture (a composition) of different at least one nucleic acid (sequence) of the inventive solution for lyophilization, transfection and/or injection will be used, each lyophilized nucleic acid encoding a specific (monoclonal) antibody being directed to specific antigens or immunogens or epitopes of a protein.

According to a further alternative, the nucleic acid (sequence) of the inventive solution for lyophilization, transfection and/or injection may encode a monoclonal antibody. The term "monoclonal antibody" herein typically refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed to a single antigenic site. Furthermore, in contrast to conventional (polyclonal) antibody preparations which typically include different antibodies directed to different determinants (epitopes), each monoclonal antibody is directed to a single determinant on the antigen. For example, monoclonal antibodies as defined above may be made by the hybridoma method first described by Kohler and Milstein, Nature, 256:495 (1975), or may be made by recombinant DNA methods, e.g. as described in U.S. Pat. No. 4,816,567. "Monoclonal antibodies" may also be isolated from phage libraries generated using the techniques described in McCafferty et al., Nature, 348:552-554 (1990), for example. According to Kohler and Milstein, an immunogen (antigen) of interest is injected into a host such as a mouse and B-cell lymphocytes produced in response to the immunogen are harvested after a period of time. The B-cells are combined with myeloma cells obtained from mouse and introduced into a medium which permits the B-cells to fuse with the myeloma cells, producing hybridomas. These fused cells (hybridomas) are then placed into separate wells of microtiter plates and grown to produce monoclonal antibodies. The monoclonal antibodies are tested to determine which of them are suitable for detecting the antigen of interest. After being selected, the monoclonal antibodies can be grown in cell cultures or by injecting the hybridomas into mice. However, for the purposes of the present invention, the peptide sequences of these monoclonal antibodies have to be sequenced and the at least one nucleic acid (sequence) encoding these antibodies can be present as the nucleic acid (sequence) of the inventive solution for lyophilization, transfection and/or injection.

For therapeutical purposes in humans, non-human monoclonal or polyclonal antibodies, such as murine antibodies may also be encoded by the nucleic acid (sequence) of the inventive solution for lyophilization, transfection and/or injection. However, such antibodies are typically only of limited use, since they generally induce an immune response by production of human antibodies directed to the said non-human antibodies, in the human body. Therefore, a particular non-human antibody can only be administered once to the human. To solve this, problem, chimeric, humanized non-human and human antibodies are also envisaged encoded by the nucleic acid (sequence) of the inventive solution for lyophilization, transfection and/or injection. "Chimeric" antibodies, which may be encoded by the nucleic acid (sequence) of the inventive solution for lyophilization, transfection and/or injection are preferably antibodies in which the constant domains of an antibody described above are replaced by sequences of antibodies from other organisms, preferably human sequences. "Humanized" (non-human) antibodies, which may be also encoded by the nucleic acid (sequence) of the inventive solution for lyophilization, transfection and/or injection are antibodies in which the constant and variable domains (except for the hypervariable domains) described above of an antibody are replaced by human sequences. According to another alternative, the nucleic acid (sequence) of the inventive solution for lyophilization, transfection and/or injection may encode human antibodies, i.e. antibodies having only human sequences. Such human antibodies can be isolated from human tissues or from immunized non-human host organisms which are transgene for the human IgG gene locus, and at least one nucleic acid (sequence) may be prepared according to procedures well known in the art.

Additionally, human antibodies can be provided by the use of a phage display.

In addition, the nucleic acid (sequence) of the inventive solution for lyophilization, transfection and/or injection may encode bispecific antibodies. "Bispecific" antibodies in context of the invention are preferably antibodies which act as an adaptor between an effector and a respective target by two different $F_{a/b}$-domains, e.g. for the purposes of recruiting effector molecules such as toxins, drugs, cytokines etc., targeting effector cells such as CTL, NK cells, makrophages, granulocytes, etc. (see for review: Kontermann R. E., Acta Pharmacol. Sin, 2005, 26(1): 1-9). Bispecific antibodies as described herein are, in general, configured to recognize by two different $F_{a/b}$-domains, e.g. two different antigens, immunogens, epitopes, drugs, cells (or receptors on cells), or other molecules (or structures) as described above. Bispecificity means herewith that the antigen-binding regions of the antibodies are specific for two different epitopes. Thus, different antigens, immunogens or epitopes, etc. can be brought close together, what, optionally, allows a direct interaction of the two components. For example, different cells such as effector cells and target cells can be connected via a bispecific antibody. Encompassed, but not limited, by the present invention are antibodies or fragments thereof which bind, on the one hand, a soluble antigen as described herein, and, on the other hand, an antigen or receptor on the surface of a tumor cell.

According to the invention, the nucleic acid (sequence) of the inventive solution for lyophilization, transfection and/or injection may also encode intrabodies, wherein these intrabodies may be antibodies as defined above. Since these antibodies are intracellular expressed antibodies, i.e. antibodies which may be encoded by nucleic acids localized in specific areas of the cell and also expressed there, such antibodies may be termed intrabodies.

Antibodies as encoded by the nucleic acid (sequence) of the inventive solution for lyophilization, transfection and/or injection may preferably comprise full-length antibodies, i.e. antibodies composed of the full heavy and full light chains, as described above. However, derivatives of antibodies such as antibody fragments, variants or adducts may also be encoded by the nucleic acid (sequence) of the inventive solution for lyophilization, transfection and/or injection.

The nucleic acid (sequence) of the inventive solution for lyophilization, transfection and/or injection may also encode antibody fragments selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

According to a further alternative, the nucleic acid (sequence) of the inventive solution for lyophilization, transfection and/or injection may be in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Rev. Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The nucleic acid (sequence) of the inventive solution for lyophilization, transfection and/or injection may thus be a double-stranded RNA (dsRNA) having a length of from 17 to 29, preferably from 19 to 25, and preferably being at least 90%, more preferably 95% and especially 100% (of the nucleotides of a dsRNA) complementary to a section of the nucleic acid (sequence) of a (therapeutically relevant) protein or antigen described (as active ingredient) hereinbefore, either a coding or a non-coding section, preferably a coding section. 90% complementary means that with a length of a dsRNA described herein of, for example, 20 nucleotides, this contains not more than 2 nucleotides without corresponding complementarity with the corresponding section of the mRNA. The sequence of the double-stranded RNA used according to the invention is, however, preferably wholly complementary in its general structure with a section of the nucleic acid of a therapeutically relevant protein or antigen described hereinbefore. In this context the nucleic acid (sequence) of the inventive solution for lyophilization, transfection and/or injection may be a dsRNA having the general structure 5'-($N_{17-29}$)-3', preferably having the general structure 5'-($N_{19-25}$)-3', more preferably having the general structure 5'-($N_{19-24}$)-3', or yet more preferably having the general structure 5'-($N_{21-23}$)-3', wherein for each general structure each N is a (preferably different) nucleotide of a section of the mRNA of a therapeutically relevant protein or antigen described hereinbefore, preferably being selected from a continuous number of 17 to 29 nucleotides of the mRNA of a therapeutically relevant protein or antigen and being present in the general structure 5'-($N_{17-29}$)-3' in their natural order. In principle, all the sections having a length of from 17 to 29, preferably from 19 to 25, base pairs that occur in the mRNA can serve as target sequence for a dsRNA herein. Equally, dsRNAs used as nucleic acid (sequence) of the inventive solution for lyophilization, transfection and/or injection can also be directed against nucleotide sequences of a (therapeutically relevant) protein or antigen described (as active ingredient) hereinbefore that do not lie in the coding region, in particular in the 5' non-coding region of the mRNA, for example, therefore, against non-coding regions of the mRNA having a regulatory function. The target sequence of the dsRNA used as nucleic acid (sequence) of the inventive solution for lyophilization, transfection and/or injection can therefore lie in the translated and untranslated region of the mRNA and/or in the region of the control elements of a protein or antigen described hereinbefore. The target sequence of a dsRNA used as the nucleic acid (sequence) of the inventive solution for lyophilization, transfection and/or injection can also lie in the overlapping region of untranslated and translated sequence; in particular, the target sequence can comprise at least one nucleotide upstream of the start triplet of the coding region of the mRNA.

According to another alternative, the nucleic acid (sequence) of the inventive solution for lyophilization, transfection and/or injection may be in the form of a CpG nucleic acid, in particular CpG-RNA or CpG-DNA. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

Likewise, according to a further alternative, the nucleic acid (sequence) of the inventive solution for lyophilization, transfection and/or injection may be in the form of an immunostimulatory RNA. Such an immunostimulatory RNA used as the nucleic acid (sequence) of the inventive solution for lyophilization, transfection and/or injection may be any (double-stranded or single-stranded) RNA, e.g. a coding RNA, as defined above. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a ((linear) single-stranded) messenger RNA (mRNA). An immunostimulatory RNA may also occur as a short RNA oligonucleotide as defined above. An immunostimulatory RNA as used herein may furthermore be selected from any class of RNA molecules, found in nature or being prepared synthetically, and which can induce an immune response. In this context, an immune response may occur in various ways. A substantial factor for a suitable immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of great importance in the immune response. In connection with the present invention, the Th1/Th2 ratio of the immune response is preferably shifted in the direction towards the cellular response (Th1 response) and a cellular immune response is thereby induced. According to one example, the immune system may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl Acad Sci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

According to the present invention, it was found that any RNA (molecule) as e.g. defined above (irrespective of its specific length, strandedness, modification and/or nucleotide sequence) may have immunostimulatory properties, i.e. enhance the immune response. An RNA as defined above and being the nucleic acid (sequence) of the inventive solution for lyophilization, transfection and/or injection may thus be used to enhance (unspecific) immunostimulation, if suitable and desired for a specific treatment.

The at least one (immunostimulatory) RNA (molecule) used as the nucleic acid (sequence) of the inventive solution for lyophilization, transfection and/or injection may thus comprise any RNA sequence known to be immunostimulatory, including, without being limited thereto, RNA sequences representing and/or encoding ligands of TLRs, preferably selected from family members TLR1-TLR13, more preferably from TLR7 and TLR8, ligands for intracellular receptors for RNA (such as RIG-I or MAD-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence. Furthermore, (classes of) immunostimulatory RNA molecules, used as the nucleic acid (sequence) of the inventive solution for lyophilization, transfection and/or injection may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA).

Such further (classes of) immunostimulatory RNA molecules, which may be used as the nucleic acid (sequence) of the inventive solution for lyophilization, transfection and/or injection, without being limited thereto, may comprise e.g. an RNA molecule of formula (I):

$$G_l X_m G_n,$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein when l=1 G is guanosine or an analogue thereof,
  when l>1 at least 50% of the nucleotides are guanosine or an analogue thereof;
m is an integer and is at least 3;
  wherein when m=3 X is uracil or an analogue thereof,
  when m>3 at least 3 successive uracils or analogues of uracil occur;
n is an integer from 1 to 40,
  wherein when n=1 G is guanosine or an analogue thereof,
  when n>1 at least 50% of the nucleotides are guanosine or an analogue thereof.

In addition, such further (classes of) immunostimulatory RNA molecules, which may be used as the nucleic acid (sequence) of the inventive solution for lyophilization, transfection and/or injection may comprise, without being limited thereto, e.g. an RNA molecule of formula (II):

$C_lX_mC_n$, wherein:

C is cytosine, uracil or an analogue of cytosine or uracil;

X is guanosine, uracil, adenosine, thymidine, cytosine or an analogue of the above-mentioned nucleotides;

l is an integer from 1 to 40,
wherein when l=1 C is cytosine or an analogue thereof,
when l>1 at least 50% of the nucleotides are cytosine or an analogue
thereof;

m is an integer and is at least 3;
wherein when m=3 X is uracil or an analogue thereof,
when m>3 at least 3 successive uracils or analogues of uracil occur;

n is an integer from 1 to 40,
wherein when n=1 C is cytosine or an analogue thereof,
when n>1 at least 50% of the nucleotides are cytosine or an analogue
thereof.

Preferably, the immunostimulatory RNA molecules used as the nucleic acid (sequence) of the inventive solution for lyophilization, transfection and/or injection may comprise a length as defined above in general for RNA molecules of the RNA of the present invention, more preferably a length of 5 to 5000, of 500 to 5000 or, more preferably, of 1000 to 5000 or, alternatively, of 5 to 1000, 5 to 500, 5 to 250, of 5 to 100, of 5 to 50 or, more preferably, of 5 to 30 nucleotides.

The immunostimulatory RNA used as the nucleic acid (sequence) of the inventive solution for lyophilization, transfection and/or injection may be furthermore modified, preferably "chemically modified" in order to enhance the immunostimulatory properties of said RNA. The term "chemical modification" means that the immuostimulatory RNA is modified by replacement, insertion or removal of individual or several atoms or atomic groups compared with naturally occurring RNA species.

Preferably, the chemical modification of the immunostimulatory RNA comprises at least one analogue of naturally occurring nucleotides. In a list which is in no way conclusive, examples which may be mentioned for nucleotide analogues and which may be used herein for modification are analogues of guanosine, uracil, adenosine, thymidine, cytosine. The modifications may refer to modifications of the base, the ribose moiety and/or the phosphate backbone moiety. In this context, analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N-6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluorouridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642. In the case of an analogue as described above, particular preference is given according to the invention to those analogues that increase the immunogenicity of the immunostimulatory RNA sequence used as the nucleic acid (sequence) of the inventive solution for lyophilization, transfection and/or injection and/or do not interfere with a further modification that has been introduced into said immunostimulatory RNA.

In general, the nucleic acid (sequence) of the inventive solution for lyophilization, transfection and/or injection as defined above may also occur in the form of a modified nucleic acid, wherein any modification, as defined herein, may be introduced into the nucleic acid prior to lyophilization, transfection and/or injection. Modifications as defined herein preferably lead to a further stabilized nucleic acid as defined herein.

According to a first aspect, the nucleic acid (sequence) of the inventive solution for lyophilization, transfection and/or injection may thus be provided as a "stabilized nucleic acid", preferably as a stabilized RNA, more preferably as an RNA that is essentially resistant to in vivo degradation (e.g. by an exo- or endo-nuclease). Such stabilization can be effected, for example, by a modified phosphate backbone of the nucleic acid (sequence) of the inventive solution for lyophilization, transfection and/or injection. A backbone modification in connection with the present invention is a modification in which phosphates of the backbone of the nucleotides contained in the nucleic acid (sequence) of the inventive solution for lyophilization, transfection and/or injection are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized at least one nucleic acid (sequence) of the inventive solution for lyophilization, transfection and/or injection may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

The nucleic acid (sequence) of the inventive solution for lyophilization, transfection and/or injection may additionally or alternatively also contain sugar modifications. A sugar modification in connection with the present invention is a chemical modification of the sugar of the nucleotides of the nucleic acid (sequence) of the inventive solution for lyophilization, transfection and/or injection typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), or azidotriphosphate (2'-azido-2'-deoxycytidine-5'-triphosphate, 2'-azido-2'-deoxyuridine-5'-triphosphate).

The nucleic acid (sequence) of the inventive solution for lyophilization, transfection and/or injection may additionally or alternatively also contain at least one base modification, which is preferably suitable for increasing the expression of the protein coded for by the lyophilized nucleic acid as compared with the unaltered, i.e. natural (=native), nucleic acid (sequence). Significant in this case means an increase in the expression of the protein compared with the expression of the native nucleic acid (sequence) by at least 20%, preferably at least 30%, 40%, 50% or 60%, more preferably by at least 70%, 80%, 90% or even 100% and most preferably by at least 150%, 200% or even 300% or more. In connection with the present invention, a nucleotide having such a base modification is preferably selected from the group of the base-modified nucleotides consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to another aspect, the nucleic acid (sequence) of the inventive solution for lyophilization, transfection and/or injection can likewise be modified (and preferably stabilized) by introducing further modified nucleotides containing modifications of their ribose or base moieties. Generally, the nucleic acid (sequence) of the inventive solution for lyophilization, transfection and/or injection may contain any native (=naturally occurring) nucleotide, e.g. guanosine, uracil, adenosine, and/or cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the nucleic acid sequence. Exemplary analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluorouridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642. In the case of an analogue as described above, particular preference may be given according to the invention to those analogues that do not interfere with a further modification of the nucleic acid (sequence) of the inventive solution for lyophilization, transfection and/or injection that has been introduced.

According to a particular aspect, the nucleic acid (sequence) of the inventive solution for lyophilization, transfection and/or injection can contain a lipid modification. Such a lipid-modified nucleic acid typically comprises a nucleic acid as defined herein. Such a lipid-modified nucleic acid (sequence) of the inventive solution for lyophilization, transfection and/or injection typically further comprises at least one linker covalently linked with that nucleic acid, and at least one lipid covalently linked with the respective linker. Alternatively, the lipid-modified nucleic acid comprises an at least one nucleic acid as defined herein and at least one (bifunctional) lipid covalently linked (without a linker) with that nucleic acid. According to a third alternative, the lipid-modified nucleic acid comprises a nucleic acid RNA as defined herein, at least one linker covalently linked with that nucleic acid, and at least one lipid covalently linked with the respective linker, and also at least one (bifunctional) lipid covalently linked (without a linker) with that nucleic acid.

The lipid, which may be contained in the nucleic acid (sequence) of the inventive solution for lyophilization, transfection and/or injection (complexed or covalently bound thereto) is typically a lipid or a lipophilic residue that preferably is itself biologically active. Such lipids preferably include natural substances or compounds such as, for example, vitamins, e.g. alpha-tocopherol (vitamin E), including RRR-alpha-tocopherol (formerly D-alpha-tocopherol), L-alpha-tocopherol, the racemate D,L-alpha-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present invention include, without implying any limitation, polyalkylene glycols (Oberhauser et al., Nucl. Acids Res., 1992, 20, 533), aliphatic groups such as, for example, C1-C20-alkanes, C1-C20-alkenes or C1-C20-alkanol compounds, etc., such as, for example, dodecanediol, hexadecanol or undecyl residues (Saison-Behmoaras et al., EMBO J, 1991, 10, 111; Kabanov et al., FEBS Lett., 1990, 259, 327; Svinarchuk et al., Biochimie, 1993, 75, 49), phospholipids such as, for example, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as, for example, polyethylene glycol (PEG) (Manoharan et al., Nucleosides & Nucleotides, 1995, 14, 969), hexaethylene glycol (HEG), palmitin or palmityl residues (Mishra et al., Biochim. Biophys. Acta, 1995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

The nucleic acid (sequence) of the inventive solution for lyophilization, transfection and/or injection may likewise be stabilized in order to prevent degradation of the nucleic acid by various approaches, particularly, when RNA or mRNA is used as a nucleic acid for the inventive purpose. It is known in the art that instability and (fast) degradation of mRNA or of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of mRNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

The nucleic acid (sequence) of the inventive solution for lyophilization, transfection and/or injection, particularly if provided as a mRNA, can therefore be stabilized against degradation by RNases by the addition of a so-called "5' cap" structure. Particular preference is given in this connection to an m7G(5')ppp (5'(A,G(5')ppp(5')A or G(5')ppp(5')G as the 5' cap" structure. However, such a modification is introduced only if a modification, for example a lipid modification, has not already been introduced at the 5' end of the nucleic acid (sequence) of the inventive solution for lyophilization, transfection and/or injection, if provided as a mRNA or if the modification does not interfere with the immunogenic properties of the (unmodified or chemically modified) nucleic acid (sequence) of the inventive solution for lyophilization, transfection and/or injection.

According to a further preferred aspect, the nucleic acid (sequence) of the inventive solution for lyophilization, transfection and/or injection may contain, especially if the nucleic acid is in the form of a mRNA, a poly-A tail on the 3' terminus of typically about 10 to 200 adenosine nucleotides, preferably about 10 to 100 adenosine nucleotides, more preferably about 20 to 100 adenosine nucleotides or even more preferably about 40 to 80 adenosine nucleotides.

According to a further preferred aspect, the nucleic acid (sequence) of the inventive solution for lyophilization, transfection and/or injection may contain, especially if the nucleic acid is in the form of a mRNA, a poly-C tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

According to another aspect, the nucleic acid (sequence) of the inventive solution for lyophilization, transfection and/or injection may be modified, and thus stabilized, especially if the nucleic acid is in the form of a mRNA, by modifying the G/C content of the nucleic acid, particularly an mRNA, preferably of the coding region thereof.

In a particularly preferred aspect of the present invention, the G/C content of the coding region of the nucleic acid (sequence) of the inventive solution for lyophilization, transfection and/or injection, especially if the nucleic acid is in the form of a mRNA, is modified, particularly increased, compared to the G/C content of the coding region of its particular wild type mRNA, i.e. the unmodified mRNA. The encoded amino acid sequence of the at least one mRNA is preferably not modified compared to the coded amino acid sequence of the particular wild type mRNA.

This modification of the nucleic acid (sequence) of the inventive solution for lyophilization, transfection and/or injection, especially if the nucleic acid is in the form of a mRNA, is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the mRNA are therefore varied compared to its wild type mRNA, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage).

Depending on the amino acid to be encoded by the nucleic acid (sequence) of the inventive solution for lyophilization, transfection and/or injection, especially if the nucleic acid is in the form of a mRNA, there are various possibilities for modification of the at least one mRNA sequence, compared to its wild type sequence. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codon for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the nucleic acid (sequence) of the inventive solution for lyophilization, transfection and/or injection, especially if the nucleic acid is in the form of a mRNA, compared to its particular wild type mRNA (i.e. the original sequence). Thus, for example, all codons for Thr occurring in the wild type sequence can be modified to ACC (or ACG). Preferably, however, for example, combinations of the above substitution possibilities are used:
substitution of all codons coding for Thr in the original sequence (wild type mRNA) to ACC (or ACG) and
substitution of all codons originally coding for Ser to UCC (or UCG or AGC);
substitution of all codons coding for Ile in the original sequence to AUC and
substitution of all codons originally coding for Lys to AAG and
substitution of all codons originally coding for Tyr to UAC;
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Arg to CGC (or CGG);
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Gly to GGC (or GGG) and
substitution of all codons originally coding for Asn to AAC;
substitution of all codons coding for Val in the original sequence to GUC (or GUG) and
substitution of all codons originally coding for Phe to UUC and
substitution of all codons originally coding for Cys to UGC and
substitution of all codons originally coding for Leu to CUG (or CUC) and
substitution of all codons originally coding for Gln to CAG and
substitution of all codons originally coding for Pro to CCC (or CCG); etc.

Preferably, the G/C content of the coding region of the nucleic acid (sequence) of the inventive solution for lyophilization, transfection and/or injection, especially if the nucleic acid is in the form of a mRNA, is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence are substituted, thereby increasing the GC/content of said sequence.

In this context, it is particularly preferable to increase the G/C content of the nucleic acid (sequence) of the inventive solution for lyophilization, transfection and/or injection, especially if the nucleic acid is in the form of a mRNA, to the maximum (i.e. 100% of the substitutable codons), in particular in the region coding for a protein, compared to the wild type sequence.

According to the invention, a further preferred modification of the nucleic acid (sequence) of the inventive solution for lyophilization, transfection and/or injection, especially if the nucleic acid is in the form of a mRNA, is based on the finding that the translation efficiency is also determined by a different frequency in the occurrence of tRNAs in cells. Thus, if so-called "rare codons" are present in the nucleic acid (sequence) of the inventive solution for lyophilization, transfection and/or injection, especially if the nucleic acid is in the form of a mRNA, to an increased extent, the corresponding modified nucleic acid (sequence) is translated to a significantly poorer degree than in the case where codons coding for relatively "frequent" tRNAs are present.

Especially if the modified nucleic acid (sequence) of the inventive solution for lyophilization, transfection and/or injection is in the form of a mRNA, the coding region of the modified nucleic acid is preferably modified compared to the corresponding region of the wild type mRNA such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid (sequence) of the inventive solution for lyophilization, transfection and/or injection, especially if the nucleic acid is in the form of a mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified nucleic acid (sequence) of the inventive solution for lyophilization, transfection and/or injection, especially if the nucleic acid is in the form of a mRNA, with the "frequent" codons without modifying the amino acid sequence of the protein encoded by the coding region of the nucleic acid. This preferred aspect allows provision of a particularly efficiently translated and stabilized (modified) nucleic acid (sequence) of the inventive solution for lyophilization, transfection and/or injection, especially if the nucleic acid is in the form of a mRNA.

The determination of a modified nucleic acid (sequence) of the inventive solution for lyophilization, transfection and/or injection as described above (increased G/C content; exchange of tRNAs) can be carried out using the computer program explained in WO 02/098443—the disclosure content of which is included in its full scope in the present invention. Using this computer program, the nucleotide sequence of any desired nucleic acid or mRNA can be modified with the aid of the genetic code or the degenerative nature thereof such that a maximum G/C content results, in combination with the use of codons which code for tRNAs occurring as frequently as possible in the cell, and the amino acid sequence coded by the modified nucleic acid (sequence) of the inventive solution for lyophilization, transfection and/or injection preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

In a further preferred aspect of the present invention, the A/U content in the environment of the ribosome binding site of the nucleic acid (sequence) of the inventive solution for lyophilization, transfection and/or injection, especially if the nucleic acid is in the form of a mRNA, is increased compared to the A/U content in the environment of the ribosome binding site of its particular wild type mRNA. This modification (an increased A/U content around the ribosome binding site) increases the efficiency of ribosome binding to the nucleic acid. An effective binding of the ribosomes to the ribosome binding site (Kozak sequence: GCCGCCAC-CAUGG (SEQ ID NO: 3), the AUG forms the start codon) in turn has the effect of an efficient translation of the nucleic acid.

According to a further aspect the nucleic acid (sequence) of the inventive solution for lyophilization, transfection and/or injection, especially if the nucleic acid is in the form of a mRNA, may be modified with respect to potentially destabilizing sequence elements. Particularly, the coding region and/or the 5' and/or 3' untranslated region of this nucleic acid (sequence) of the inventive solution for lyophilization, transfection and/or injection may be modified compared to the particular wild type nucleic acid such that is contains no destabilizing sequence elements, the coded amino acid sequence of the modified nucleic acid of the present invention, especially if the nucleic acid is in the form of a mRNA, preferably not being modified compared to its particular wild type nucleic acid. It is known that, for example, in sequences of eukaryotic RNAs destabilizing sequence elements (DSE) occur, to which signal proteins bind and regulate enzymatic degradation of RNA. For further stabilization of the modified nucleic acid (sequence) of the inventive solution for lyophilization, transfection and/or injection, especially if the nucleic acid is in the form of a mRNA, optionally in the region which encodes for a protein or a peptide as defined herein, one or more such modifications compared to the corresponding region of the wild type nucleic acid can therefore be carried out, so that no or substantially no destabilizing sequence elements are contained there. According to the invention, DSE present in the untranslated regions (3'- and/or 5'-UTR) can also be eliminated from the nucleic acid (sequence) of the inventive solution for lyophilization, transfection and/or injection, especially if the nucleic acid is in the form of a mRNA, by such modifications.

Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The nucleic acid (sequence) of the inventive solution for lyophilization, transfection and/or injection, especially if the nucleic acid is in the form of a mRNA, is therefore preferably modified compared to the wild type nucleic acid such that the modified nucleic acid contains no such destabilizing sequences. This also applies to those sequence motifs which are recognized by possible endonucleases, e.g. the sequence GAACAAG, which is contained in the 3'-UTR segment of the gene which codes for the transferrin receptor (Binder et al., EMBO J. 1994, 13: 1969 to 1980). These sequence motifs are also preferably removed in the nucleic acid (sequence) of the inventive solution for lyophilization, transfection and/or injection, especially if the nucleic acid is in the form of a mRNA.

Also preferably, the nucleic acid (sequence) of the inventive solution for lyophilization, transfection and/or injection as defined above, especially if the nucleic acid is in the form of a mRNA, has, in a modified form, at least one IRES as defined above and/or at least one 5' and/or 3' stabilizing sequence, in a modified form, e.g. to enhance ribosome binding or to allow expression of different encoded proteins located on an at least one (bi- or even multicistronic) RNA of the nucleic acid (sequence) of the inventive solution for lyophilization, transfection and/or injection as defined above.

According to the invention, the nucleic acid (sequence) of the inventive solution for lyophilization, transfection and/or injection as defined above, especially if the nucleic acid is in the form of a mRNA, furthermore preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-) globin gene, e.g. from *Homo sapiens* or *Xenopus laevis* may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 4), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. The nucleic acid (sequence) of the inventive solution for lyophilization, transfection and/or injection as defined above, especially if the nucleic acid is in the form of a mRNA, is therefore preferably present as (alpha-)globin UTR (untranslated regions)-stabilized RNA, in particular as (alpha-)globin UTR-stabilized RNA.

Nevertheless, substitutions, additions or eliminations of bases are preferably carried out with the nucleic acid (sequence) of the inventive solution for lyophilization, transfection and/or injection as defined above, especially if the nucleic acid is in the form of a mRNA, using a DNA matrix for preparation of the nucleic acid by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001). In such a process, for preparation of the nucleic acid (sequence) of the inventive solution for lyophilization, transfection and/or injection as defined above, especially if the nucleic acid is in the form of a mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid, e.g. mRNA, to be prepared and a termination signal for in vitro transcription. The DNA molecule, which forms the matrix of at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Nucleic acid molecules used according to the invention as defined above may be prepared using any method known in the art, including synthetic methods such as e.g. solid phase synthesis, as well as in vitro methods, such as in vitro transcription reactions.

According to another particularly preferred aspect, the nucleic acid (sequence) of the inventive solution for lyophilization, transfection and/or injection as defined above, especially if the nucleic acid is in the form of a mRNA, may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the protein or peptide as encoded by the nucleic acid (sequence) of the inventive solution for lyophilization, transfection and/or injection as defined above, especially if the nucleic acid is in the form of a mRNA, into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulines as defined herein, signal sequences of the invariant chain of immunoglobulines or antibodies as defined herein, signal sequences of Lamp1, Tapasin, Erp57, Calretikulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention.

Any of the above modifications may be applied to the nucleic acid (sequence) of the inventive solution for lyophilization, transfection and/or injection as defined above, especially if the nucleic acid is in the form of a mRNA, and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

The nucleic acid (sequence) of the inventive solution for lyophilization, transfection and/or injection as defined above as well as proteins or peptides as encoded by this nucleic acid, may comprise fragments or variants of those sequences. Such fragments or variants may typically comprise a sequence having a sequence identity with one of the above mentioned nucleic acids, or with one of the proteins or peptides or sequences, if encoded by the at least one nucleic acid (sequence) of at least 5%, 10%, 20%, 30%, 40%, 50%, 60%, preferably at least 70%, more preferably at least 80%, equally more preferably at least 85%, even more preferably at least 90% and most preferably at least 95% or even 97%, to the entire wild type sequence, either on nucleic acid level or on amino acid level.

"Fragments" of proteins or peptides in the context of the present invention (encoded by a nucleic acid as defined herein) may comprise a sequence of a protein or peptide as defined above, which is, with regard to its amino acid sequence (or its encoded nucleic acid (sequence)), N-terminally, C-terminally and/or intrasequentially truncated compared to the amino acid sequence of the original (native) protein (or its encoded nucleic acid (sequence)). Such truncation may thus occur either on the amino acid level or correspondingly on the nucleic acid level. A sequence identity with respect to such a fragment as defined above may therefore preferably refer to the entire protein or peptide as defined above or to the entire (coding) nucleic acid (sequence) of such a protein or peptide. Likewise, "fragments" of nucleic acids in the context of the present invention may comprise a sequence of a nucleic acid as defined above, which is, with regard to its nucleic acid (sequence) 5'-, 3'- and/or intrasequentially truncated compared to the nucleic acid (sequence) of the original (native) nucleic acid (sequence). A sequence identity with respect to such a fragment as defined above may therefore preferably refer to the entire nucleic acid as defined above.

Fragments of proteins or peptides in the context of the present invention (encoded by the nucleic acid (sequence) of the inventive solution for lyophilization, transfection and/or injection as defined above) may furthermore comprise a sequence of a protein or peptide as defined above, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

Fragments of proteins or peptides as defined herein (encoded by the nucleic acid (sequence) of the inventive solution for lyophilization, transfection and/or injection as defined above) may also comprise epitopes of those proteins or peptides. Epitopes (also called "antigen determinants") in the context of the present invention are typically fragments located on the outer surface of (native) proteins or peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

"Variants" of proteins or peptides as defined above may be encoded by the nucleic acid (sequence) of the inventive solution for lyophilization, transfection and/or injection as defined above, wherein nucleic acids of the nucleic acid, encoding the protein or peptide as defined above, are exchanged. Thereby, a protein or peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property.

The nucleic acid (sequence) of the inventive solution for lyophilization, transfection and/or injection as defined above may also encode a protein or peptide as defined above, wherein the encoded amino acid sequence comprises conservative amino acid substitution(s) compared to its physiological sequence. Those encoded amino acid sequences as well as their encoding nucleotide sequences in particular fall under the term variants as defined above. Substitutions in which amino acids which originate from the same class are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined above, which may be encoded by the nucleic acid (sequence) of the inventive solution for lyophilization, transfection and/or injection as defined above, may also comprise those sequences, wherein nucleic acids of the nucleic acid are exchanged according to the degeneration of the genetic code, without leading to an alteration of respective amino acid sequence of the protein or peptide, i.e. the amino acid sequence or at least part thereof may not differ from the original sequence in one or more mutation(s) within the above meaning.

In order to determine the percentage to which two sequences (nucleic acid (sequence) s, e.g. at least one nucleic acid (sequence) as defined herein, or amino acid sequences, preferably their encoded amino acid sequences, e.g. the amino acid sequences of the proteins or peptides as defined above) are identical, the sequences can be aligned in order to be subsequently compared to one another. Therefore, e.g. gaps can be inserted into the sequence of the first sequence and the component at the corresponding position of the second sequence can be compared. If a position in the first sequence is occupied by the same component as is the case at a position in the second sequence, the two sequences are identical at this position. The percentage to which two sequences are identical is a function of the number of identical positions divided by the total number of positions. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The inventive solution for lyophilization, transfection and/or injection as defined above, containing at least one nucleic acid (sequence) as defined above and mannose, may additionally contain a lactate. Such a lactate provided a surprisingly good effect on stabilization of the inventive nucleic acid (sequence) during lyophilization additional to the mannose already contained in the solution. This is particularly surprising and was not suggested by any of the prior art available. A skilled person, bearing in mind that salts typically destabilize a nucleic acid (sequence) during lyophilization, always would have expected that lactate, representing a salt, would rather destabilize than stabilize a nucleic acid (sequence) during lyophilization.

A lactate as defined herein may be any lactate available in the art. Preferably, a lactate within the context of the present invention is defined as a chemical compound, particularly a salt, derived from free lactic acid (IUPAC systematic name: 2-hydroxypropanoic acid), also known as milk acid, including its optical isomers L-(+)-lactic acid, (S)-lactic acid, D-(−)-lactic acid or (R)-lactic acid, more preferably its biologically active optical isomer L-(+)-lactic acid, wherein the salt or an anion thereof, preferably may be selected from sodium-lactate, potassium-lactate, or $Al_3^+$-lactate, $NH_4^+$-lactate, Fe-lactate, Li-lactate, Mg-lactate, Ca-lactate, Mn-lactate or Ag-lactate, or selected from Ringer's lactate (RiLa), lactated Ringer's solution (main content sodium lactate, also termed "Hartmann's Solution" in the UK), acetated Ringer's solution, or selected from lactate containing water, or ortho-lactate-containing (isotonic) solutions (e.g. for injection purposes), etc. The chemical structure of lactic acid is as follows:

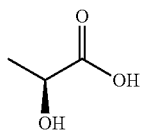

Lactic acid is a chemical compound that plays a role in several biochemical processes. It was first isolated in 1780 by a Swedish chemist, Carl Wilhelm Scheele, and is a carboxylic acid with a chemical formula of $C_3H_6O_3$. It has a hydroxyl group adjacent to the carboxyl group, making it an alpha hydroxy acid (AHA). In solution, it can lose a proton from the acidic group, producing the lactate ion $CH_3CH(OH)COO^-$. Lactic acid is chiral and has two optical isomers. One is known as L-(+)-lactic acid or (S)-lactic acid and the other, its mirror image, is D-(−)-lactic acid or (R)-lactic acid, wherein L-(+)-lactic acid is the biologically important isomer. L-lactate is constantly produced in animals from pyruvate via the enzyme lactate dehydrogenase (LDH) in a process of fermentation during normal metabolism and exercise. Industrially, lactic acid is typically produced via fermentation using among others bacteria such as *Lactobacillus* bacteria, etc.

The inventive solution for lyophilization, transfection and/or injection as defined above may typically comprise a lactate concentration in the range of about 3 mM to about 300 mM, preferably in the range of about 5 mM to about 200 mM, more preferably in the range of about 10 mM to about 150 mM, even more preferably about 15 mM to about 35 mM, and most preferably 20 mM to about 31 mM.

Alternatively, the inventive solution for lyophilization, transfection and/or injection as defined above may typically comprise a Ringer's lactate content (or a content of any of the aforementioned (undiluted) lactate containing solutions) e.g. in the range of about 10% (w/w) to about 100% (w/w), e.g. in the range of about 20% (w/w) to about 100% (w/w), in the range of about 30% (w/w) to about 100% (w/w), in the range of about 40% (w/w) to about 100% (w/w), in the range of about 50% (w/w) to about 90% (w/w), preferably in the range of about 60% (w/w) to about 90% (w/w), more preferably in the range of about 70% (w/w) to about 90% (w/w), e.g. about 80% (w/w), of Ringer's lactate (or the aforementioned (undiluted) lactate containing solution). In this context, Ringer's lactate (100% (w/w)) is typically defined as a solution comprising 131 mM $Na^+$, 5.36 mM $K^+$, 1.84 mM $Ca^{2+}$, and 28.3 mM Lactate).

The inventive solution for lyophilization, transfection and/or injection as defined above, containing at least one nucleic acid (sequence) and mannose, may additionally contain water, preferably water for injection (WFI). In this context, the term "water for injection" (WFI) is a term defined by standard USP 23. USP 23 monograph states that "Water for Injection (WFI) is water purified by distillation or reverse osmosis." WFI is typically produced by either distillation or 2-stage reverse osmosis. It is usually stored and distributed hot (at about 80° C.) in order to meet microbial quality requirements. WFI typically does not contain more than 0.25 USP endotoxin units (EU) per ml. Endotoxins are a class of pyrogens that are components of the cell wall of Gram-negative bacteria (the most common type of bacteria in water), preferably in an action limit of 10 cfu/100 ml. The microbial quality may be tested by membrane filtration of a 100 ml sample and plate count agar at an incubation temperature of 30 to 35 degrees Celsius for a 48-hour period. The chemical purity requirements of WFI are typically the same as of PW (purified water).

The inventive solution for lyophilization, transfection and/or injection as defined above, containing at least one nucleic acid (sequence) and mannose, may additionally contain further optional components or additives, e.g. a cryoprotectant, a lyoprotectant or any further suitable additive, preferably as defined in the following.

Preferably, the inventive solution for lyophilization, transfection and/or injection as defined herein may contain the herein defined contents, optional components, additives, etc. in such a concentration so as to lead to an osmolality or osmolarity comparable to that of blood plasma. In this context, the term "osmolarity" is typically to be understood as a measure of all contents, optional components, additives, etc. of the inventive solution for lyophilization, transfection and/or injection as defined herein. Osmolarity is typically the measure of solute concentration, defined as the number of osmoles (Osm) of all solubilized contents, optional components, additives, etc. per liter (l) of solution (osmol/l or osm/l). In the present context, the inventive solution for lyophilization, transfection and/or injection as defined herein may comprise an osmolarity preferably in the range of about 200 mosmol/l to about 400 mosmol/l, more preferably in the range of about 250 mosmol/l to about 350 mosmol/l, even more preferably in the range of about 270 mosmol/l to about 330 mosmol/l or in the range of about 280 mosmol/l to about 320 mosmol/l, or in the range of about e.g. about 290 mosmol/l to about 310 mosmol/l, e.g. about 295 mosmol/l, about mosmol/l, about 296 mosmol/l, about 297 mosmol/l, about 298 mosmol/l, about 299 mosmol/l, about, 300 mosmol/l, about 301 mosmol/l, about 302 mosmol/l, about 303 mosmol/l, about 304 mosmol/l, about 305 mosmol/l, about 306 mosmol/l, about 307 mosmol/l, about 308 mosmol/l.

As a particularly preferred optional component or additive, the inventive solution for lyophilization, transfection and/or injection as defined above may additionally contain at least one suspending agent, preferably mannit, preferably in a concentration of about 1 to 15% (w/w), more preferably in a concentration of about 3 to 10% (w/w), and even more preferably in a concentration of about 4 to 6% (w/w).

As a further component, the inventive solution for lyophilization, transfection and/or injection as defined above may additionally contain at least one optional component or additive selected, e.g., from mannite, proteins, peptides, amino acids, alcohols, carbohydrates, metals or metal ions, surfactants, polymers or complexing agents, buffers, etc., or a combination thereof.

In the context of the present invention, another optional component or additive of the inventive solution for lyophilization, transfection and/or injection as defined above may also be selected from the group of amino acids. Such group may comprise, without being limited thereto, any naturally occurring amino acid. Cryoprotectants and/or lyoprotectants selected from the group of amino acids may additionally comprise any modification of a naturally occurring amino acid.

Furthermore, in the context of the inventive solution for lyophilization, transfection and/or injection as defined above, a further optional component or additive may be selected from the group of alcohols. Such group may comprise, without being limited thereto, any alcohol suitable for the preparation of a pharmaceutical composition, preferably, without being limited thereto, mannitol, polyethyleneglycol, polypropyleneglycol, sorbitol, etc. However, mannitol is preferably excluded from the scope of the present invention.

Additionally, in the context of the inventive solution for lyophilization, transfection and/or injection as defined above, a further optional component or additive may be selected from the group of carbohydrates. Such group of carbohydrates may comprise, without being limited thereto, any carbohydrate, suitable for the preparation of a pharmaceutical composition, preferably, without being limited thereto, monosaccharides, such as e.g. glucose, fructose, etc., disaccharides, such as e.g. lactose, maltose, sucrose, trehalose, etc., and polysaccharides, such as e.g. dextran, HP-beta CD, etc.

Also, in the context of the inventive solution for lyophilization, transfection and/or injection as defined above, a further suitable optional component or additive may be selected from the group of proteins. Such group may comprise, without being limited thereto, proteins such as albumin, gelatine, therapeutically active proteins as defined above, antibodies as defined above, antigens as defined above, or any further protein encoded by the nucleic acid (sequence) of the inventive solution for lyophilization, transfection and/or injection as defined above.

A further optional component or additive, which may be contained in the inventive solution for lyophilization, transfection and/or injection as defined above may be selected from the group of metals or metal ions, typically comprising, without being limited thereto, metals or metal ions or salts selected from alkali metals, including members of group 1 of the periodic table: lithium (Li), sodium (Na), potassium (K), rubidium (Rb), caesium (Cs), and francium (Fr), and their (monovalent) metal alkali metal ions and salts; preferably lithium (Li), sodium (Na), potassium (K), and their (monovalent) metal alkali metal ions and salts;

alkaline earth metals, including members of group 2 of the periodic table: beryllium (Be), magnesium (Mg), calcium (Ca), strontium (Sr), barium (Ba) and radium (Ra), and their (divalent) alkaline earth metal ions and salts; preferably magnesium (Mg), calcium (Ca), strontium (Sr), barium (Ba) and their (divalent) alkaline earth metal ions and salts;

transition metals, including members of groups 3 to 13 of the periodic table and their metal ions and salts. The transition metals typically comprise the 40 chemical elements 21 to 30, 39 to 48, 71 to 80, and 103 to 112. The name transition originates from their position in the periodic table of elements. In each of the four periods in which they occur, these elements represent the successive addition of electrons to the d atomic orbitals of the atoms. In this way, the transition metals represent the transition between subgroup 2 elements and subgroup 12 (or 13) elements. Transition metals in the context of the present invention particularly comprise members of subgroup 3 of the periodic table: including Scandium (Sc), Yttrium (Y), and Lutetium (Lu), members of subgroup 4 of the periodic table: including Titan (Ti), Zirconium (Zr), and Hafnium (Hf), members of subgroup 5 of the periodic table: including Vanadium (V), Niobium (Nb), and Tantalum (Ta), members of subgroup 6 of the periodic table: including Chrome (Cr), Molybdenum (Mo), and Tungsten (W), members of subgroup 7 of the periodic table: including Manganese (Mn), Technetium (Tc), and Rhenium (Re), members of subgroup 8 of the periodic table: including Iron (Fe), Ruthenium (Ru), and Osmium (Os), members of subgroup 9 of the periodic table: including Cobalt (Co), Rhodium (Rh), and Iridium (Ir), members of subgroup 10 of the periodic table: including Nickel (Ni), Palladium (Pd), and Platin (Pt), members of subgroup 11 of the periodic table: including Copper (Cu), Silver (Ag), and Gold (Au), members of subgroup 12 of the periodic table: including Zinc (Zn), Cadmium (Cd), and Mercury (Hg); preferably members of period 4 of any of subgroups 1 to 12 of the periodic table: including Scandium (Sc), Titanium (Ti), Vanadium (V), Chromium (Cr), Manganese (Mn), Iron (Fe), Cobalt (Co), Nickel (Ni), Copper (Cu) and Zinc (Zn) and their metal ions and salts;

earth metals or members of the boron group, including members of group 3 of the periodic table: including Boron (B), Aluminium (Al), Gallium (Ga), Indium (In) and Thallium (Tl) and their metal ions and salts; preferably Boron (B) and Aluminium (Al) and their metal ions and salts;

metalloids or semi metals: including Boron (B), Silicon (Si), Germanium (Ge), Arsenic (As), Antimony (Sb), Tellurium (Te). and Polonium (Po), and their semi metal ions and salts; preferably Boron (B) and Silicon (Si) and their semi metal ions and salts;

In the context of the present invention, a further optional component or additive of the inventive solution for lyophilization, transfection and/or injection as defined above may be selected from the group of surfactants comprising, without being limited thereto, any surfactant, suitable for the preparation of a pharmaceutical composition, preferably, without being limited thereto, Tween, e.g. Tween 80 (e.g.

0.2%), Pluronics, e.g. Pluronic L121 (e.g. 1.25%), Triton-X, SDS, PEG, LTAB, Saponin, Cholate, etc.

Another optional component or additive, which may be contained in the inventive solution for lyophilization, transfection and/or injection as defined above may be selected from the group of polymers or complexing agents, preferably to complex the nucleic acid, more preferably a RNA or mRNA contained in the inventive solution for lyophilization, transfection and/or injection as defined above. Such polymers or complexing agents typically comprise, without being limited thereto, any polymer suitable for the preparation of a pharmaceutical composition, such as minor/major groove binders, nucleic acid binding proteins, lipoplexes, nanoplexes, non-cationic or non-polycationic compounds, such as PLGA, Polyacetate, Polyacrylate, PVA, Dextran, hydroxymethylcellulose, starch, MMP, PVP, heparin, pectin, hyaluronic acid, and derivatives thereof, or cationic or polycationic compounds, particularly cationic or polycationic polymers or cationic or polycationic lipids, preferably cationic or polycationic polymers. In the context of the present invention, such a cationic or polycationic compound is typically selected from any cationic or polycationic compound, suitable for complexing and thereby stabilizing a nucleic acid as defined herein, e.g. by associating the nucleic acid as defined herein with the cationic or polycationic compound. Particularly preferred, cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, protamine, spermine, spermidine, or histones. Additionally, preferred cationic or polycationic proteins or peptides may be selected from the following proteins or peptides having the total formula: $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred oligoarginines in this context are e.g. $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used for complexing the nucleic acid as defined herein may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-amino-acid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected of a cationic polymer as mentioned above) and of one or more hydrophilic- or hydrophobic blocks (e.g polyethyleneglycole); etc. Association or complexing the nucleic acid (sequence) of the inventive solution for lyophilization, transfection and/or injection as defined above with cationic or polycationic compounds preferably provides adjuvant properties to the nucleic acid, preferably if provided as an RNA, and/or confers a stabilizing effect to the nucleic acid as defined herein by complexation. The procedure for stabilizing the nucleic acid as defined herein is in general described in EP-A-1083232, the disclosure of which is incorporated by reference into the present invention in its entirety. Particularly preferred as cationic or polycationic compounds are compounds selected from the group consisting of protamine, nucleoline, spermin, spermidine, oligoarginines as defined above, such as $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc. Preferably, the nucleic acid of the inventive solution for lyophilization, transfection and/or injection as defined above, preferably an RNA or mRNA, is complexed with a cationic or polycationic compound as defined above.

As a further optional component, the inventive solution for lyophilization, transfection and/or injection as defined above may additionally contain water, water for injection (WFI), or a buffer, preferably selected from a buffer as defined above, e.g. a buffer containing 2-hydroxypropanoic acid, preferably including at least one of its optical isomers L-(+)-lactic acid, (S)-lactic acid, D-(−)-lactic acid or (R)-lactic acid, more preferably its biologically active optical isomer L-(+)-lactic acid, or a salt or an anion thereof, preferably selected from sodium-lactate, potassium-lactate, or $Al_3^+$-lactate, $NH_4^+$-lactate, Fe-lactate, Li-lactate, Mg-lactate, Ca-lactate, Mn-lactate or Ag-lactate, or a buffer selected from Ringer's lactate (RiLa), lactated Ringer's solution (main content sodium lactate, also termed "Hartmann's Solution" in the UK), acetated Ringer's solution, or ortho-lactate-containing solutions (e.g. for injection purposes), or lactate containing water. A buffer as defined herein may also be an isotonic buffer or solution, preferably selected from isotonic saline, a lactate or ortho-lactate-containing isotonic solution, a isotonic buffer or solution selected from phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), or normal saline (NaCl), hypotonic (saline) solutions with addition of glucose or dextrose, or any solution as defined herein, etc. Isotonic isotonic buffers or solutions are particularly preferred as buffers in the context of the present invention for injection and/or transfection purposes. These isotonic buffers or solutions are preferably prepared by a skilled person preferably as defined herein or according to definitions preparation protocols well known in the art for these specific isotonic buffers or solutions. More preferably, the inventive solution for lyophilization, transfection and/or injection as defined above may contain these isotonic buffers or solutions or (all) its contents in isotonic concentrations, preferably as defined herein or in the art for these specific isotonic solutions. In the above context a buffer may be used, more preferably an aqueous (isotonic solution or aqueous) buffer, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred aspect, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Typically, the salts are present in such an (isotonic solution or) buffer in a concentration of at least 50 mM sodium chloride (NaCl), at least 3 mM potassium chloride (KCl) and at least 0.01 mM calcium chloride ($CaCl_2$). Furthermore, organic anions of the aforementioned cations may be contained in the buffer. According to a more preferred aspect, the buffer may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. The buffer may be hypertonic, isotonic or hypotonic with reference to the specific reference medium, i.e. the buffer may have a higher, identical or lower salt content with reference to the specific reference medium, wherein preferably such concentrations of the aforementioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Furthermore, according to a particularly preferred aspect, the nucleic acid (sequence) of the inventive solution for lyophilization, transfection and/or injection as defined above, if lyophilized, may again be reconstituted after lyophilization in a buffer as defined herein, preferably in an isotonic buffer, preferably as defined above, e.g. as a further step of a method for lyophilization as defined herein. The nucleic acid (sequence) of the inventive solution for lyophilization, transfection and/or injection as defined above, if lyophilized, may alternatively be lyophilized in a buffer as defined above (containing mannose) and may be reconstituted after lyophilization in water or a buffer, e.g. as defined herein, to obtain the desired salt concentration or alternatively the desired buffer conditions.

As another optional component, the inventive solution for lyophilization, transfection and/or injection as defined above may additionally contain an adjuvant. Such an adjuvant is preferably an immunostimulating agent, selected from the group consisting of cationic peptides, including polypeptides including protamine, nucleoline, spermine or spermidine, cationic polysaccharides, including chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DH EA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™ ("Immunostimulating Complexes"); ISCOPREP 7.0.3.™; liposomes; LOXORIBINE™ (7-allyl-8-oxoguanosine (guanine)); LT oral adjuvant (*E. coli* labile enterotoxin-protoxin); microspheres and microparticles of any composition; MF59™; (squalane-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))ethylamide, monosodium salt); MURAMETIDE™ (Nac-Mur-L-Ala-D-Gln-OCH$_3$); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (beta-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel, etc.; emulsions, such as CFA, SAF, IFA, MF59, Provax, TiterMax, Montanide, Vaxfectin, etc.; copolymers, such as Optivax (CRL1005), L121, Poloaxmer4010), etc.; liposomes, such as Stealth, etc., cochleates, such as BIORAL, etc.; plant derived adjuvants, such as QS21, Quil A, Iscomatrix, ISCOM, etc.; preferred adjuvants suitable for costimulation may include e.g. Tomatine, biopolymers, such as PLG, PMM, Inulin, etc.; microbe derived adjuvants, such as Romurtide, DETOX, MPL, CWS, Mannose, CpG7909, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP, etc.; preferred adjuvants suitable as antagonists may e.g. include CGRP neuropeptide;

or may be selected from cationic or polycationic compounds which are suitable for depot and delivery, including protamine, nucleoline, spermin or spermidine, or other cationic peptides or proteins, including poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, protamine, spermine, spermidine, or histones. Additionally, preferred cationic or polycationic proteins or peptides may be selected from following proteins or peptides having the following total formula: $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide, cationic polysaccharides, for example chitosan, polybrene, cationic polymers, including polyethyleneimine (PEI), cationic lipids, including DOTMA: [1-(2,3-sioleyloxy)propyl]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, including modified polyaminoacids, including β-aminoacid-polymers or reversed polyamides, modified polyethylenes, including PVP (poly(N-ethyl-4-vinylpyridinium bromide)), modified acrylates, including pDMAEMA (poly(dimethylaminoethyl methylacrylate)), modified Amidoamines including pAMAM (poly(amidoamine)), modified polybetaminoester (PBAE), including diamine end modified 1,4 butanediol diacrylate-co-5-amino-1-pentanol polymers, dendrimers, including polypropylamine dendrimers or pAMAM based dendrimers, polyimine(s), including PEI: poly(ethyleneimine), poly(propyleneimine), polyallylamine, sugar backbone based polymers, including cyclodextrin based polymers, dextran based polymers, Chitosan, silan backbone based polymers, including PMOXA-PDMS copolymers, blockpolymers consisting of a combination of one or more cationic blocks (including selected og a cationic polymer as mentioned above) and of one or more hydrophilic- or hydrophobic blocks (e.g polyethyleneglycole);

or may be selected from nucleic acids of formula (I) above: $G_lX_mG_n$;

or may be selected from nucleic acids of formula (II) above: $C_lX_mC_n$.

As another optional component, the inventive solution for lyophilization, transfection and/or injection as defined above may additionally contain a protein or a peptide, which may be selected, without being restricted thereto, e.g. from therapeutically active proteins or peptides, from antigens, e.g. tumor antigens, pathogenic antigens (e.g. selected from pathogenic proteins as defined above or from animal antigens, viral antigens, protozoal antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application.

As another optional component, the inventive solution for lyophilization, transfection and/or injection as defined above may additionally contain one or more compatible solid or liquid fillers or diluents or encapsulating compounds, which are suitable for administration to a patient to be treated. The term "compatible" as used here means that these constituents are capable of being mixed with the nucleic acid (sequence) of the inventive solution for lyophilization, transfection and/or injection as defined above in such a manner that no interaction occurs which would substantially reduce the pharmaceutical effectiveness of the nucleic acid under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theo-*

*broma*; polyols, such as, for example, polypropylene glycol, glycerol, sorbitol, mannitol and polyethylene glycol; alginic acid.

The inventive solution for lyophilization, transfection and/or injection as defined above may occur as a liquid, a semi-liquid or even a semi-solid or a solid sample or composition, preferably as a liquid, a semi-liquid or a semi-solid sample or composition, more preferably as a liquid or a semi-liquid sample or composition.

The pH of the inventive solution for lyophilization, transfection and/or injection as defined above may be in the range of about 4 to 8, preferably in the range of about 6 to about 8, more preferably from about 7 to about 8.

Particularly preferred, the inventive solution for lyophilization, transfection and/or injection as defined above may be a transfection and/or injection solution. In this context, the inventive solution can be used for injection and surprisingly allows to significantly enhance the rate of (transfection and thus) expression of a protein as defined above, preferably of a protein, which is encoded by a nucleic acid as defined above and forming part of the inventive solution for lyophilization, transfection and/or injection. Such an injection solution may contain any components as defined above for the inventive solution for lyophilization, transfection and/or injection. Alternatively or additionally, the inventive injection solution may be formed as a pharmaceutical composition or vaccine as defined in the following or may contain components thereof. Most preferably, the inventive injection solution can comprise or even consist of an isotonic solution as defined above and e.g. can (additionally) contain different salts (e.g. 0.5 mM to 50 mM potassium, 13 mM to 250 mM sodium, 0.2 mM to 10 mM calcium, and 0.2 mM to 10 mM magnesium). Different injection solutions can be utilized, e.g. PBS, HBSS, Ringer-Lactat. The inventive injection solution may be administered as described in the following for a pharmaceutical composition or vaccine.

According to another particularly preferred aspect, the inventive solution for lyophilization, transfection and/or injection as defined above may be a solution for lyophilization of a nucleic acid as described herein. In this context, the solution for lyophilization of a nucleic acid as described herein surprisingly and significantly enhances storage stability of RNA, particularly in lyophilized form.

According to a second embodiment, the present invention provides a lyophilized nucleic acid (sequence), which has been lyophilized in an inventive solution for lyophilization, transfection and/or injection as defined above. In other words, lyophilization may be carried out starting from an inventive solution for lyophilization, transfection and/or injection as defined above, containing at least a nucleic acid (sequence) and mannose as defined above. Furthermore, the solution may contain any further optional components as defined above, preferably lactate or a lactate derived salt as defined above.

Upon lyophilization starting from an inventive solution for lyophilization, transfection and/or injection as defined above, the (residual) water content of the lyophilized nucleic sequence acid as defined herein is typically reduced to a content of about 0.5% (w/w) to about 10% (w/w), more preferably to a content of about 1% (w/w) to about 5% (w/w), even more preferably to a content of about 2% (w/w) to about 4% (w/w), most preferably to a content of about 3% (w/w), e.g. 3% (w/w)±2% (w/w), or 3% (w/w)γ1% (w/w).

The lyophilized nucleic acid (sequence) as defined herein typically comprises an excellent enhanced storage-stability, when compared to a lyophilized nucleic acid (sequence) of the art, which has been lyophilized without the presence of mannose, e.g. in the presence of water for injection (WFI) as described herein. The lyophilized nucleic acid (sequence) as defined and as prepared herein advantageously can be stored in a temperature range of about −80° C. to +60° C. significantly longer, when compared to a lyophilized nucleic acid (sequence) of the art. According to the present invention, the storage-stability of the lyophilized nucleic acid (sequence) is calculated on the basis of the relative integrity of the nucleic acid (sequence). The relative integrity of the lyophilized nucleic acid (sequence) is typically defined as the relative content of the nucleic acid (sequence) exhibiting a correct length when compared to the total content of the at least one nucleic acid (sequence) in the sample. In the context of an mRNA, the relative integrity of the mRNA in the lyophilized mRNA is typically defined as the relative content of the mRNA exhibiting a correct length when compared to the total content of mRNA in the sample. The storage-stability of a nucleic acid (sequence) is typically determined on the basis of the relative integrity (over a defined or not defined period of time), wherein the nucleic acid (sequence) typically exhibits an unchangend biological activity. In the context of the present invention the storage stability is preferably regarded as complied with, if the relative integrity of the (lyophilized) nucleic acid (sequence) (s) is at least about 70%. A relative integrity of more than 70% meets the quality criteria of CureVac GmbH for mRNA, e.g. for mRNA exhibiting a GC-content of more than 60% and a base length of <2000 nt in RNA containing formulations. This criterium may be applied to the above definition.

The lyophilized nucleic acid (sequence) as defined herein, which may be lyophilized from an inventive solution for lyophilization, transfection and/or injection as defined above, may be prepared using a method as defined herein in the following.

Therefore, according to a further aspect, the present invention also provides a method of lyophilization of a nucleic acid (sequence), preferably for preparation of a lyophilized nucleic acid (sequence) as defined herein, particularly for preparation of a lyophilized nucleic acid (sequence) which may be lyophilized from an inventive solution for lyophilization, transfection and/or injection as defined above.

In the context of the present invention lyophilization (also termed cryodesiccation) is typically understood as a freeze-drying process, which allows removing water from a frozen sample, e.g. from an inventive solution for lyophilization, transfection and/or injection as defined above containing a nucleic acid (sequence) and mannose as defined above, via sublimation as described below in further detail. The inventive method of lyophilization of a nucleic acid as defined herein from an inventive solution for lyophilization, transfection and/or injection as defined above preferably leads to an enhanced storage stability of the nucleic acid. The method typically comprises the following steps:

a) optionally providing as a nucleic acid containing sample an inventive solution for lyophilization, transfection and/or injection as defined above containing a nucleic acid (sequence) and mannose as defined above, and optionally supplemented with further components as defined above;

b) freezing the nucleic acid containing sample, obtained according to step a);

c) drying the frozen nucleic acid containing sample, obtained according to step b), via sublimation;

d) optionally floating the lyophilized nucleic acid obtained according to step c) with an inert gas, such as nitrogen, etc., or a noble gas, such as helium, neon, argon, xenon, krypton;

e) optionally sealing the lyophilized nucleic acid obtained according to step c) or d).

The inventive method is directed to a method of lyophilization of a nucleic acid (sequence) as defined herein, preferably a nucleic acid (sequence) forming part of the inventive solution for lyophilization, transfection and/or injection as defined above. Lyophilization (also termed cryodesiccation) is typically understood as a process, which allows removing water from a frozen sample (preferably the above defined inventive solution containing at least one nucleic acid (sequence) and mannose as defined above) in one or more steps via sublimation. In the context of the present invention, lyophilization is typically carried out by freeze-drying a sample first freezing a nucleic acid containing sample, which has been supplemented with mannose as defined herein, and then drying the nucleic acid containing sample via sublimation, optionally by reducing the surrounding pressure and/or adding enough heat to allow the frozen water in the sample to sublime directly from the solid phase to gas.

According to an optional first step a) of the inventive method of lyophilization an inventive solution for lyophilization, transfection and/or injection as defined above, containing at least one nucleic acid (sequence) and mannose as defined above, and optionally supplemented with further components as defined above, is provided. The inventive solution, particularly the at least one nucleic acid (sequence), the mannose and the optional components, is preferably as defined above. The inventive solution may be prepared e.g. by adding mannose as defined above, preferably in the above defined concentrations, to a sample containing a nucleic acid (sequence) as defined above, or by adding a nucleic acid (sequence) as defined above to a mannose containing sample, preferably in the above defined concentrations. Such an inventive solution for lyophilization, transfection and/or injection as defined above has optionally been supplemented with further components, preferably as defined above.

According to the second step b) the nucleic acid containing sample, particularly the inventive solution for lyophilization, transfection and/or injection as defined above containing at least one nucleic acid and mannose as defined herein, is frozen. The freezing process may be carried out by any method, which allows to (entirely) freeze the sample. In a lab, this may be done by placing the material in a freeze-drying flask and rotating the flask in a bath, called a shell freezer, which is cooled by mechanical refrigeration, dry ice and methanol, or liquid nitrogen. On a larger-scale, freezing is usually carried out using a freeze-drying machine. In this step, it is important to cool the material below its triple point, the lowest temperature at which the solid and liquid phases of the material can coexist. This ensures that sublimation rather than melting will occur in the following steps. Larger crystals are easier to freeze-dry. Usually, the freezing temperatures are in the range between −20° C. and −80° C., preferably in the between −30° C. and −60° C., even more preferably in the range between −40° C. and −50° C., most preferably about −47° C.

According to a third step c), the frozen sample is dried, typically using two drying steps, primary drying step c1) and secondary drying step c2). During the primary drying step c1), free, i.e. unbound, water surrounding the nucleic acid (sequence) and optionally further components, escapes from the solution. Subsequent thereto water being bound on a molecular basis by the at least one nucleic acid (sequence) may be removed in a secondary drying step c2) by adding thermal energy. In both cases the hydration sphere around the nucleic acid (sequence) is lost.

The primary drying step c1) may be carried out at normal pressure, e.g. in the range of about 980 to about 1045 millibar (mbar), e.g. about 1013 mbar, but also may be carried out by lowering the pressure, usually to the range of a few millibar, e.g. in the range of about 0.001 mbar to about 0.2 mbar, preferably in the range of about 0.01 mbar to about 0.1 mbar, even more preferably in the range of about 0.025 mbar to about 0.075 mbar, e.g. about 0.05 mbar. In this primary drying step, pressure is typically controlled through the application of partial vacuum. The vacuum allows speeding up sublimation, making it useful as a deliberate drying process. Furthermore, a cold condenser chamber and/or condenser plates may be used to provide (a) surface(s) for the water vapor to re-solidify on. Condenser temperatures are typically below −50° C. (−60° F.). Alternatively, instead of lowering the pressure, heat may be supplied to the sample to allow for the water to sublimate. The amount of heat necessary can be calculated using the sublimating molecules' latent heat of sublimation. In this initial drying phase, about 95% (w/w) of the water in the material is sublimated. This phase may be carried out slow to avoid applying too much heat and possible alteration or damage of the structure of the nucleic acid to be lyophilized. The heat, if applied, may be in the range of about −40° C. to about +20° C., e.g. in the range of about −30° C. to about +20° C., in the range of about −20° C. to about +20° C., in the range of about −10° C. to about +10° C., in the range of about −40° C. to about +10° C., in the range of about −30° C. to about +10° C., in the range of about −20° C. to about +10° C., in the range of about −20° C. to about +/−0° C., or in the range of about −10° C. to about +/−0° C. As a further alternative, heat and low pressure may be applied, preferably heat in the range as defined above and a low pressure in the range as defined above.

The secondary drying step c2) typically aims to remove unfrozen water molecules bound in the structure of the nucleic acid (sequence), since the ice (frozen water molecules) is usually removed in the primary drying step c1) above. In this secondary drying step c2), the temperature is typically raised higher than in the primary drying step, and can even be above 0° C., to break any physico-chemical interactions that have formed between the water molecules and the frozen material. Alternatively, the pressure may be lowered in this stage to encourage desorption. According to a further alternative, heat can be applied and pressure can be lowered, preferably in the above ranges. More preferably, the heat, if applied, may be in the range of about +10° C. to about +40° C., preferably in the range of about +25° C. to about +35° C., e.g. about 30° C. The pressure, if lowered, is usually lowered to the range of a few millibars, e.g. as defined above, more preferably in the range of about 0.001 mbar to about 0.05 mbar, preferably in the range of about 0.001 mbar to about 0.025 mbar, even more preferably in the range of about 0.005 mbar to about 0.015 mbar, e.g. about 0.01 mbar. As a further alternative, heat and low pressure may be applied, preferably in the ranges as defined above.

After the freeze-drying process is complete, i.e. steps b) and c), particularly c1) and c2), are finished, the lyophilized nucleic acid (sequence) obtained according to steps b) and c), particularly c1) and c2), is typically floated in an optional step d) with an inert gas, such as nitrogen, etc., or a noble gas, such as helium, neon, argon, xenon, krypton, and/or the lyophilized nucleic acid is typically sealed. For this purpose, the vacuum is usually broken, e.g. to atmospheric pressure (preferably about 1013 mbar), if low pressure was applied, and the temperature is typically adjusted to room temperature, if heat was used.

Subsequently or alternatively to step d) of the inventive method of lyophilization, the lyophilized nucleic acid (sequence) is optionally sealed in step e) of the inventive method of lyophilization with or without an inert gas. For this purpose, the lyophilized nucleic acid (sequence) is advantageously contained in any of the above mentioned steps a), b), c), and d) (and more preferably already lyophilized) in a sealable container.

At the end of the lyophilization method as defined above, typically comprising optionally step a), step b) step c), particularly steps c1) and c2), and optionally step d) and/or step e), a lyophilized nucleic acid is preferably obtained, wherein the final (residual) water content in the inventive lyophilized nucleic acid is preferably in the range of about 0.5% (w/w) to about 10% (w/w), more preferably in the range of about 1% (w/w) to about 5% (w/w), even more preferably in the range of about 2% (w/w) to about 4% (w/w), most preferably in the range of about 3% (w/w), e.g. 3% (w/w)±2% (w/w), or 3% (w/w)γ1% (w/w).

After carrying out any of steps b) and c) a lyophilized nucleic acid (sequence) may be obtained, which may be used for the inventive purposes. Additionally, steps d) and/or e) may be carried out. However, the lyophilized nucleic acid (sequence) may alternatively or additionally to steps d) and/or e) be reconstituted in a solution to obtain a product which is ready to be used in any of the herein mentioned applications. Therefore, according to a particularly preferred aspect, the lyophilized nucleic acid (sequence) may again be reconstituted in a buffer as defined above or a solution for reconstitution. Preferably, such a solution for reconstitution is a solution as defined above for the inventive solution for lyophilization, transfection and/or injection, wherein the solution for reconstitution may contain at least one of the components as defined above for the inventive solution for lyophilization, transfection and/or injection except of the nucleic acid. Most preferred is an isotonic solution for reconstitution. The reconstitution may occur, e.g., after lyophilization, e.g. as a further step f) of the abovementioned method for lyophilization.

According to a third embodiment, the present invention furthermore provides a pharmaceutical composition, comprising the inventive solution for lyophilization, transfection and/or injection as defined above containing at least a nucleic acid (sequence) and mannose and eventually further components as defined above, or the lyophilized nucleic acid (sequence) or the lyophilized inventive solution as defined above and optionally a pharmaceutically acceptable carrier and/or vehicle. The inventive pharmaceutical composition may optionally be supplemented with further components as defined above for the inventive solution for lyophilization, transfection and/or injection.

As a first ingredient, the inventive pharmaceutical composition comprises the inventive solution for lyophilization, transfection and/or injection as defined above containing a nucleic acid (sequence) and mannose as defined above, or the lyophilized nucleic acid (sequence) as defined above.

As a second ingredient the inventive pharmaceutical composition may comprise another class of compounds, which may be added to the inventive pharmaceutical composition in this context, may be selected from at least one pharmaceutically active component. A pharmaceutically active component in this context is a compound that has a therapeutic effect against a particular indication, preferably cancer diseases, autoimmune disease, allergies, infectious diseases or a further disease as defined herein. Such compounds include, without implying any limitation, preferably compounds including, without implying any limitation, peptides or proteins (e.g. as defined herein), nucleic acids, (therapeutically active) low molecular weight organic or inorganic compounds (molecular weight less than 5000, preferably less than 1000), sugars, antigens or antibodies (e.g. as defined herein), therapeutic agents already known in the prior art, antigenic cells, antigenic cellular fragments, cellular fractions; modified, attenuated or de-activated (e.g. chemically or by irridation) pathogens (virus, bacteria etc.), etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred aspect, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred aspect, the buffer suitable for injection purposes as defined above is an isotonic injection solution as defined herein and therefore may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person and may be as defined above. Most preferred are isotonic solutions as defined above in general may be present in an osmolality or osmolarity comparable to that of blood plasma, preferably in the range as defined above.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the nucleic acid (sequence) as defined herein in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. Most preferred is intradermal and transdermal administration.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the at least one nucleic acid as defined above of the inventive solution for lyophilization, transfection and/or injection as defined above containing a nucleic acid (sequence) and mannose as defined above, or of the lyophilized nucleic acid (sequence) as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the components as defined above suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition typically comprises a "safe and effective amount" of the components of the inventive pharmaceutical composition as defined above, particularly of the at least one nucleic acid (sequence). As used herein, a "safe and effective amount" means an amount of the at least one nucleic acid (sequence) that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the at least one nucleic acid (sequence) will furthermore vary in connection with the particular condition to be treated and also with the age and physical condition of the patient to be treated, the body weight, general health, sex, diet, time of administration, rate of excretion, drug combination, the activity of the specific nucleic acid (sequence) employed, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

According to a specific aspect, the inventive pharmaceutical composition may be provided as a vaccine. Such an inventive vaccine is typically composed like the inventive pharmaceutical composition, i.e. it contains at least comprising the inventive solution for lyophilization, transfection and/or injection as defined above containing a nucleic acid (sequence) and mannose as defined above, or the lyophilized nucleic acid (sequence) as defined above and optionally a pharmaceutically acceptable carrier and/or vehicle. Further components may be as defined above for the inventive pharmaceutical composition. The inventive vaccine preferably supports at least an innate immune response of the immune system of a patient to be treated. Additionally, the inventive vaccine furthermore may also elicit an adaptive immune response, preferably, if the at least one nucleic acid (sequence) of the inventive vaccine encodes any of the above mentioned antigens (or antibodies), which elicit an adaptive immune response.

The inventive vaccine may also comprise a pharmaceutically acceptable carrier, adjuvant, and/or vehicle as defined above for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines herein may be administered by an intradermal, subcutaneous, or intramuscular route. Inventive vaccines are therefore preferably formulated in liquid (or sometimes in solid) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine can additionally contain one or more auxiliary substances in order to further increase its immunogenicity. A synergistic action of the at least one nucleic acid sequence of the inventive vaccine and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner or adjuvants as defined above. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form. The CpG nucleic acids may be provided either in solubilized or in lyophilized form e.g. lyophilized using a method likewise as described herein for the inventive nucleic acid (sequence).

Finally, another class of compounds, which may be added to an inventive vaccine in this context, may be selected from at least one pharmaceutically active component as defined above for the inventive pharmaceutical composition.

According to a further embodiment, the present invention provides several applications and uses of the inventive solution for lyophilization, transfection and/or injection containing a nucleic acid (sequence) and mannose, or of the inventive lyophilized nucleic acid (sequence), of the inventive pharmaceutical composition or of the inventive vaccine all preferably as defined above.

According to one specific aspect, the present invention is directed to the use of the inventive solution for lyophilization, transfection and/or injection containing a nucleic acid (sequence) and mannose, or the use of the inventive lyophilized nucleic acid (sequence) for lyophilization, transfection and/or injection.

According to one other specific aspect, the present invention is directed to the use of the inventive solution for lyophilization, transfection and/or injection containing a nucleic acid (sequence) and mannose, or the use of the inventive lyophilized nucleic acid (sequence) for the preparation of an injection solution as defined herein. More preferably, such an injection solution may be used to (significantly) enhance the transfection efficiency of the nucleic acid and or the expression of a protein encoded by the nucleic acid sequence, whereby the encoded protein is preferably a protein as defined herein. Accordingly, the present invention may also be directed to the use of the inventive solution for lyophilization, transfection and/or injection containing a nucleic acid (sequence) and mannose, or the use of the inventive lyophilized nucleic acid (sequence) (for the preparation of an injection solution as defined herein, e.g. as a pharmaceutical composition) to (significantly) enhance the transfection efficiency of the nucleic acid and or the expression of a protein encoded by the nucleic acid sequence, whereby the encoded protein is preferably a protein as defined above. Such an injection solution may contain any components as defined above for the inventive solution for lyophilization, transfection and/or injection. Alternatively or additionally, the inventive injection solution may be formed as a pharmaceutical composition or vaccine as defined in the following or may contain components thereof. Preferably, the inventive injection solution may be formulated and/or administered as described in the following for a pharmaceutical composition or vaccine.

According to one other specific aspect, the present invention is directed to the first medical use of the inventive solution for lyophilization, transfection and/or injection containing a nucleic acid (sequence) and mannose, or the first medical use of the inventive lyophilized nucleic acid (sequence), i.e. the use of the inventive solution for lyophilization, transfection and/or injection containing a nucleic acid (sequence) and mannose, or the inventive lyophilized nucleic acid (sequence) as a medicament. The medicament may be in the form of a pharmaceutical composition or in the form of a vaccine as a specific form of pharmaceutical compositions, both preferably as defined herein.

According to one further aspect, the present invention is directed to the use of the inventive solution for lyophilization, transfection and/or injection containing a nucleic acid (sequence) and mannose, or more preferably the use of the inventive lyophilized nucleic acid (sequence), or the inventive pharmaceutical composition or the inventive vaccine for the prophylaxis, treatment and/or amelioration of diseases as defined herein, preferably selected from cancer or tumor diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases, or any further disease mentioned herein.

According to another aspect, the present invention is directed to the (second medical) use of the inventive solution for lyophilization, transfection and/or injection containing a nucleic acid (sequence) and mannose, or more preferably the use of the inventive lyophilized nucleic acid (sequence), or the inventive pharmaceutical composition or the inventive vaccine for the treatment of diseases as defined herein, preferably to the use of the inventive solution for lyophilization, transfection and/or injection containing a nucleic acid (sequence) and mannose, or more preferably the use of the inventive lyophilized nucleic acid (sequence), or the inventive pharmaceutical composition or the inventive vaccine for the preparation of a medicament for the prophylaxis, treatment and/or amelioration of various diseases as defined herein, preferably selected from cancer or tumor diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases, or any further disease mentioned herein.

According to one specific aspect, diseases as defined herein comprise cancer or tumor diseases, preferably selected from melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma), hepatitis B-induced tumors (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma (=Oesophageal cancer), wart involvement, tumors of the small intestine, craniopharyngeomas, ovarian carcinoma, genital tumors, ovarian cancer (=Ovarian carcinoma), pancreatic carcinoma (=pancreatic cancer), endometrial carcinoma, liver metastases, penile cancer, tongue cancer, gall bladder cancer, leukaemia, plasmocytoma, lid tumor, prostate cancer (=prostate tumors), etc.

According to one further specific aspect, diseases as defined herein comprise infectious diseases, preferably (viral, bacterial or protozoological) infectious diseases. Such infectious diseases, preferably to (viral, bacterial or protozoological) infectious diseases, are typically selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), bacterial infectious diseases such as miscarriage (prostate inflammation), anthrax, appendicitis, borreliosis, botulism, *Camphylobacter*, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific aspect, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjogren's syndrome, Scleroderma, Rheumatoid Arthritis and polymyositis or local syndromes which may be endocrinologic (type I diabetes (Diabetes mellitus Type I), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type I), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T-Cell bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the β-subunit of T-cell receptors in a non-specific fashion. Another explanation deduces autoimmune diseases from a Molecular Mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever.

Additionally, according to one further specific aspect, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined above. Such allergy antigens or allergens may be selected from allergy antigens as defined above antigens derived from different sources, e.g. from animals, plants, fungi, bacteria, etc. Allergens in this context include e.g. grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterized by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. Treatment of such allergic disorders or diseases may occur preferably by desensitizing the immune reaction which triggers a specific immune response. Such a desensitizing may be carried out by administering an effective amount of the allergen or allergic antigen encoded by the lyophilized nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Additionally, diseases to be treated in the context of the present invention likewise include (hereditary) diseases, or genetic diseases in general monogenetic diseases, i.e. (hereditary) diseases, or genetic diseases in general. Such (mono-)genetic diseases, (hereditary) diseases, or genetic diseases in general are typically caused by genetic defects, e.g. due to gene mutations resulting in loss of protein activity or regulatory mutations which do not allow transcription or translation of the protein. Frequently, these diseases lead to metabolic disorders or other symptoms, e.g. muscle dystrophy. The present invention allows treating the following (hereditary) diseases or genetic diseases: 3-beta-hydroxysteroid dehydrogenase deficiency (type II); 3-ketothiolase deficiency; 6-mercaptopurine sensitivity; Aarskog-Scott syndrome; Abetal ipoproteinemia; Acatalasemia; Achondrogenesis; Achondrogenesis-hypochondrogenesis; Achondroplasia; Achromatopsia; Acromesomelic dysplasia (Hunter-Thompson type); ACTH deficiency; Acyl-CoA dehydrogenase deficiency (short-chain, medium chain, long chain); Adenomatous polyposis coli; Adenosin-deaminase deficiency; Adenylosuccinase deficiency; Adhalinopathy; Adrenal hyperplasia, congenital (due to 11-beta-hydroxylase deficiency; due to 17-alpha-hydroxylase deficiency; due to 21-hydroxylase deficiency); Adrenal hypoplasia, congenital, with hypogonadotropic hypogonadism; Adrenogenital syndrom; Adrenoleukodystrophy; Adrenomyeloneuropathy; Afibrinogenemia; Agammaglobulinemia; Alagille syndrome; Albinism (brown, ocular, oculocutaneous, rufous); Alcohol intolerance, acute; Aldolase A deficiency; Aldosteronism, glucocorticoid-remediable; Alexander disease; Alkaptonuria; Alopecia universalis; Alpha-1-antichymotrypsin deficiency; Alpha-methylacyl-CoA racemase deficiency; Alpha-thalassemia/mental retardation syndrome; Alport syndrome; Alzheimer disease-1 (APP-related); Alzheimer disease-3; Alzheimer disease-4; Amelogenesis imperfecta; Amyloid neuropathy (familial, several allelic types); Amyloidosis (Dutch type; Finnish type; hereditary renal; renal; senile systemic); Amytrophic lateral sclerosis; Analbuminemia; Androgen insensitivity; Anemia (Diamond-Blackfan); Anemia (hemolytic, due to PK deficiency); Anemia (hemolytic, Rh-null, suppressor type); Anemia (neonatal hemolytic, fatal and nearfatal); Anemia (sideroblastic, with ataxia); Anemia (sideroblastic/hypochromic); Anemia due to G6PD deficiency; Aneurysm (familial arterial); Angelman syndrome; Angioedema; Aniridia; Anterior segment anomalies and cataract; Anterior segment mesenchymal dysgenesis; Anterior segment mesenchymal dysgenesis and cataract; Antithrombin III deficiency; Anxiety-related personality traits; Apert syndrome; Apnea (postanesthetic); ApoA-I and apoC-III deficiency (combined); Apolipoprotein A-II deficiency; Apolipoprotein B-100 (ligand-defective); Apparent mineralocorticoid excess (hypertension due to); Argininemia; Argininosuccinicaciduria; Arthropathy (progressive pseudorheumatoid, of childhood); Aspartylglucosaminuria; Ataxia (episodic); Ataxia with isolated vitamin E deficiency; Ataxia-telangiectasia; Atelosteogenesis II; ATP-dependent DNA ligase deficiency; Atrial septal defect with atrioventricular conduction defects; Atrichia with papular lesions; Autism (succinylpurinemic); Autoimmune polyglandular disease, type I; Autonomic nervous system dysfunction; Axenfeld anomaly; Azoospermia; Bamforth-Lazarus syndrome; Bannayan-Zonana syndrome; Barthsyndrome; Bartter syndrome (type 2 or type 3); Basal cell carcinoma; Basal cell nevus syndrome; BCG infection; Beare-Stevenson cutis gyrata syndrome; Becker muscular dystrophy; Beckwith-Wiedemann syndrome; Bernard-Soulier syndrome (type B; type C); Bethlem myopathy; Bile acid malabsorption, primary; Biotimidase deficiency; Bladder cancer; Bleeding disorder due to defective thromboxane A2 receptor; Bloom syndrome; Brachydactyly (type B1 or type C); Branchiootic syndrome; Branchiootorenal syndrome; Breast cancer (invasive intraductal; lobular; male, with Reifenstein syndrome; sporadic); Breast cancer-1 (early onset); Breast cancer-2 (early onset); Brody myopathy; Brugada syndrome; Brunner syndrome; Burkitt lymphoma; Butterfly dystrophy (retinal); C1q deficiency (type A; type B; type C); C1r/C1s deficiency; C1s deficiency, isolated; C2 deficiency; C3 deficiency; C3b inactivator deficiency; C4 deficiency; C8 deficiency, type II; C9 deficiency; Campomelic dysplasia with autosomal sex reversal; Camptodactyly-arthropathy-coxa varapericarditis syndrome; Canavan disease; Carbamoylphosphate synthetase I deficiency; Carbohydrate-deficient glycoprotein syndrome (type I; type Ib; type II); Carcinoid tumor of lung; Cardioencephalomyopathy (fatal infantile, due to cytochrome c oxidase deficiency); Cardiomyopathy (dilated; X-linked dilated; familial hypertrophic; hypertrophic); Carnitine deficiency (systemic primary); Carnitine-acylcarnitine translocase deficiency; Carpal tunnel syndrome (familial); Cataract (cerulean; congenital; crystalline aculeiform; juvenile-onset; polymorphic and lamellar; punctate; zonular pulverulent); Cataract, Coppock-like; CD59 deficiency; Central core disease; Cerebellar ataxia; Cerebral amyloid angiopathy; Cerebral arteriopathy with subcortical infarcts and leukoencephalopathy; Cerebral cavernous malformations-1; Cerebrooculofacioskeletal syndrome; Cerebrotendinous xanthomatosis; Cerebrovascular disease; Ceroid lipofuscinosis (neuronal, variant juvenile type, with granular osmiophilic deposits); Ceroid lipofuscinosis (neuronal-1, infantile); Ceroid-lipofuscinosis (neuronal-3, juvenile); Char syndrome; Charcot-Marie-Tooth disease; Charcot-Marie-Tooth neuropathy; Charlevoix-Saguenay type; Chediak-Higashi syndrome; Chloride diarrhea (Finnish type); Cholestasis (benign recurrent intrahepatic); Cholestasis (familial intrahepatic); Cholestasis (progressive familial intrahepatic); Cholesteryl ester storage disease; Chondrodysplasia punctata (brachytelephalangic; rhizomelic; X-linked dominant; X-linked recessive; Grebe type); Chondrosarcoma; Choroideremia; Chronic granulomatous disease (autosomal, due to deficiency of CYBA); Chronic granulomatous disease (X-linked); Chronic granulomatous disease due to deficiency of NCF-1; Chronic granulomatous disease due to deficiency of NCF-2; Chylomicronemia syndrome, familial; Citrullinemia; classical Cockayne syndrome-1; Cleft lip, cleft jaw, cleft palate; Cleft lip/palate ectodermal dysplasia syndrome; Cleidocranial dysplasia; CMO II deficiency; Coats disease; Cockayne syndrome-2, type B; Coffin-Lowry syndrome; Colchicine resistance; Colon adenocarcinoma; Colon cancer; Colorblindness (deutan; protan; tritan); Colorectal cancer; Combined factor V and VIII deficiency; Combined hyperlipemia (familial); Combined immunodeficiency (X-linked, moderate); Complex 1 deficiency; Complex neurologic disorder; Cone dystrophy-3; Cone-rod dystrophy 3; Cone-rod dystrophy 6; Cone-rod retinal dystrophy-2; Congenital bilateral absence of vas deferens; Conjunctivitis, ligneous; Contractural arachnodactyly; Coproporphyria; Cornea plana congenita; Corneal clouding; Corneal dystrophy (Avellino type; gelatinous drop-like; Groenouw type I; lattice type I; Reis-Bucklers type); Cortisol resistance; Coumarin resistance; Cowden disease; CPT deficiency, hepatic (type I; type II); Cramps (familial, potassium-aggravated); Craniofacial-deafness-hand syndrome; Craniosynostosis (type 2); Cretinism; Creutzfeldt-Jakob disease; Crigler-Najjar syndrome; Crouzon syndrome; Currarino syndrome; Cutis laxa; Cyclic hematopoiesis; Cyclic ichthyosis; Cylindromatosis; Cystic fibrosis; Cystinosis (nephropathic); Cystinuria (type II; type III); Daltonism; Darier disease; D-bifunctional protein deficiency; Deafness, autosomal dominant 1; Deafness, autosomal dominant 11; Deafness, autosomal dominant 12; Deafness, autosomal dominant 15; Deafness, autosomal dominant 2; Deafness, autosomal dominant 3; Deafness, autosomal dominant 5; Deafness, autosomal dominant 8; Deafness, autosomal dominant 9; Deafness, autosomal recessive 1; Deafness, autosomal recessive 2; Deafness, autosomal recessive 21; Deafness, autosomal recessive 3; Deafness, autosomal recessive 4; Deafness, autosomal recessive 9; Deafness, nonsyndromic sensorineural 13; Deafness, X-linked 1; Deafness, X-linked 3; Debrisoquine sensitivity; Dejerine-Sottas disease; Dementia (familial Danish); Dementia (frontotemporal, with parkinsonism); Dent disease; Dental anomalies; Dentatorubro-pallidoluysian atrophy; Denys-Drash syndrome; Dermatofibrosarcoma protuberans; Desmoid disease; Diabetes insipidus (nephrogenic); Diabetes insipidus (neurohypophyseal); Diabetes mellitus (insulin-resistant); Diabetes mellitus (rare form); Diabetes mellitus (type II); Diastrophic dysplasia; Dihydropyrimidinuria; Dosage-sensitive sex reversal; Doyne honeycomb degeneration of retina; Dubin-Johnson syndrome; Duchenne muscular dystrophy; Dyserythropoietic anemia with thrombocytopenia; Dysfibrinogenemia (alpha type; beta type; gamma type); Dyskeratosis congenita-1; Dysprothrombinemia; Dystonia (DOPAresponsive); Dystonia (myoclonic); Dystonia-1 (torsion); Ectodermal dysplasia; Ectopia lentis; Ectopia pupillae; Ectrodactyly ectodermal dysplasia, and cleft lip/palate syndrome 3); Ehlers-Danlos syndrome (progeroid form); Ehlers-Danlos syndrome (type I; type II; type III; type IV; type VI; type VII); Elastin Supravalvar aortic stenosis; Elliptocytosis-1; Elliptocytosis-2; Elliptocytosis-3; Ellis-van Creveld syndrome; Emery-Dreifuss muscular dystrophy; Emphysema; Encephalopathy; Endocardial fibroelastosis-2; Endometrial carcinoma; Endplate acetylcholinekerase deficiency; Enhanced S-cone syndrome; Enlarged vestibular aqueduct; Epidermolysis bullosa; Epidermolysis bullosa dystrophica (dominant or recessive); Epidermolysis bullosa simplex; Epidermolytic hyperkeratosis; Epidermolytic palmoplantar keratoderma; Epilepsy (generalize; juvenile; myoclonic; nocturnal frontal lobe; progressive myoclonic); Epilepsy, benign, neonatal (type1 or type2); Epiphyseal dysplasia (multiple); Episodic ataxia (type 2); Episodic ataxia/myokymia syndrome; Erythremias (alpha-; dysplasia); Erythrocytosis; Erythrokeratoderma; Estrogen resistance; Exertional myoglobinuria due to deficiency of LDH-A; Exostoses, multiple (type 1; type 2); Exudative vitreoretinopathy, X-linked; Fabry disease; Factor H deficiency; Factor VII deficiency; Factor X deficiency; Factor XI deficiency; Factor XII deficiency; Factor XIIIA deficiency; Factor XIIIB deficiency; Familial Mediterranean fever; Fanconi anemia; Fanconi-Bickel syndrome; Farber lipogranulomatosis; Fatty liver (acute); Favism; Fish-eye disease; Foveal hypoplasia; Fragile X syndrome; Frasier syndrome; Friedreich ataxia; fructose-bisphosphatase Fructose intolerance; Fucosidosis; Fumarase deficiency; Fundus albipunctatus; Fundus flavimaculatus; G6PD deficiency; GABA-transaminase deficiency; Galactokinase deficiency with cataracts; Galactose epimerase deficiency; Galactosemia; Galactosialidosis; GAMT deficiency; Gardner syndrome; Gastric cancer; Gaucher disease; Generalized epilepsy with febrile seizures plus; Germ cell tumors; Gerstmann-Straussler disease; Giant cell hepatitis (neonatal); Giant platelet disorder; Giant-cell fibroblastoma; Gitelman syndrome; Glanzmann thrombasthenia (type A; type B); Glaucoma 1A; Glaucoma 3A; Glioblastoma multiforme; Glomerulosclerosis (focal segmental); Glucose transport defect (blood-brain barrier); Glucose/galactose malabsorption; Glucosidase I deficiency; Glutaricaciduria (type I; type IIB; type IIC); Gluthation synthetase deficiency; Glycerol kinase deficiency; Glycine receptor (alpha-1 polypeptide); Glycogen storage disease I; Glycogen storage disease II; Glycogen storage disease III; Glycogen storage disease IV; Glycogen storage disease VI; Glycogen storage disease VII; Glycogenosis (hepatic, autosomal); Glycogenosis (X-linked hepatic); GM1-gangliosidosis; GM2-gangliosidosis; Goiter (adolescent multinodular); Goiter (congenital); Goiter (non-endemic, simple); Gonadal dysgenesis (XY type); Granulomatosis, septic; Graves disease; Greig cephalopolysyndactyly syndrome; Griscelli syndrome; Growth hormone deficient dwarfism; Growth retardation with deafness and mental retardation; Gynecomastia (familial, due to increased aromatase activity); Gyrate atrophy of choroid and retina with ornithinemia (B6 responsive or unresponsive); Hailey-Hailey disease; Haim-Munk syndrome; Hand-foot-uterus syndrome; Harderoporphyrinuria; HDL deficiency (familial); Heart block (nonprogressive or progressive); Heinz body anemia; HELLP syndrome; Hematuria (familial benign); Heme oxygenase-1 deficiency; Hemiplegic migraine; Hemochromotosis; Hemoglobin H disease; Hemolytic anemia due to ADA excess; Hemolytic anemia due to adenylate kinase deficiency; Hemolytic anemia due to band 3 defect; Hemolytic anemia due to glucosephophate isomerase deficiency; Hemolytic anemia due to glutathione synthetase deficiency; Hemolytic anemia due to hexokinase deficiency; Hemolytic anemia due to PGK deficiency; Hemolytic-uremic syndrome; Hemophagocytic lymphohistiocytosis; Hemophilia A; Hemophilia B; Hemorrhagic diathesis due to factor V deficiency; Hemosiderosis (systemic, due to aceruloplasminemia); Hepatic lipase deficiency; Hepatoblastoma; Hepatocellular carcinoma; Hereditary hemorrhagic telangiectasia-1; Hereditary hemorrhagic telangiectasia-2; Hermansky-Pudlak syndrome; Heterotaxy (X-linked visceral); Heterotopia (periventricular); Hippel-Lindau syndrom; Hirschsprung disease; Histidine-rich glycoprotein Thrombophilia due to HRG deficiency; HMG-CoA lyase deficiency; Holoprosencephaly-2; Holoprosencephaly-3; Holoprosencephaly-4; Holoprosencephaly-5; Holt-Oram syndrome; Homocystinuria; Hoyeraal-Hreidarsson; HPFH (deletion type or nondeletion type); HPRT-related gout; Huntington disease; Hydrocephalus due to aqueductal stenosis; Hydrops fetalis; Hyperbetalipoproteinemia; Hypercholesterolemia, familial; Hyperferritinemia-cataract syndrome; Hyperglycerolemia; Hyperglycinemia; Hyperimmunoglobulinemia D and periodic fever syndrome; Hyperinsulinism; Hyperinsulinism-hyperammonemia syndrome; Hyperkalemic periodic paralysis; Hyperlipoproteinemia; Hyperlysinemia; Hypermethioninemia (persistent, autosomal, dominant, due to methionine, adenosyltransferase I/III deficiency); Hyperornithinemia-hyperammonemiahomocitrullinemia syndrome; Hyperoxaluria; Hyperparathyroidism; Hyperphenylalaninemia due to pterin-4-acarbinolamine dehydratase deficiency; Hyperproinsulinemia; Hyperprolinemia; Hypertension; Hyperthroidism (congenital); Hypertriglyceridemia; Hypoalphalipoproteinemia; Hypobetalipoproteinemia; Hypocalcemia; Hypochondroplasia; Hypochromic microcytic anemia; Hypodontia; Hypofibrinogenemia; Hypoglobulinemia and absent B cells; Hypogonadism (hypergonadotropic); Hypogonadotropic (hypogonadism); Hypokalemic periodic paralysis; Hypomagnesemia; Hypomyelination (congenital); Hypoparathyroidism; Hypophosphatasia (adult; childhood; infantile; hereditary); Hypoprothrombinemia; Hypothyroidism (congenital; hereditary congenital; nongoitrous); Ichthyosiform erythroderma; Ichthyosis; Ichthyosis bullosa of Siemens; IgG2 deficiency; Immotile cilia syndrome-1; Immunodeficiency (T-cell receptor/CD3 complex); Immunodeficiency (X-linked, with hyper-IgM); Immunodeficiency due to defect in CD3-gamma; Immunodeficiency-centromeric instabilityfacial anomalies syndrome; Incontinentia pigmenti; Insensitivity to pain (congenital, with anhidrosis); Insomnia (fatal familial); Interleukin-2 receptor deficiency (alpha chain); Intervertebral disc disease; Iridogoniodysgenesis; Isolated growth hormone deficiency (Illig type with absent GH and Kowarski type with bioinactive GH); lsovalericacidemia; Jackson-Weiss sydnrome; Jensen syndrome; Jervell and Lange-Nielsen syndrome; Joubert syndrom; Juberg-Marsidi syndrome; Kallmann syndrome; Kanzaki disease; Keratitis; Keratoderma (palmoplantar); Keratosis palmoplantaris striata I; Keratosis palmoplantaris striata II; Ketoacidosis due to SCOT deficiency; Keutel syndrome; Klippel-Trenaurnay syndrom; Kniest dysplasia; Kostmann neutropenia; Krabbe disease; Kurzripp-Polydaktylie syndrom; Lacticacidemia due to PDX1 deficiency; Langer mesomelic dysplasia; Laron dwarfism; Laurence-Moon-Biedl-Bardet syndrom; LCHAD deficiency; Leber congenital amaurosis; Left-right axis malformation; Leigh syndrome; Leiomyomatosis (diffuse, with Alport syndrome); Leprechaunism; Leri-Weill dyschondrosteosis; Lesch-Nyhan syndrome; Leukemia (acute myeloid; acute promyelocytic; acute T-cell lymphoblastic; chronic myeloid; juvenile myelomonocytic; Leukemia-1 (T-cell acute lymphocytic); Leukocyte adhesion deficiency; Leydig cell adenoma; Lhermitte-Duclos syndrome; Liddle syndrome; Li-Fraumeni syndrome; Lipoamide dehydrogenase deficiency; Lipodystrophy; Lipoid adrenal hyperplasia; Lipoprotein lipase deficiency; Lissencephaly (X-linked); Lissencephaly-1; liver Glycogen storage disease (type 0); Long QT syndrome-1; Long QT syndrome-2; Long QT syndrome-3; Long QT syndrome-5; Long QT syndrome-6; Lowe syndrome; Lung cancer; Lung cancer (nonsmall cell); Lung cancer (small cell); Lymphedema; Lymphoma (B-cell non-Hodgkin); Lymphoma (diffuse large cell); Lymphoma (follicular); Lymphoma (MALT); Lymphoma (mantel cell); Lymphoproliferative syndrome (X-linked); Lysinuric protein intolerance; Machado-Joseph disease; Macrocytic anemia refractory (of 5q syndrome); Macular dystrophy; Malignant mesothelioma; Malonyl-CoA decarboxylase deficiency; Mannosidosis, (alpha- or beta-); Maple syrup urine disease (type Ia; type Ib; type II); Marfan syndrome; Maroteaux-Lamy syndrome; Marshall syndrome; MASA syndrome; Mast cell leukemia; Mastocytosis with associated hematologic disorder; McArdle disease; McCune-Albright polyostotic fibrous dysplasia; McKusick-Kaufman syndrome; McLeod phenotype; Medullary thyroid carcinoma; Medulloblastoma; Meesmann corneal dystrophy; Megaloblastic anemia-1; Melanoma; Membroproliferative glomerulonephritis; Meniere disease; Meningioma (NF2-related; SIS-related); Menkes disease; Mental retardation (X-linked); Mephenyloin poor metabolizer; Mesothelioma; Metachromatic leukodystrophy; Metaphyseal chondrodysplasia (Murk Jansen type; Schmid type); Methemoglobinemia; Methionine adenosyltransferase deficiency (autosomal recessive); Methylcobalamin deficiency (cbl G type); Methylmalonicaciduria (mutase deficiency type); Mevalonicaciduria; MHC class II deficiency; Microphthalmia (cataracts, and iris abnormalities); Miyoshi myopathy; MODY; Mohr-Tranebjaerg syndrome; Molybdenum cofactor deficiency (type A or type B); Monilethrix; Morbus Fabry; Morbus Gaucher; Mucopolysaccharidosis; Mucoviscidosis; Muencke syndrome; Muir-Torre syndrome; Mulibrey nanism; Multiple carboxylase deficiency (biotinresponsive); Multiple endocrine neoplasia; Muscle glycogenosis; Muscular dystrophy (congenital merosindeficient); Muscular dystrophy (Fukuyama congenital); Muscular dystrophy (limb-girdle); Muscular dystrophy) Duchenne-like); Muscular dystrophy with epidermolysis bullosa simplex; Myasthenic syndrome (slow-channel congenital); Mycobacterial infection (atypical, familial disseminated); Myelodysplastic syndrome; Myelogenous leukemia; Myeloid malignancy; Myeloperoxidase deficiency; Myoadeny late deaminase deficiency; Myoglobinuria/hemolysis due to PGK deficiency; Myoneurogastrointestinal encephalomyopathy syndrome; Myopathy (actin; congenital; desmin-related; cardioskeletal; distal; nemaline); Myopathy due to CPT II deficiency; Myopathy due to phosphoglycerate mutase deficiency; Myotonia congenita; Myotonia levior; Myotonic dystrophy; Myxoid liposarcoma; NAGA deficiency; Nail-patella syndrome; Nemaline myopathy 1 (autosomal dominant); Nemaline myopathy 2 (autosomal recessive); Neonatal hyperparathyroidism; Nephrolithiasis; Nephronophthisis (juvenile); Nephropathy (chronic hypocomplementemic); Nephrosis-1; Nephrotic syndrome; Netherton syndrome; Neuroblastoma; Neurofibromatosis (type 1 or type 2); Neurolemmomatosis; neuronal-5 Ceroid-lipofuscinosis; Neuropathy; Neutropenia (alloimmune neonatal); Niemann-Pick disease (type A; type B; type C1; type D); Night blindness (congenital stationary); Nijmegen breakage syndrome; Noncompaction of left ventricular myocardium; Nonepidermolytic palmoplantar keratoderma; Norrie disease; Norum disease; Nucleoside phosphorylase deficiency; Obesity; Occipital hornsyndrome; Ocular albinism (Nettleship-Falls type); Oculopharyngeal muscular dystrophy; Oguchi disease; Oligodontia; Omenn syndrome; Opitz G syndrome; Optic nerve coloboma with renal disease; Ornithine transcarbamylase deficiency; Oroticaciduria; Orthostatic intolerance; OSMED syndrome; Ossification of posterior longitudinal ligament of spine; Osteoarthrosis; Osteogenesis imperfecta; Osteolysis; Osteopetrosis (recessive or idiopathic); Osteosarcoma; Ovarian carcinoma; Ovarian dysgenesis; Pachyonychia congenita (Jackson-Lawler type or Jadassohn-Lewandowsky type); Paget disease of bone; Pallister-Hall syndrome; Pancreatic agenesis; Pancreatic cancer; Pancreatitis; Papillon-Lefevre syndrome; Paragangliomas; Paramyotonia congenita; Parietal foramina; Parkinson disease (familial or juvenile); Paroxysmal nocturnal hemoglobinuria; Pelizaeus-Merzbacher disease; Pendred syndrome; Perineal hypospadias; Periodic fever; Peroxisomal biogenesis disorder; Persistent hyperinsulinemic hypoglycemia of infancy; Persistent Mullerian duct syndrome (type II); Peters anomaly; Peutz-Jeghers syndrome; Pfeiffer syndrome; Phenylketonuria; Phosphoribosyl pyrophosphate synthetaserelated gout; Phosphorylase kinase deficiency of liver and muscle; Piebaldism; Pilomatricoma; Pinealoma with bilateral retinoblastoma; Pituitary ACTH secreting adenoma; Pituitary hormone deficiency; Pituitary tumor; Placental steroid sulfatase deficiency; Plasmin inhibitor deficiency; Plasminogen deficiency (types I and II); Plasminogen Tochigi disease; Platelet disorder; Platelet glycoprotein IV deficiency; Platelet-activating factor acetylhydrolase deficiency; Polycystic kidney disease; Polycystic lipomembranous osteodysplasia with sclerosing leukenencephalophathy; Polydactyly, postaxial; Polyposis; Popliteal pterygium syndrome; Porphyria (acute hepatic or acute intermittent or congenital erythropoietic); Porphyria cutanea tarda; Porphyria hepatoerythropoietic; Porphyria variegata; Prader-Willi syndrome; Precocious puberty; Premature ovarian failure; Progeria Typ I; Progeria Typ II; Progressive external ophthalmoplegia; Progressive intrahepatic cholestasis-2; Prolactinoma (hyperparathyroidism, carcinoid syndrome); Prolidase deficiency; Propionicacidemia; Prostate cancer; Protein S deficiency; Proteinuria; Protoporphyria (erythropoietic); Pseudoachondroplasia; Pseudohermaphroditism; Pseudohypoaldosteronism; Pseudohypoparathyroidism; Pseudovaginal perineoscrotal hypospadias; Pseudovitamin D deficiency rickets; Pseudoxanthoma elasticum (autosomal dominant; autosomal recessive); Pulmonary alveolar proteinosis; Pulmonary hypertension; Purpura fulminans; Pycnodysostosis; Pyropoikilocytosis; Pyruvate carboxylase deficiency; Pyruvate dehydrogenase deficiency; Rabson-Mendenhall syndrome; Refsum disease; Renal cell carcinoma; Renal tubular acidosis; Renal tubular acidosis with deafness; Renal tubular acidosis-osteopetrosis syndrome; Reticulosis (familial histiocytic); Retinal degeneration; Retinal dystrophy; Retinitis pigmentosa; Retinitis punctata albescens; Retinoblastoma; Retinol binding protein deficiency; Retinoschisis; Rett syndrome; Rh(mod) syndrome; Rhabdoid predisposition syndrome; Rhabdoid tumors; Rhabdomyosarcoma; Rhabdomyosarcoma (alveolar); Rhizomelic chondrodysplasia punctata; Ribbing-Syndrom; Rickets (vitamin D-resistant); Rieger anomaly; Robinow syndrome; Rothmund-Thomson syndrome; Rubenstein-Taybi syndrome; Saccharopinuria; Saethre-Chotzen syndrome; Salla disease; Sandhoff disease (infantile, juvenile, and adult forms); Sanfilippo syndrome (type A or type B); Schindler disease; Schizencephaly; Schizophrenia (chronic); Schwannoma (sporadic); SCID (autosomal recessive, T-negative/Bpositive type); Secretory pathway w/TMD; SED congenita; Segawa syndrome; Selective T-cell defect; SEMD (Pakistani type); SEMD (Strudwick type); Septooptic dysplasia; Severe combined immunodeficiency (B cellnegative); Severe combined immunodeficiency (T-cell negative, B-cell/natural killer cell-positive type); Severe combined immunodeficiency (Xlinked); Severe combined immunodeficiency due to ADA deficiency; Sex reversal (XY, with adrenal failure); Sezary syndrome; Shah-Waardenburg syndrome; Short stature; Shprintzen-Goldberg syndrome; Sialic acid storage disorder; Sialidosis (type I or type II); Sialuria; Sickle cell anemia; Simpson-Golabi-Behmel syndrome; Situs ambiguus; Sjogren-Larsson syndrome; Smith-Fineman-Myers syndrome; Smith-Lemli-Opitz syndrome (type I or type II); Somatotrophinoma; Sorsby fundus dystrophy; Spastic paraplegia; Spherocytosis; Spherocytosis-1; Spherocytosis-2; Spinal and bulbar muscular atrophy of Kennedy; Spinal muscular atrophy; Spinocerebellar ataxia; Spondylocostal dysostosis; Spondyloepiphyseal dysplasia tarda; Spondylometaphyseal dysplasia (Japanese type); Stargardt disease-1; Steatocystoma multiplex; Stickler syndrome; Sturge-Weber syndrom; Subcortical laminal heteropia; Subcortical laminar heterotopia; Succinic semialdehyde dehydrogenase deficiency; Sucrose intolerance; Sutherland-Haan syndrome; Sweat chloride elevation without CF; Symphalangism; Synostoses syndrome; Synpolydactyly; Tangier disease; Tay-Sachs disease; T-cell acute lymphoblastic leukemia; T-cell immunodeficiency; T-cell prolymphocytic leukemia; Thalassemia (alpha- or delta-); Thalassemia due to Hb Lepore; Thanatophoric dysplasia (types I or II); Thiamine-responsive megaloblastic anemia syndrome; Thrombocythemia; Thrombophilia (dysplasminogenemic); Thrombophilia due to heparin cofactor II deficiency; Thrombophilia due to protein C deficiency; Thrombophilia due to thrombomodulin defect; Thyroid adenoma; Thyroid hormone resistance; Thyroid iodine peroxidase deficiency; Tietz syndrome; Tolbutamide poor metabolizer; Townes-Brocks syndrome; Transcobalamin II deficiency; Treacher Collins mandibulofacial dysostosis; Trichodontoosseous syndrome; Trichorhinophalangeal syndrome; Trichothiodystrophy; Trifunctional protein deficiency (type I or type II); Trypsinogen deficiency; Tuberous sclerosis-1; Tuberous sclerosis-2; Turcot syndrome; Tyrosine phosphatase; Tyrosinemia; Ulnar-mammary syndrome; Urolithiasis (2,8-dihydroxyadenine); Usher syndrome (type 1B or type 2A); Venous malformations; Ventricular tachycardia; Virilization; Vitamin K-dependent coagulation defect; VLCAD deficiency; Vohwinkel syndrome; von Hippel-Lindau syndrome; von Willebrand disease; Waardenburg syndrome; Waardenburg syndrome/ocular albinism; Waardenburg-Shah neurologic variant; Waardenburg-Shah syndrome; Wagner syndrome; Warfarin sensitivity; Watson syndrome; Weissenbacher-Zweymuller syndrome; Werner syndrome; Weyers acrodental dysostosis; White sponge nevus; Williams-Beuren syndrome; Wilms tumor (type 1); Wilson disease; Wiskott-Aldrich syndrome; Wolcott-Rallison syndrome; Wolfram syndrome; Wolman disease; Xanthinuria (type I); Xeroderma pigmentosum; X-SCID; Yemenite deaf-blind hypopigmentation syndrome; ypocalciuric hypercalcemia (type I); Zellweger syndrome; Zlotogora-Ogur syndrome.

Diseases to be treated in the context of the present invention likewise also include diseases which have a genetic inherited background and which are typically caused by a single gene defect and are inherited according to Mendel's laws are preferably selected from the group consisting of autosomal-recessive inherited diseases, such as, for example, adenosine deaminase deficiency, familial hypercholesterolaemia, Canavan's syndrome, Gaucher's disease, Fanconi anaemia, neuronal ceroid lipofuscinoses, mucoviscidosis (cystic fibrosis), sickle cell anaemia, phenylketonuria, alcaptonuria, albinism, hypothyreosis, galactosaemia, alpha-1-anti-trypsin deficiency, Xeroderma pigmentosum, Ribbing's syndrome, mucopolysaccharidoses, cleft lip, jaw, palate, Laurence Moon Biedl Bardet sydrome, short rib polydactylia syndrome, cretinism, Joubert's syndrome, type II progeria, brachydactylia, adrenogenital syndrome, and X-chromosome inherited diseases, such as, for example, colour blindness, e.g. red/green blindness, fragile X syndrome, muscular dystrophy (Duchenne and Becker-Kiener type), haemophilia A and B, G6PD deficiency, Fabry's disease, mucopolysaccharidosis, Norrie's syndrome, Retinitis pigmentosa, septic granulomatosis, X-SCID, ornithine transcarbamylase deficiency, Lesch-Nyhan syndrome, or from autosomal-dominant inherited diseases, such as, for example, hereditary angiooedema, Marfan syndrome, neurofibromatosis, type I progeria, Osteogenesis imperfecta, Klippel-Trenaurnay syndrome, Sturge-Weber syndrome, Hippel-Lindau syndrome and tuberosis sclerosis.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients which undergo a (regular) a kidney or renal dialysis, and which may be in need of specific therapeutically active proteins as defined above, e.g. erythropoietin (EPO), etc.

Likewise, diseases in the context of the present invention may include cardiovascular diseases chosen from, without being limited thereto, coronary heart disease, arteriosclerosis, apoplexy and hypertension, etc.

Finally, diseases in the context of the present invention may be chosen from neuronal diseases including e.g. Alzheimer's disease, amyotrophic lateral sclerosis, dystonia, epilepsy, multiple sclerosis and Parkinson's disease etc.

According to a final embodiment, the present invention also provides kits, particularly kits of parts. Such kits of parts may contain e.g. a pharmaceutical composition or a vaccine as defined above, preferably divided into different parts of the kit. As an example, the inventive pharmaceutical composition or the inventive vaccine may be prepared as a kit of parts, e.g. by incorporating into one or more parts of the kit components of the inventive pharmaceutical composition or the inventive vaccine as described herein as a dry formulation, i.e. devoid of any liquid component, and in at least one further separate part of the kit water, a liquid and/or a buffer as described herein for the inventive pharmaceutical composition or the inventive vaccine or a liquid and/or a buffer as described herein for the inventive solution for lyophilization, transfection and/or injection, e.g. an isotonic salt solution. Alternatively, the inventive pharmaceutical composition or the inventive vaccine may be prepared as a kit of parts, e.g. by incorporating into one or more parts of the kit the lyophilized nucleic acid (sequence) as described herein, i.e. devoid of any liquid component, and in at least one further separate part of the kit a liquid and/or a buffer as described herein for the inventive pharmaceutical composition or the inventive vaccine or a liquid and/or a buffer as described herein for the inventive solution for lyophilization, transfection and/or injection, e.g. an isotonic salt solution. Further components may be incorporated in such kits of parts as described above for the inventive solution for lyophilization, transfection and/or injection or as described above for the inventive pharmaceutical composition or as described above for the inventive vaccine e.g. in the dry part(s) of the kit, in the liquid part(s) of the kit, preferably in solubilized form, or in at least one separate part of the kit as a dry form and/or in a lyophilized (liquid) form. Such kits, preferably kits of parts, may be applied, e.g., for any of the above mentioned applications or uses. The kit may optionally contain technical instructions with information on the administration and dosage of the lyophilized nucleic acid. Kit of parts, comprising in one or more parts of the kit at least one lyophilized nucleic acid as defined herein, and optionally in one or more parts of the kit further additives as defined herein, and in one or more parts of the kit water, a liquid and/or a buffer or solution as defined herein, and optionally technical instructions with information on the administration and dosage of the lyophilized nucleic acid.

EXAMPLES

The following examples are intended to illustrate the invention further. They are not intended to limit the subject matter of the invention thereto.

Example 1

Preparation of Plasmids

For the present examples DNA sequences encoding *Photinus pyralis* luciferase as well as DNA sequences encoding Ovalbumin were prepared and used for subsequent in vitro transcription reactions and expression studies.

According to a first preparation, the DNA sequence corresponding to pCV 19-Ppluc(GC)-muag-A70-C30 was prepared, which encodes the *Photinus pyralis* luciferase coding sequence. The constructs were prepared by modifying the wild type *Photinus pyralis* luciferase encoding DNA sequence by introducing a GC-optimized sequence for a better codon usage and stabilization, stabilizing sequences derived from alpha-globin-3'-UTR (muag (mutated alpha-globin-3'-UTR)), a stretch of 70×adenosine at the 3'-terminal end (poly-A-tail) and a stretch of 30×cytosine at the 3'-terminal end (poly-C-tail), corresponding to SEQ ID NO: 1 (see FIG. 5). The sequence of the final DNA construct had a length of 1857 nucleotides. The corresponding mRNA sequence was termed "pCV19-Ppluc(GC)-muag-A70-C30" (SEQ ID NO: 1) (see FIG. 5).

According to a second preparation, the DNA sequence corresponding to CAP-GgOva(GC)-muag-A70-C30 was prepared, which encodes to the Ovalbumin coding sequence. Therefore, a basic DNA construct was prepared corresponding to CAP-GgOva(GC)-muag-A70-C30 by introducing into the underlying wild type sequence construct stabilizing sequences derived from alpha-globin-3'-UTR (muag (mutated alpha-globin-3'-UTR)), a stretch of 70×adenosine at the 3'-terminal end (poly-A-tail) and a stretch of 30×cytosine at the 3'-terminal end (poly-C-tail), leading to a sequence corresponding to SEQ ID NO: 2 (see FIG. 6). The corresponding mRNA sequence was termed CAP-GgOva(GC)-muag-A70-C30 (SEQ ID NO: 2) (see FIG. 6).

Both sequences contain following sequence elements:
the coding sequence encoding *Photinus pyralis* luciferase (SEQ ID NO: 1) or *Gallus gallus* Ovalbumin (SEQ ID NO: 2);
stabilizing sequences derived from alpha-globin-3'-UTR (muag (mutated alpha-globin-3'-UTR));
70×adenosine at the 3'-terminal end (poly-A-tail);
30×cytosine at the 3'-terminal end (poly-C-tail).

Example 2

In Vitro Transcription

The respective DNA plasmids prepared according to Example 1 were transcribed in vitro using T7-Polymerase (T7-Opti mRNA Kit, CureVac, Tübingen, Germany) following the manufactures instructions. Subsequently the mRNA was purified using PureMessenger® (CureVac, Tübingen, Germany).

Example 3

Lyophylisation

The PureMessenger® purified and precipitated mRNA obtained according to Examples 1 and 2 coding for *Photinus pyralis* luciferase (Luc mRNA) (SEQ ID NO: 1) or Ovalbumin (SEQ ID NO: 2) were prepared for transfection and expression tests.

The PureMessenger® purified and precipitated mRNA obtained according to Examples 1 and 2 coding for *Photinus pyralis* luciferase (Luc mRNA) (SEQ ID NO: 1) or Ovalbumin (SEQ ID NO: 2) was dissolved in water for injection (WFI) to 5 g/l. Subsequently the mRNA was diluted with WFI (water for injection) or salt solution (see FIG. 2), with addition of glucose, trehalose, mannite or mannose. Aliquots of these solutions were lyophilized (Controls were frozen in liquid nitrogen or kept in solution). The locked cups were stored for the indicated time at 60° C. The resuspension was conducted with WFI.

Example 4

In Vivo Expression of the RNA Constructs

In the present experiment following solutions for lyophilization were used:
WFI (water for injection): purified mRNA coding for luciferase with a concentration of 4.9 g/l in WFI was diluted with WFI to a final mRNA concentration of 0.05 g/l.
Buffer containing mannose: 0.25 g mannose was diluted with 10 ml WFI and passed through a syringe filter tip 0.22 µm resulting in a sterile 2.5% (w/w) mannose containing solution. Purified mRNA coding for luciferase with a concentration of 4.9 g/l in WFI was diluted with the sterile 2.5% (w/w) mannose solution to a final mRNA concentration of 0.05 g/l.

Buffer containing trehalose: 0.5 g trehalose was diluted with 10 ml WFI and passed through a syringe filter tip 0.22 μm resulting in a sterile 5% (w/w) trehalose containing solution. Purified mRNA coding for luciferase with a concentration of 4.9 g/l in WFI was diluted with the sterile 5% (w/w) trehalose solution to a final mRNA concentration of 0.05 g/l.

Buffer containing mannite: 0.5 g mannite was diluted with 10 ml WFI and passed through a syringe filter tip 0.22 μm resulting in a sterile 5% (w/w) mannite containing solution. Purified mRNA coding for luciferase with a concentration of 4.9 g/l in WFI was diluted with the sterile 5% (w/w) mannite solution to a final mRNA concentration of 0.05 g/l. The dilution errors for mannose, trehalose, and mannite were neclectable.

Buffer control Ringer lactate solution 80% in WFI was used (not lyophilized);

Lyophilization:

The mRNA containing buffers were frozen by liquid nitrogen for at least 5 min and lyophilized over night at 0.08 mbar in a freeze drier Alpha 1-2 (Fa. Martin Christ Gefriertrocknungsanlagen GmbH, Osterode, Germany). The lyophilisates were dissolved with a sterile salt containing solution (5 mM KCl, 2 mM $CaCl_2$, 2 mM $MgCl_2$, 130 mM NaCl in WFI).

In Vivo Expression:

Each group (2 mice per group) of 7 week old female balb/c mice were treated by intradermal injection with 100 μl of each sample. After 24 h mice were killed and the injected tissue was collected and lysed as described ahead. Tissue samples were crushed by a mill after freezing in liquid nitrogen and lysed afterwards by adding 800 μl of lysing buffer (25 mM Tris HCL, 2 mM EDTA, 10% Glycerol, 1% Triton X-100, 2 mM DTT, 1 mM PMSF, pH 7.5-7.8). The lysates were shaked for 6 min and spinned down for another 10 min at 4° C. and 13500 rpm. The supernatants were measured with a luminometer LB9507 and analyzed as grouped analysis using 2-way ANOVA with Bonferroni post test.

The results are shown in FIG. 1. FIG. 1 shows the in vivo luciferase expression in balb/c mice 1) buffer control: Ringer-lactate 2) mRNA/WFI: mRNA coding for luciferase lyophilized in WFI (water for injection) and dissolved in salt containing solution 3) mRNA/trehalose: mRNA coding for luciferase lyophilized in WFI containing 5% trehalose and dissolved in salt containing solution 4) mRNA/mannose: mRNA coding for luciferase lyophilized in WFI containing 2.5% mannose and dissolved in salt containing solution 5) mRNA/mannite: mRNA coding for luciferase lyophilized in WFI containing 5% mannite and dissolved in salt containing solution.

Discussion:

After an intradermal injection in balb/c mice of mRNA coding for *Photinus pyrialis* luciferase (PpLuc RNA) (0.05 g/L) dissolved in a salt solution (5 mM KCl, 130 mM NaCl, 2 mM Ca, 2 mM Mg) which was lyophilized in WFI (water of injection) plus 2.5% (w/w) mannose, the luciferase expression increases by a factor of more than 20 compared to an injection of mRNA which was lyophilized in WFI without mannose (see FIG. 1). Other sugars (trehalose and mannite) which were added to the solution before lyophilization could not improve the expression of the encoded protein.

Example 5

Determination of the Stability of RNA

In the following a comparison of the stability of RNA in solution and lyophilized RNA and a comparison of the stability of RNA lyophilized from mannose or glucose containing solution was carried out.

a) Comparison of the Stability of RNA in Solution and Lyophilized RNA:

mRNA was complexed with protamine according to the following protocol. RNA was first mixed at a ratio 4:1 RNA/Protamine (w/w) with a protamine containing salt solution (5 mM KCl, 2 mM CaCl, 2 mM MgCl, 130 mM NaCl) to a final RNA concentration of 0.4 g/l. Mannose was added to the solution in a final concentration of 2.5% (w/w).

The solution was divided into 65 μl containing aliquots in 2 ml polypropylene tubes with crewed caps. Half of the samples were frozen by liquid nitrogen for at least 5 min and lyophilized over night at 0.08 mbar in a freeze drier Alpha 1-2 (Fa. Martin Christ Gefriertrocknungsanlagen GmbH, Osterode, Germany). Liquid and lyophilized samples were stored at 60° C. for 1 to 5 weeks. Every week 2 aliquotes of each lyophilisat were dissolved in 65 μl WFI. 50 μl of each sample were precipitated with 2-propanole. The pellets were diluted in 50 μl WFI again and for 1 μg of each sample an agarose gel electrophoresis was conducted. After separation the relative integrity of RNA was measured as the relation between full length product and total RNA calculated in %. 70% relative integrity was found to be a typical limit for an intact product accepted by the authorities.

Figure 2:
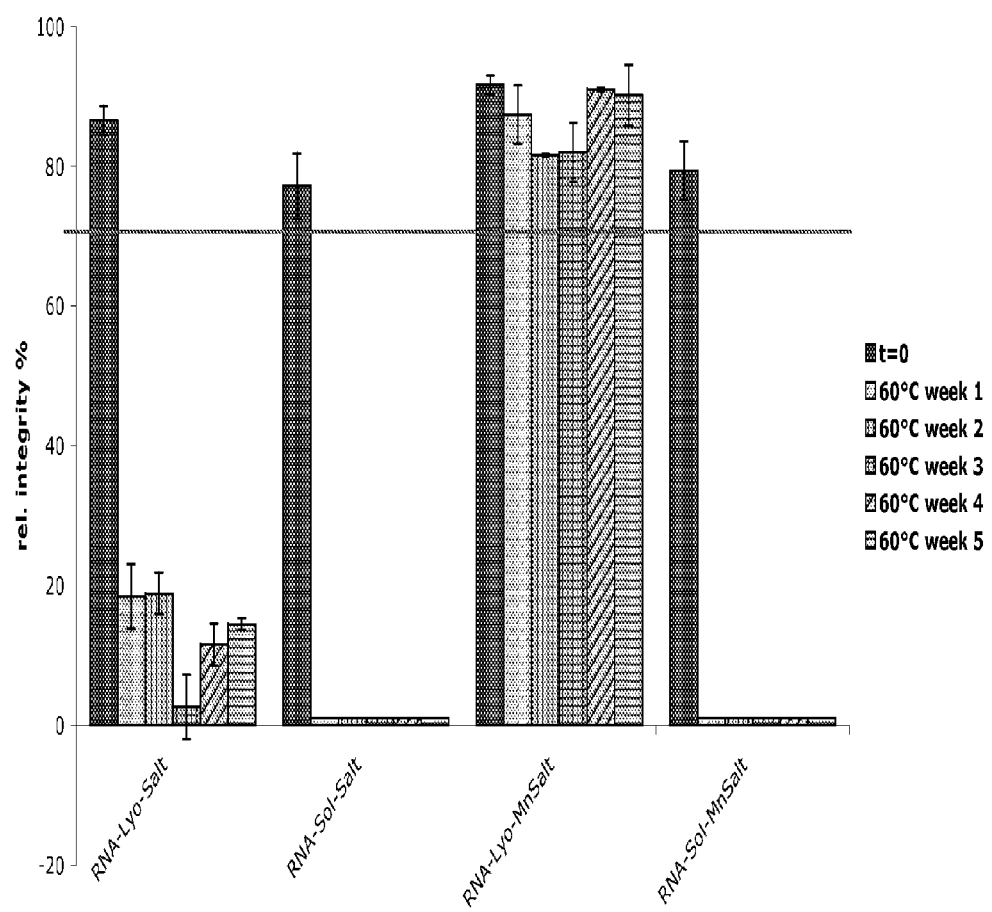
FIG. 2: displays the relative integrity of RNA in mRNA/protamine containing samples dissolved in salt containing solution (5 mM K, 2 mM Ca, 2 mM Mg, 130 mM Na) and subsequently 1) lyophilized from salt solution (1=RNA-Lyo-Salt) 2) stored in salt solution (2=RNA-Sol-Salt) 3) lyophilized from 2.5% mannose containing salt solution (3=RNA-Lyo_MnSalt) or 4) stored in 2.5% mannose containing salt solution (4=RNA-Sol_MnSalt). Comparison of the lyophilized samples clearly shows that storage of RNA at 60° C. is not possible when lyophilized from a salt containing solution. However, addition of mannose leads to an absolutely unexpected stabilization of the RNA, although it is believed in the state of the art that presence of salts is adverse and therefore should be avoided.

The results are described in FIG. 2. FIG. 2 shows the relative integrity of RNA in mRNA/protamine containing samples dissolved in salt containing solution (5 mM K, 2 mM Ca, 2 mM Mg, 130 mM Na) and subsequently 1) lyophilized from salt solution (1=RNA-Lyo-Salt) 2) stored in salt solution (2=RNA-Sol-Salt) 3) lyophilized from 2.5% mannose containing salt solution (3=RNA-Lyo_MnSalt) or 4) stored in 2.5% mannose containing salt solution (4=RNA-Sol_MnSalt).

Discussion:

It is remarkable that RNA cannot be stored at 60° C. neither in the salt solution nor in the mannose containing salt solution. Comparison of the lyophilized samples clearly shows that storage of RNA at 60° C. is not possible when lyophilized from a salt containing solution. However, addition of mannose leads to an absolutely unexpected stabilization of the RNA, although it is believed in the state of the art that presence of salts is adverse and therefore should be avoided.

b) Comparison of the Stability of RNA Lyophilized from Mannose or Glucose Containing Solution mRNA was complexed with protamine in the following protocol. RNA was mixed at a ratio 4:1 RNA/Protamine (w/w) with a diluted protamine solution containing protamine, WFI and mannose or glucose to a final RNA concentration of 0.4 g/l and 5% (w/w) mannose or 5% (w/w) glucose.

The solution was divided into 65 μl containing aliquots in 2 ml polypropylene tubes with crewed caps, frozen by liquid nitrogen for at least 5 min and lyophilized over night at 0.08 mbar in a freeze drier Alpha 1-2 (Fa. Martin Christ Gefriertrocknungsanlagen GmbH, Osterode, Germany). The samples were stored at 60° C. for 0-33 days. At the indicated time points 2 aliquotes of each sample were dissolved in 65 μl WFI. 50 μl of each sample were precipitated with 2-propanole. The pellets were diluted in 50 μl WFI again and for 1 μg of each sample an agarose gel electrophoresis was conducted. After separation the relative integrity of RNA was measured as the relation between full length product and total RNA calculated in %. 70% relative integrity was found to be a typical limit for an intact product accepted by the authorities.

Figure 3:
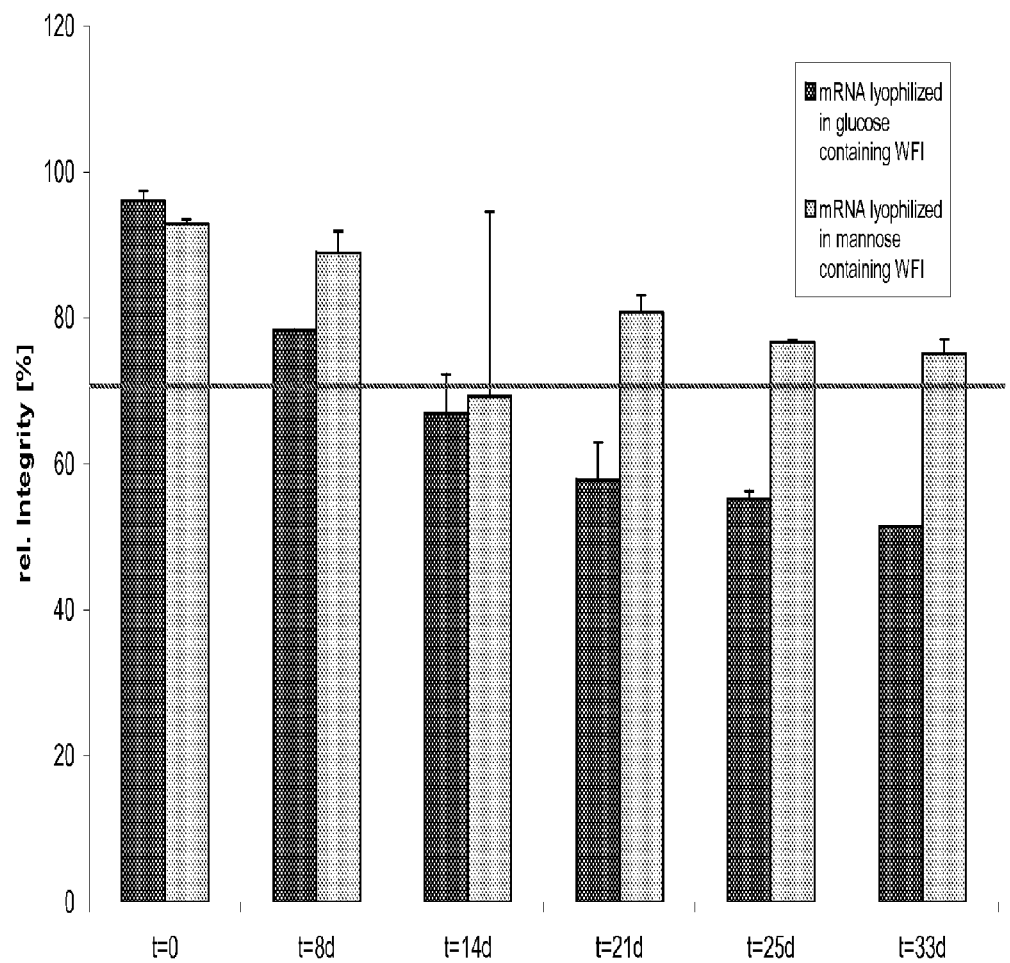
FIG. 3: shows the relative integrity of mRNA lyophilized in a glucose or mannose containing solution stored at 60° C. for 0 to 33 days (d). Mannose clearly increases the stability of lyophilized RNA compared to the addition of glucose.

The results are shown in FIG. 3. FIG. 3 depicts the relative integrity of mRNA lyophilized in a glucose or mannose containing solution stored at 60° C. for 0 to 33 days (d).

Discussion:

This experiment shows that mannose clearly increases the stability of lyophilized RNA compared to the addition of glucose. This is remarkable because mannose is the epimer of glucose and therefore nobody skilled in the art would have expected that mannose is more effective in stabilization of RNA than glucose.

Example 6

Tumour Challenge

The samples used in this experiment were:

OVA-RNActive in RiLa: mRNA coding for Gallus gallus ovalbumine complexed with protamine and dissolved in 80% Ringer lactate OVA-RNActive lyophilized in 2.5% (w/w) mannose: mRNA coding for Gallus gallus ovalbumine complexed with protamine, lyophilized in WFI containing 2.5% (w/w) mannose and dissolved in 80% Ringer lactate RiLa control: 80% Ringer lactate was used as control mRNA coding for ovalbumine was complexed with protamine in the following protocol. RNA was mixed at a ratio 4:1 RNA/Protamine (w/w). Mannose was added to a final concentration of 2.5% (w/w).

The mannose containing RNA solution was aliquoted into a borosilicate glas typ I and frozen by liquid nitrogen for at least 5 min and lyophilized at 0.055 mbar for 22 h. Sample plates were kept at room temperature for 17 h and were than elevated to 35° C. for another 5 h. The chamber was flooded with dry argon and the samples were closed under this atmosphere by a bromobutyl stopper. The lyophilized and non-lyophilized samples were stored in an exsiccator at 4-8° C. and the lyophilized sample was dissolved in 80% Ringer lactate prior to use. Prior use the samples were controlled for relative integrity by agarose gel chromatography and complex size by dynamic light scattering using a Zetasizer Nano (Malvern Instruments, Malvern, UK).

7 week old C57BL/6 mice were vaccinated intradermally with 2 cycles (Prime day 1/Boost day 9) of 80 μl formulations. As a negative control 80 μl 80% Ringer lactate without any RNA were injected. At day 15 1×10$^6$ E.G7-OVA cells (tumour cells which stably express ovalbumine) per mice were implanted subcutaneously. Tumour growth was monitored by measuring the tumor size in 3 dimensions using a calliper.

Figure 4:
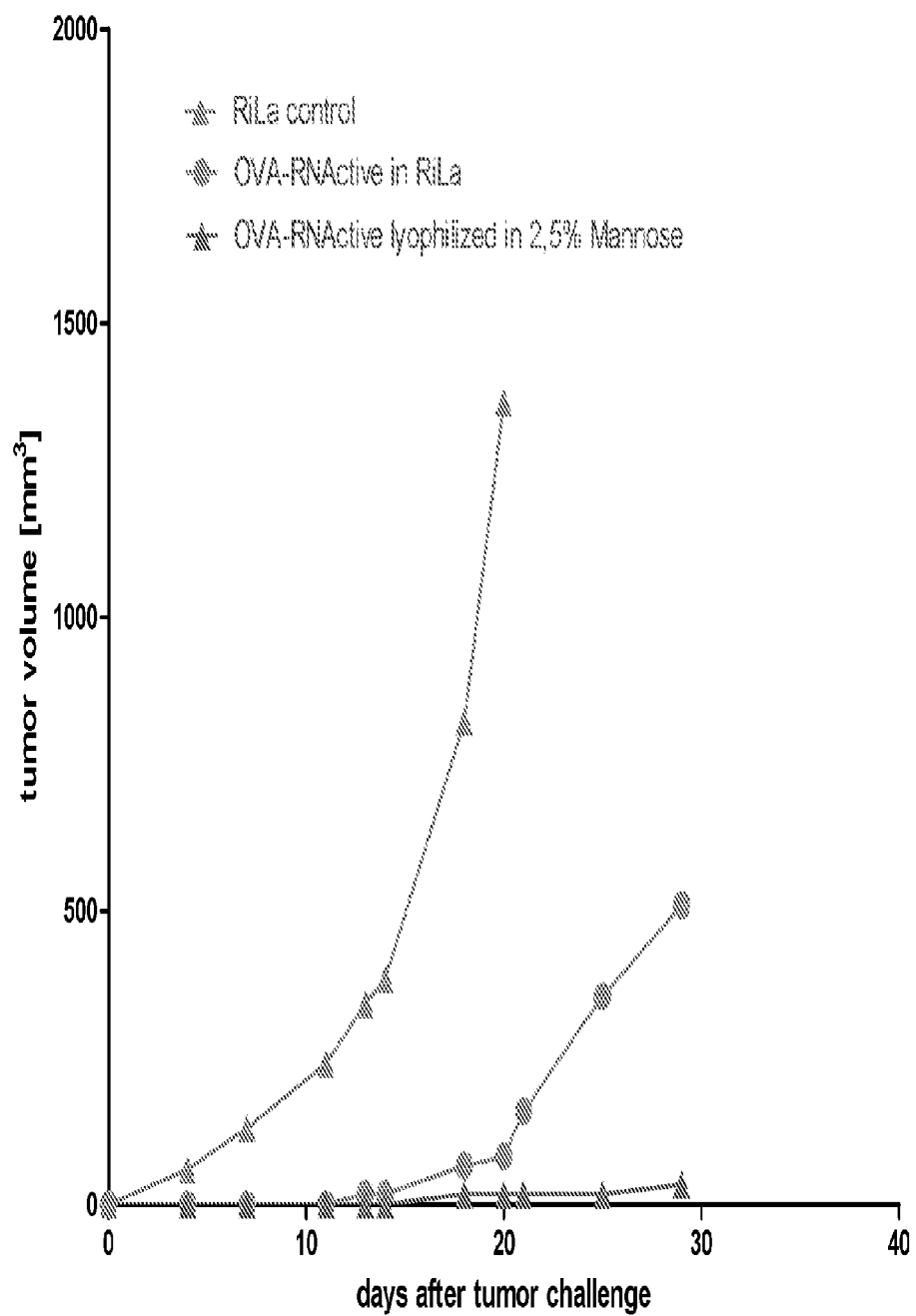
FIG. 4: depicts the tumour growth in mice vaccinated with 1) 80% Ringer lactate as control, 2) mRNA coding for ovalbumine (not lyophilized) in 80% Ringer lactate and 3) mRNA coding for ovalbumine lyophilized in 2.5% (w/w) Mannose containing WFI and dissolved in 80% Ringer lactate. It is remarkable that the mannose-containing solution extremely enhances the efficacy of the mRNA vaccination compared to the sample without mannose. Since the samples were controlled for integrity and complex size it is guaranteed that the RNA was intact in all samples. The optimal concentration of mannose is located between 1% and 10%.

The results are shown in FIG. 4. FIG. 4 depicts the tumour growth in mice vaccinated with 1) 80% Ringer lactate as control, 2) mRNA coding for ovalbumine (not lyophilized) in 80% Ringer lactate and 3) mRNA coding for ovalbumine lyophilized in 2.5% (w/w) mannose containing WFI and dissolved in 80% Ringer lactate.

Discussion:

It is remarkable that a mannose-containing solution extremely enhances the efficacy of the mRNA vaccination compared to the sample without mannose. Since the samples were controlled for integrity and complex size it is guaranteed that the RNA was intact in all samples.

The optimal concentration of mannose is located between 1% and 10%. The formulation of the injection solution can contain different salts (e.g. 0.5 mM to 50 mM potassium, 13 mM to 250 mM sodium, 0.2 mM to 10 mM calcium, and 0.2 mM to 10 mM magnesium). Different injection solutions can be utilized, e.g. PBS, HBSS, Ringer-Lactat.

The invention claimed is:

1. A lyophilized nucleic acid composition comprising, a plurality of mRNA molecules encoding a tumor or infectious disease antigen and a free, unconjugated and non-covalently bound mannose at a concentration of 0.5% (w/w) to 10% (w/w).

2. The lyophilized nucleic acid composition of claim 1, wherein the residual water content of the lyophilized nucleic acid composition is reduced to a content of 0.5% (w/w) to 5% (w/w).

3. The lyophilized nucleic acid composition of claim 1, wherein the lyophilized nucleic acid molecule has a relative integrity of at least about 70%.

4. The lyophilized nucleic acid composition of claim 1, wherein the mRNA is complexed with a cationic or polycationic compound.

5. The lyophilized nucleic acid composition of claim 4, wherein the mRNA is complexed with protamine.

6. The lyophilized nucleic acid composition of claim 1, wherein the composition is free of DNA.

7. A solution comprising a plurality of mRNA molecules encoding a tumor or infectious disease antigen and a free, unconjugated and non-covalently bound mannose at a concentration of 0.5% (w/w) to 10% (w/w).

8. The solution of claim 7, wherein the mannose concentration of the solution is in the range of 0.5 to 5% (w/w).

9. The solution of claim 7, wherein the mRNA is complexed with a cationic or polycationic compound.

10. The solution of claim 9, wherein the mRNA is complexed with protamine.

11. The solution of claim 7, wherein the solution is free of DNA.

12. The solution of claim 7, wherein the mannose is selected from α-D-Mannofuranose, β-D-Mannofuranose, α-D-Mannopyranose and β-D-Mannopyranose.

13. The solution of claim 7, wherein the solution is present in an osmolarity in the range of about 200 mosmol/l to about 400 mosmol/l.

14. The solution of claim 7, wherein the solution additionally comprises an isotonic buffer or its components selected from phosphate-buffered saline (PBS), TRIS-buffered saline (TBS), Hank's balanced salt solution (HBSS), Earle's balanced salt solution (EBSS), standard saline citrate (SSC), HEPES-buffered saline (FIBS), Grey's balanced salt solution (GBSS), normal saline (NaCl), and hypotonic (saline) solutions with addition of glucose or dextrose.

15. The solution of claim 7, wherein the solution additionally comprises lactic acid.

16. The solution of claim 7, wherein the solution additionally comprises an additive selected from the group consisting of mannite, polypeptides, amino acids, alcohols, carbohydrates, metals, metal ions, surfactants, polymers, complexing agents, and a buffer.

17. The solution of claim 15, wherein the lactic acid is selected from the group consisting of L-(+)-lactic acid, (S)-lactic acid, D-(−)-lactic acid, (R)-lactic acid, and L-(+)-lactic acid, or a salt or an anion thereof.

18. The solution of claim 15, wherein the lactic acid is selected from the group consisting of sodium-lactate, potassium-lactate, $Al^{3+}$-lactate, $NH^{4+}$-lactate, Fe-lactate, Li-lactate, Mg-lactate, Ca-lactate, Mn-lactate and Ag-lactate.

19. The solution of claim 7, wherein the solution comprises Ringer's lactate (RiLa), acetated Ringer's solution, lactate containing water or ortholactate-containing solutions.

20. The solution of claim 10, wherein the solution is free of DNA and the mRNA is complexed with protamine.

* * * * *

UNITED STATES PATENT AND TRADEMARK OFFICE
CERTIFICATE OF CORRECTION

| | |
|---|---|
| PATENT NO. | : 9,616,084 B2 |
| APPLICATION NO. | : 14/492334 |
| DATED | : April 11, 2017 |
| INVENTOR(S) | : Thorsten Mutzke |

It is certified that error appears in the above-identified patent and that said Letters Patent is hereby corrected as shown below:

In the Claims

In Claim 14, Column 112, Line 39, delete "(FIBS)" and insert --(HBS)-- therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*